US010428176B2

(12) United States Patent
Chun et al.

(10) Patent No.: US 10,428,176 B2
(45) Date of Patent: Oct. 1, 2019

(54) THERMOSETTING ALKOXYSILYL COMPOUND HAVING TWO OR MORE ALKOXYSILYL GROUPS, COMPOSITION AND CURED PRODUCT COMPRISING SAME, USE THEREOF, AND METHOD FOR PREPARING ALKOXYSILYL COMPOUND

(71) Applicant: KOREA INSTITUTE OF INDUSTRIAL TECHNOLOGY, Cheonan (KR)

(72) Inventors: Hyun-Aee Chun, Seongnam (KR); Sung-Hwan Park, Gunpo (KR); Yun-Ju Kim, Seoul (KR); Su-Jin Park, Ansan (KR); Sook-Yeon Park, Gunpo (KR); Sang-Yong Tak, Busan (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 0 days.

(21) Appl. No.: 15/534,451

(22) PCT Filed: Dec. 9, 2014

(86) PCT No.: PCT/KR2014/012072
§ 371 (c)(1),
(2) Date: Jun. 8, 2017

(87) PCT Pub. No.: WO2016/093383
PCT Pub. Date: Jun. 16, 2016

(65) Prior Publication Data
US 2018/0155370 A1 Jun. 7, 2018

(51) Int. Cl.
*C08G 59/40* (2006.01)
*C08L 63/00* (2006.01)
*C07F 7/18* (2006.01)
*C08K 7/14* (2006.01)
*C08K 3/36* (2006.01)
*C08G 59/20* (2006.01)

(52) U.S. Cl.
CPC ........ *C08G 59/4085* (2013.01); *C07F 7/1804* (2013.01); *C08G 59/20* (2013.01); *C08K 3/36* (2013.01); *C08K 7/14* (2013.01); *C08L 63/00* (2013.01)

(58) Field of Classification Search
None
See application file for complete search history.

(56) References Cited

U.S. PATENT DOCUMENTS

| 5,316,855 | A | 5/1994 | Wang et al. |
| 6,335,414 | B1* | 1/2002 | Sakamoto ................ C08K 5/54 |
| | | | 528/34 |
| 6,534,568 | B1 | 3/2003 | Katz et al. |
| 8,211,546 | B2 | 7/2012 | Fukushima et al. |
| 2007/0254222 | A1 | 11/2007 | Bender et al. |
| 2010/0092686 | A1 | 4/2010 | Laryea et al. |
| 2011/0034626 | A1* | 2/2011 | Fukushima .......... C09D 183/06 |
| | | | 524/588 |
| 2011/0159439 | A1* | 6/2011 | Kawashima ............... B41C 1/05 |
| | | | 430/306 |
| 2012/0123051 | A1 | 5/2012 | Kuwata |
| 2015/0105493 | A1 | 4/2015 | Chun et al. |
| 2015/0246521 | A1* | 9/2015 | Fathi ................... B41J 2/17559 |
| | | | 606/214 |

FOREIGN PATENT DOCUMENTS

| CN | 101816926 A | | 9/2010 |
| JP | 59-197421 A | | 11/1984 |
| JP | 4-36291 A | | 2/1992 |
| JP | 2005-113000 A | * | 4/2005 |
| JP | 2005-336329 A | | 12/2005 |
| JP | 2005336329 A | * | 12/2005 |
| JP | 2007-9072 A | | 1/2007 |
| JP | 2007-296519 A | | 11/2007 |
| JP | 2009-68017 A | | 4/2009 |
| JP | 2009-298995 A | | 12/2009 |
| JP | 2009298995 A | * | 12/2009 |
| JP | 4618407 B2 | | 5/2010 |
| JP | 2010-524670 A | | 7/2010 |
| JP | 2011-37969 A | | 2/2011 |
| JP | 2011026523 A | | 2/2011 |
| JP | 2011-236153 A | | 11/2011 |
| JP | 2011236153 A | * | 11/2011 |
| JP | 2013190542 A | * | 9/2013 |
| KR | 2012-0058345 | * | 6/2012 |
| KR | 10-1225319 B1 | | 1/2013 |

(Continued)

OTHER PUBLICATIONS

Machine-generated translation of JP 2005-113000 (no date).*

(Continued)

*Primary Examiner* — Marc S Zimmer

(57) ABSTRACT

The present invention relates to: a thermosetting alkoxysilyl compound (hereinafter, referred to as "alkoxysilyl compound") having two or more alkoxysilyl groups showing excellent heat-resistance characteristics in a composite; a composition and a cured product comprising the same; a use thereof; and a method for preparing an alkoxysilyl compound. The composition of an alkoxysilyl compound, comprising a novel alkoxysilyl compound according to the present invention shows, in a composite, improved heat-resistance characteristics, i.e., an effect of decreasing the CTE of the composition of an alkoxysilyl compound and not showing a glass transition temperature (hereinafter, referred to as "Tg-less"). Further, the cured product comprising an alkoxysilyl compound according to the present invention shows excellent flame retardant properties due to the alkoxysilyl groups.

11 Claims, 3 Drawing Sheets

(56) References Cited

FOREIGN PATENT DOCUMENTS

| KR | 10-2013-0111299 A | 10/2013 |
|---|---|---|
| KR | 10-2014-0144663 A | 12/2014 |
| WO | 2007126410 A2 | 11/2007 |

OTHER PUBLICATIONS

Machine-generated translation of KR 2012-0058345 (no date).*
"Heirarchically Imprinted Porous Films for Rapid and Selective Detection of Explosives" authored by Zhu et al. and published in Langmuir (2011) 27, 8451-8457.*
Hironobu Muramatsu et al., "Solid State Hydrolysis/Polycondensation of Alkoxysilane: Access to Crystal-Lake Silicon-Based Hybrid Materials", J. Am. Chem. Soc., 2003, pp. 854-855, vol. 125, American Chemical Society.
Susumu Harashima et al., "Development of elastic adhesive based on poly(oxyalkylene)s containing a reactive silicone group", Bulletin of Engineering Faculty, 2006, pp. 43-48, vol. 29, No. 1, Tokyo Polytechnic University.
Database Registgry [Online]: Chemical Abstracts Service, Retrieved from STN, Registry No. 1415316-35-6, Dec. 21, 2012, pp. 1A-1B, Columbus, Ohio, USA.
Constantin Bolcu et al., "Synthesis and thermal behavior of some diisocyanate-silane compounds", J. Therm. Anal. Calorim., 2014, pp. 489-494 vol. 115, Springer.
Xiao-Yan Cui et al., "Synthesis and Optical Properties of Organic-Inorganic Hybrid Mesoporous Materials with Naphthalene Bridging Groups", 2013, pp. 639-645, vol. 29, No. 3, Acta Physico-Chimica Sinica.
International Search Report for PCT/KR2014/012072 filed on Dec. 9, 2014.

* cited by examiner

[Figure 1]
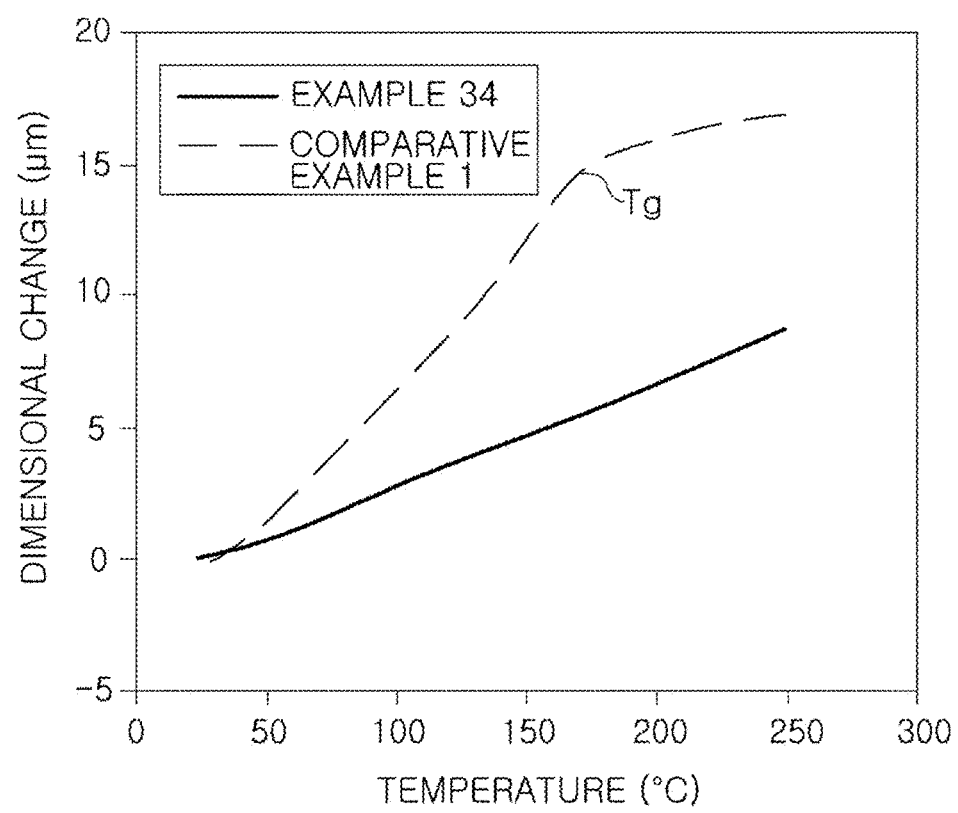

【Figure 2】
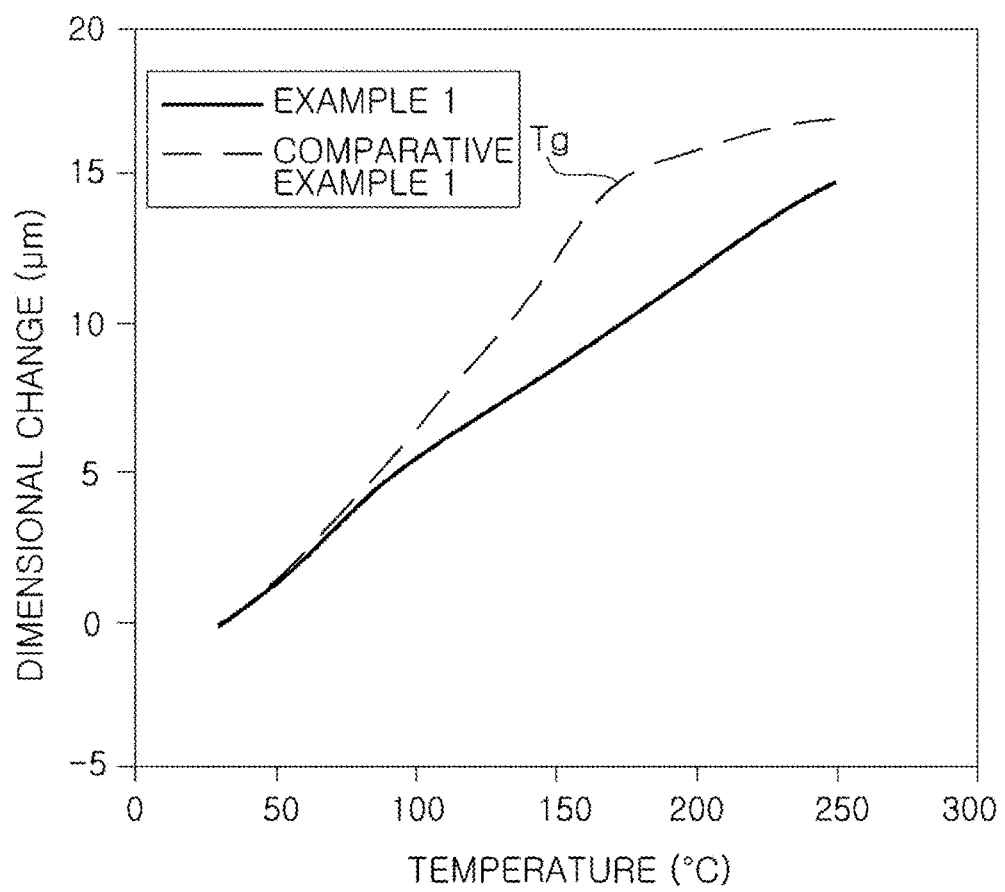

【Figure 3】
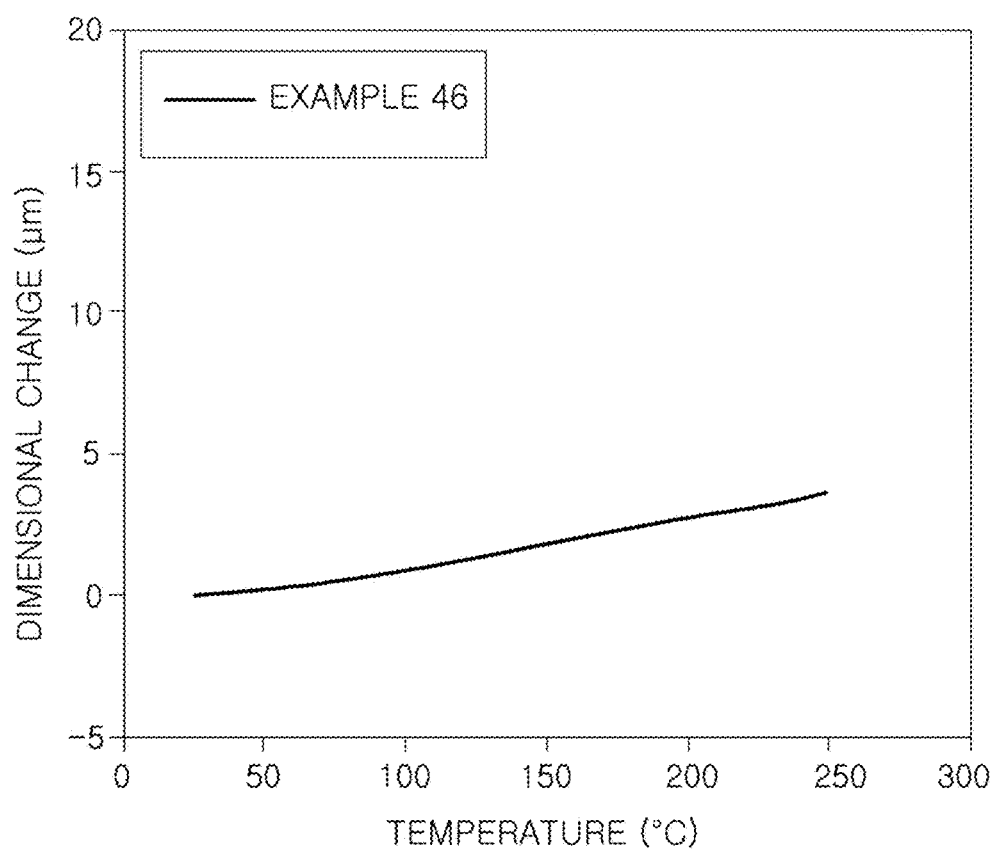
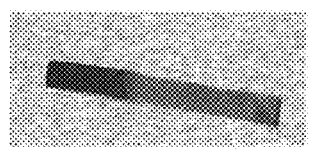
EXAMPLE 1
FIG. 4A
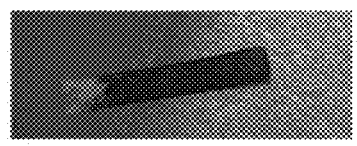
COMPARATIVE EXAMPLE 1
FIG. 4B

THERMOSETTING ALKOXYSILYL COMPOUND HAVING TWO OR MORE ALKOXYSILYL GROUPS, COMPOSITION AND CURED PRODUCT COMPRISING SAME, USE THEREOF, AND METHOD FOR PREPARING ALKOXYSILYL COMPOUND This application is a U.S. National Stage of PCT/KR2014/012072, filed Dec. 9, 2014, the disclosure of which is incorporated herein by reference.

TECHNICAL FIELD

The present invention relates to a thermosetting alkoxysilyl compound (hereinafter 'alkoxysilyl compound') having two or more alkoxysilyl groups exhibiting excellent heat resistance properties in a composite, a composition including the same, a cured product formed of the composition, a use of the cured product, and a method for preparing the alkoxysilyl compound. More particularly, the present invention relates to a thermosetting alkoxysilyl compound, exhibiting excellent heat resistance properties in a composite, in particular, exhibiting a low coefficient of thermal expansion (CTE) and Tg-less, not exhibiting a glass transition temperature in a composite, a composition including the same, a cured product formed of the composition, a use of the cured product, and a method for preparing the alkoxysilyl compound.

BACKGROUND ART

The coefficient of thermal expansion of a thermosetting organic material is about 50 to 80 ppm/° C. and it is significant higher several to tens times than the CTE of a inorganic particles, that is ceramic material, or a metal, (for example, the CTE of silicon is 3 to 5 ppm/° C., while the CTE of copper is 17 ppm/° C.). Thus, when a thermosetting material is used together with an inorganic material or a metal in the fields of a semiconductor, a display, or the like, the properties and processability of a polymer material may be significantly limited due to the CTE-mismatch of the thermosetting material and the inorganic material or the metal. In addition, in a semiconductor packaging where a silicon wafer is adjacent to epoxy substrate or coated film in which an inorganic barrier layer is coated on the a polymer film to impart gas barrier properties, product defects such as crack formation in an inorganic layer, the warpage of a substrate, the peeling-off of a coating layer, the failure of a substrate, and the like, may occur due to a significant CTE-mismatch between constituent elements upon the changes of processing and/or service temperatures.

Because of the high CTE of the thermosetting material and the consequently the high dimensional change of the thermosetting material, the developments of next generation semiconductor substrates, printed circuit boards (PCBs), packaging, organic thin film transistors (OTFTs), and flexible display substrates and so on may be limited. Particularly, the current semiconductor and PCB industries have difficulties in the design, processing and securing of the reliability of the next generation components requiring high degrees of integration, miniaturization, flexibility, performance and so on, due to the epoxy materials with the much higher CTE than metal/ceramic materials. In other words, due to the high thermal expansion properties of the epoxy material at component processing temperatures, defects may be generated, processability may be limited, and the design of components and the securing of processability and reliability therein may be in difficulties. Accordingly, improved thermal expansion properties, that is dimensional stability of the epoxy are required in order to secure processability and reliability in electronic components.

In general, the making a composite of the epoxy compound with inorganic particles (an inorganic filler) and/or fibers has been used extensively, in order to improve thermal expansion properties (i.e., to obtain a low CTE) in a thermosetting epoxy compound. When the composite of the epoxy compound and the inorganic particles as the filler are formed in order to improve thermal expansion properties, a large amount of inorganic silica particles with a diameter of about 2 to 30 μm is required to be used to obtain a decreasing effect of CTE. However, due to the filling of the large amount of inorganic particles, the processability and physical properties of the parts may be deteriorated. That is, the presence of the large amount of inorganic particles may decrease fluidity, and voids may be generated during the filling of narrow spaces. In addition, the viscosity of the material may increase exponentially with the addition of the inorganic particles. Further, with the miniaturization of semiconductor structure, the decrease in fluidity (viscosity reduction) may be worsened since the size of the inorganic particles tends to decrease and the filler with a particle size of 1 μm or less is used. When inorganic particles with a large average diameter are used, the frequency of insufficient filling of a composition including a resin and the inorganic particles may increase. Even though the CTE may be largely decreased when a composition including an organic resin and a fiber as the filler is used, the CTE of composition may be still higher as compared to that of a silicon chip or the like.

As described above, the manufacturing of highly integrated and high performance electronic parts for next generation semiconductor substrates, PCBs, and the like may be restricted due to the limitations in the composite technology of the current epoxy compounds. Thus, the development of a novel compound having improved heat resistance properties—namely, a low CTE and Tg-less—is required to overcome a high CTE and consequently the insufficient thermal properties and processability of a common thermosetting polymer composite.

DISCLOSURE

Technical Problem

According to an embodiment of the present invention, there is provided a novel thermosetting alkoxysilyl compound, exhibiting excellent heat resistance properties, particularly a low CTE and Tg-less properties in a composite, and exhibiting excellent flame retardant properties in a cured product.

According to another embodiment of the present invention, there is provided a thermosetting alkoxysilyl composition, exhibiting excellent heat resistance properties, particularly a low CTE and Tg-less properties in a composite of an alkoxysilyl compound, and exhibiting excellent flame retardant properties in a cured product.

According to a further another embodiment of the present invention, there is provided a Tg-less cured product of an alkoxysilyl composition according to an embodiment, exhibiting excellent heat resistance properties, particularly a low CTE in a composite and exhibiting excellent flame retardant properties in a cured product due to the blending with an epoxy compound.

In addition, according to another embodiment of the present invention, there is provided a use of the thermosetting alkoxysilyl composition according to an embodiment of the present invention.

According to another embodiment of the present invention, there is provided a method for preparing a thermosetting alkoxysilyl compound.

Technical Solution

According to a first embodiment of the present invention, there is provided an alkoxysilyl compound having two or more alkoxysilyl groups and being selected from the group consisting of the following Formulae AI to II:

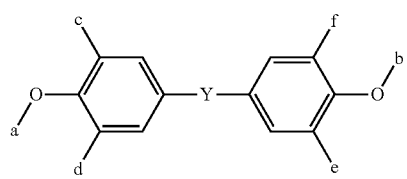
(AI)

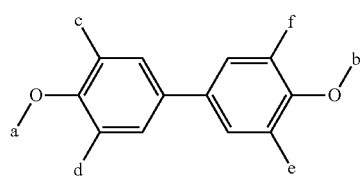
(BI)

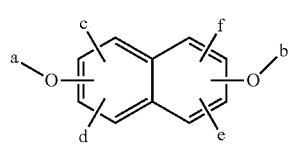
(CI)

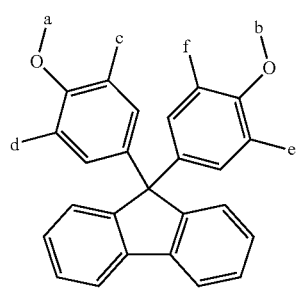
(DI)

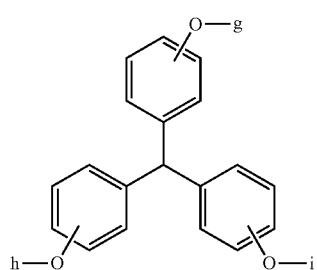
(EI)

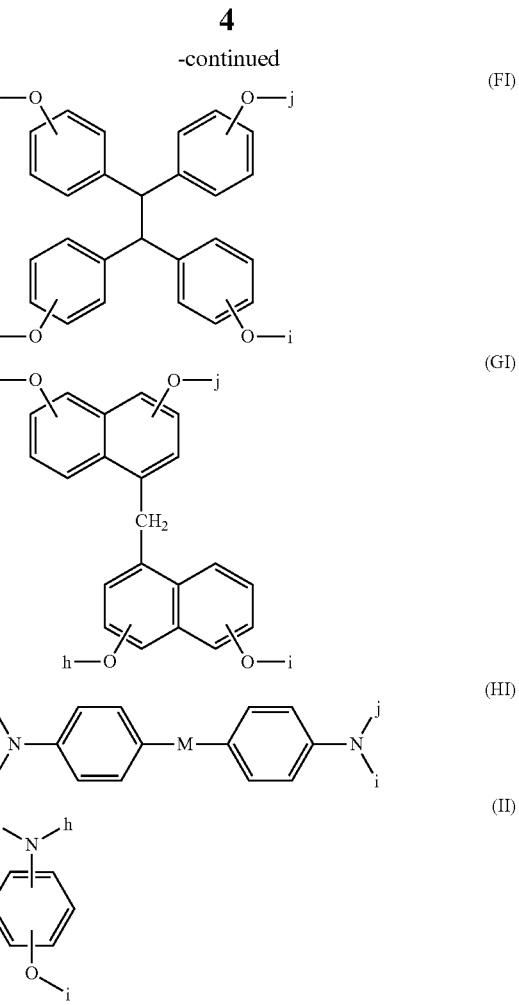

(in Formulae AI to DI, substituents a and b are each independently selected from the group consisting of the following Formulae S1 and S2, hydrogen, and a $C_{1-10}$ alkenyl group, substituents c to f are each independently selected from the group consisting of the following Formula S1, hydrogen, a $C_{1-10}$alkyl group, a $C_{1-10}$alkenyl group, and a $C_{6-30}$aryl group, and at least two substituents among a to f are selected from the group consisting of the following Formulae S1 and S2;

in Formula AI, Y may be —$CH_2$—, —$C(CH_3)_2$—, —$C(CF_3)_2$—, —S— or —$SO_2$—;

in Formulae EI to II, at least two substituents of g to j are selected from the group consisting of the following Formulae S1 and S2, and the remainder thereof may be hydrogen, a $C_{1-10}$alkyl group, a $C_{1-10}$alkenyl group, or a $C_{6-30}$aryl group;

in Formula HI, M is —$CH_2$—, —$C(CH_3)_2$—, —$C(CF_3)_2$—, —S— or —$SO_2$—; and a meta position of oxygen in the above Formula II may be substituted with a linear or branched $C_{1-10}$alkyl group)

—$(CH_2)_z$—$SiR_1R_2R_3$      [Formula S1]

—$CONH(CH_2)_z$—$SiR_1R_2R_3$      [Formula S2]

In Formulae S1 and S2, at least one of $R_1$ to $R_3$ is a linear or branched $C_{1-10}$ alkoxy group, the other thereof is a linear or branched $C_{1-10}$ alkyl group, and z is an integer of 3 to 10.

According to a second embodiment of the present invention, there is provided an alkoxysilyl compound selected from the group consisting of the above Formulae AI to DI, where at least one of substituents a and b is hydrogen, and at least two of substituents c to f are Formula S1.

According to a third embodiment of the present invention, there is provided an alkoxysilyl compound selected from the group consisting of the above Formulae EI to GI, where at least one of substituents g to j is hydrogen, and at least two of substituents g to j are selected from the group consisting of Formula S1 and Formula S2.

According to a fourth embodiment of the present invention, there is provided a composition of an alkoxysilyl compound according to any one of the first to third embodiments, wherein at least one alkoxysilyl compound according to the first embodiment is comprised.

According to a fifth embodiment of the present invention, there is provided a composition of an alkoxysilyl compound according to the fourth embodiment, further comprising at least one filler selected from the group consisting of inorganic particles and fibers.

According to a sixth embodiment of the present invention, there is provided a composition of an alkoxysilyl compound according to the fifth embodiment, wherein the inorganic particle is at least one selected from the group consisting of a metal oxide selected from the group consisting of silica, zirconia, titania, alumina, silicon nitride and aluminum nitride; T-10 type silsesquioxanes; ladder type silsesquioxanes; and cage type silsesquioxanes.

According to a seventh embodiment of the present invention, there is provided a composition of an alkoxysilyl compound according to the fifth embodiment, wherein an amount of the inorganic particles is from 5 wt % to 95 wt % based on a total solids content of the alkoxysilyl composition.

According to an eighth embodiment of the present invention, there is provided a composition of an alkoxysilyl compound according to the fifth embodiment, wherein an amount of the inorganic particles is from 30 wt % to 95 wt % based on a total solids content of the alkoxysilyl composition.

According to a ninth embodiment of the present invention, there is provided a composition of an alkoxysilyl compound according to the fifth embodiment, wherein an amount of the inorganic particles is from 5 wt % to 60 wt % based on a total solids content of the alkoxysilyl composition.

According to a tenth embodiment of the present invention, there is provided a composition of an alkoxysilyl compound according to the fifth embodiment, wherein the fiber is at least one selected from the group consisting of a glass fiber selected from the group consisting of an E-glass fiber, a T-glass fiber, an S-glass fiber, an NE-glass fiber, an H-glass fiber and quartz, and an organic fiber selected from the group consisting of a liquid crystal polyester fiber, a polyethyleneterephthalate fiber, a wholly aromatic fiber, a polyoxybenzoxasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber.

According to an eleventh embodiment of the present invention, there is provided a composition of an alkoxysilyl compound according to the fifth embodiment, wherein an amount of the fiber is from 10 wt % to 90 wt % based on a total solids content of the alkoxysilyl composition.

According to a twelfth embodiment of the present invention, there is provided a composition of an alkoxysilyl compound according to the fifth embodiment, further comprising the inorganic particles in the case in which the fiber is comprised therein.

According to a thirteenth embodiment of the present invention, there is provided a composition of an alkoxysilyl compound, comprising an alkoxysilyl compound according to any one of the first to third embodiments, and an epoxy compound.

According to a fourteenth embodiment of the present invention, there is provided a composition of an alkoxysilyl compound according to the thirteenth embodiment, wherein the epoxy compound is at least one selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

According to a fifteenth embodiment of the present invention, there is provided a composition of an alkoxysilyl compound according to the fourteenth embodiment, wherein the epoxy compound comprises bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, cyclo aliphatic compounds, or a novolac unit, as a core structure.

According to a sixteenth embodiment of the present invention, there is provided a composition of an alkoxysilyl compound according to the thirteenth embodiment, wherein the composition of an alkoxysilyl compound comprises an alkoxysilyl compound selected from the group consisting of the following Formulae AI to CI, and an epoxy compound:

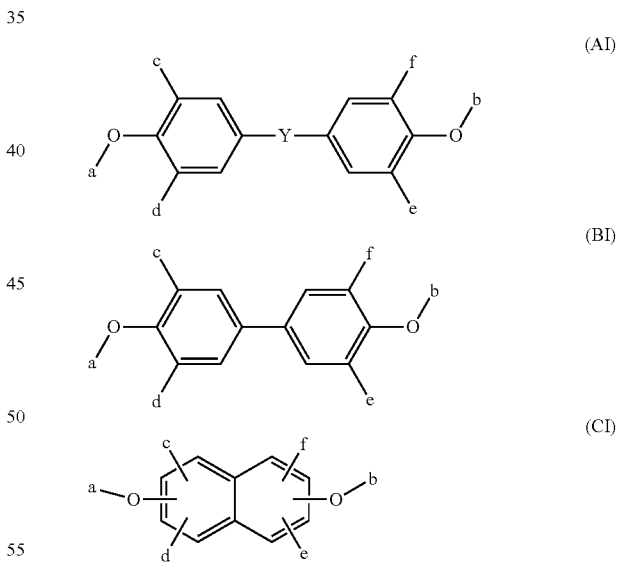

In which, Y is —CH$_2$— or —C(CH$_3$)$_2$—,
c to f are hydrogen, and
a and b are each independently selected from the group consisting of the following Formulae S1 and S2:

—(CH$_2$)$_z$—SiR$_1$R$_2$R$_3$     [Formula S1]

—CONH(CH$_2$)$_z$—SiR$_1$R$_2$R$_3$     [Formula S2]

In Formulae S1 and S2, R$_1$ to R$_3$ are a C$_{1-2}$alkoxy group, and z is an integer of 3 to 10.

According to a seventeenth embodiment of the present invention, there is provided a composition of an alkoxysilyl compound according to the thirteenth embodiment, wherein the composition of an alkoxysilyl compound comprises an alkoxysilyl compound selected from the group consisting of the following Formulae AI to CI, and an epoxy compound:

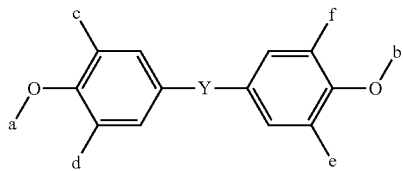
(AI)

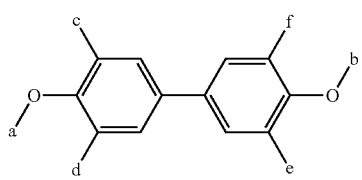
(BI)

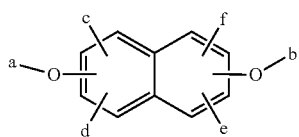
(CI)

In which, Y is —CH$_2$— or —C(CH$_3$)$_2$—, a and b are hydrogen, and at least two of c to f are the following Formula S1:

—(CH$_2$)$_z$—SiR$_1$R$_2$R$_3$ [Formula S1]

In Formula S1, R$_1$ to R$_3$ are a C$_{1-2}$alkoxy group, and z is an integer of 3 to 10.

According to an eighteenth embodiment of the present invention, there is provided a composition of an alkoxysilyl compound according to the thirteenth embodiment, wherein the composition of an alkoxysilyl compound comprises an alkoxysilyl compound selected from the group consisting of the following Formulae EI to GI, and an epoxy compound:

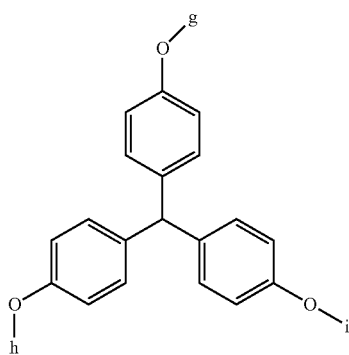
EI

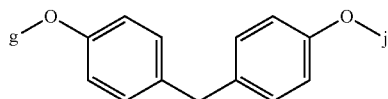
FI

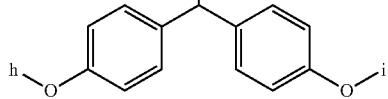
GI

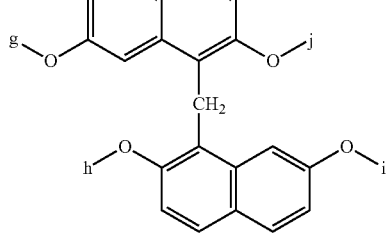

In which, at least one of g to j is hydrogen, and at least two of g to j are selected from the group consisting of the following Formula S1 and Formula S2:

—(CH$_2$)$_z$—SiR$_1$R$_2$R$_3$ [Formula S1]

In Formula S1, R$_1$ to R$_3$ are a linear or branched C$_{1-4}$alkoxy group, and z is an integer of 3 to 10.

—CONH(CH$_2$)$_z$—SiR$_1$R$_2$R$_3$ [Formula S2]

In Formula S2, at least one of R$_1$ to R$_3$ is a linear or branched C$_{1-10}$ alkoxy group, the other thereof is a linear or branched C$_{1-10}$ alkyl group, and z is an integer of 3 to 10.

According to a nineteenth embodiment of the present invention, there is provided a composition of an alkoxysilyl compound according to the thirteenth embodiment, wherein a molar ratio of an alkoxy group of the alkoxysilyl compound to an epoxy group of the epoxy compound is 0.1-10:1.

According to a twentieth embodiment of the present invention, there is provided a composition of an alkoxysilyl compound according to the thirteenth embodiment, wherein a molar ratio of an alkoxy group of the alkoxysilyl compound to an epoxy group of the epoxy compound is 0.2-1:1.

According to a twenty-first embodiment of the present invention, there is provided a composition of an alkoxysilyl compound according to the thirteenth embodiment, further comprising a curing agent.

According to a twenty-second embodiment of the present invention, there is provided an electronic material comprising the composition of an alkoxysilyl compound according to any one of the fourth to twenty-first embodiments.

According to a twenty-third embodiment of the present invention, there is provided a substrate comprising the composition of an alkoxysilyl compound according to any one of the fourth to twenty-first embodiments.

According to a twenty-fourth embodiment of the present invention, there is provided a film comprising the composition of an alkoxysilyl compound according to any one of the fourth to twenty-first embodiments.

According to a twenty-fifth embodiment of the present invention, there is provided a laminated plate comprising a metal layer placed on a base layer formed by using the composition of an alkoxysilyl compound according to any one of the fourth to twenty-first embodiments.

According to a twenty-sixth embodiment of the present invention, there is provided a printed circuit board comprising the laminated plate according to the twenty-fifth embodiment.

According to a twenty-seventh embodiment of the present invention, there is provided a semiconductor device comprising the printed circuit board according to the twenty-sixth embodiment.

According to a twenty-eighth embodiment of the present invention, there is provided a semiconductor packaging material comprising the composition of an alkoxysilyl compound according to any one of the fourth to twenty-first embodiments.

According to a twenty-ninth embodiment of the present invention, there is provided a semiconductor device comprising the semiconductor packaging material according to the twenty-eighth embodiment.

According to a thirtieth embodiment of the present invention, there is provided an adhesive comprising the composition of an alkoxysilyl compound according to any one of the fourth to twenty-first embodiments.

According to a thirty-first embodiment of the present invention, there is provided a paint comprising the composition of an alkoxysilyl compound according to any one of the fourth to twenty-first embodiments.

According to a thirty-second embodiment of the present invention, there is provided a composite material comprising the composition of an alkoxysilyl compound according to any one of the fourth to twenty-first embodiments.

According to a thirty-third embodiment of the present invention, there is provided a prepreg comprising the composition of an alkoxysilyl compound according to any one of the fourth to twenty-first embodiments.

According to a thirty-fourth embodiment of the present invention, there is provided a laminated plate comprising a metal layer placed on the prepreg according to the thirty-third embodiment.

According to a thirty-fifth embodiment of the present invention, there is provided a cured product of the composition of an alkoxysilyl compound according to any one of the fourth to twenty-first embodiments.

According to a thirty-sixth embodiment of the present invention, there is provided a cured product according to the thirty-fifth embodiment, wherein the cured product has a coefficient of thermal expansion of 100 ppm/° C. or less.

According to a thirty-seventh embodiment of the present invention, there is provided a cured product according to the thirty-sixth embodiment, wherein the cured product has a glass transition temperature of greater than 80° C., or does not show the glass transition temperature.

According to a thirty-eighth embodiment of the present invention, there is provided a method for preparing an alkoxysilyl compound for obtaining one final product among the following Formulae AI to II comprising reacting one starting material among the following Formulae AS to IS and an isocyanate-based alkoxysilane of the following Formula M1 in the presence of an optional base and an optional solvent:

[Starting Materials]

(in Formulae AS to DS, substituents k and l are each independently hydrogen, m to p

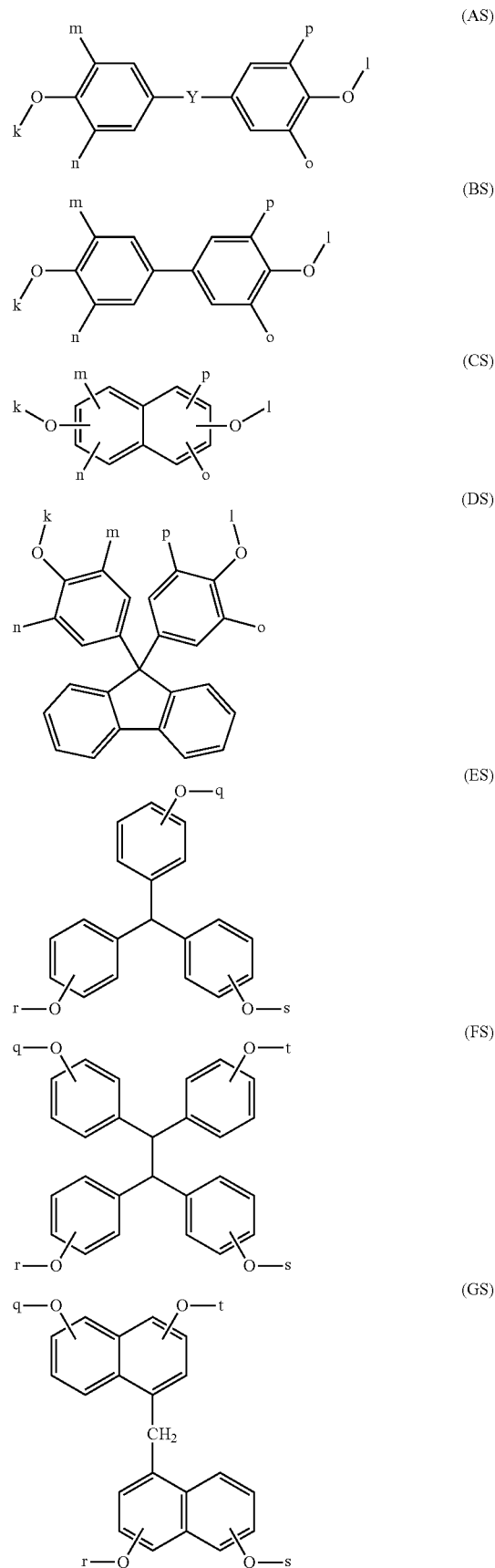

-continued

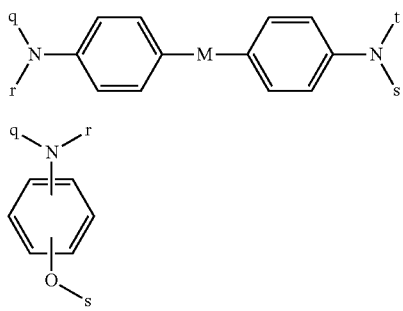

are each independently selected from the group consisting of hydrogen, a $C_{1-10}$alkyl group, a $C_{1-10}$alkenyl group, and a $C_{6-30}$aryl group, in Formula AS, Y is —$CH_2$—, —$C(CH_3)_2$—, —$C(CF_3)_2$—, —S—, or —$SO_2$—, in Formulae ES to IS, at least two substituents of q to t are hydrogen, and the remainder thereof may be each independently selected from a $C_{1-10}$alkyl group, a $C_{1-10}$alkenyl group, and a $C_{6-30}$aryl group, in Formula HS, M is —$CH_2$—, —$C(CH_3)_2$—, —$C(CF_3)_2$—, —S—, or —$SO_2$—, and a meta position of oxygen in Formula IS may be substituted with a linear or branched $C_{1-10}$alkyl group)

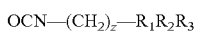 [Formula M1]

(where at least one of $R_1$ to $R_3$ is a linear or branched $C_{1-10}$alkoxy, the other thereof is a linear or branched $C_{1-10}$alkyl, and z is an integer of 3 to 10),

[Final Products]

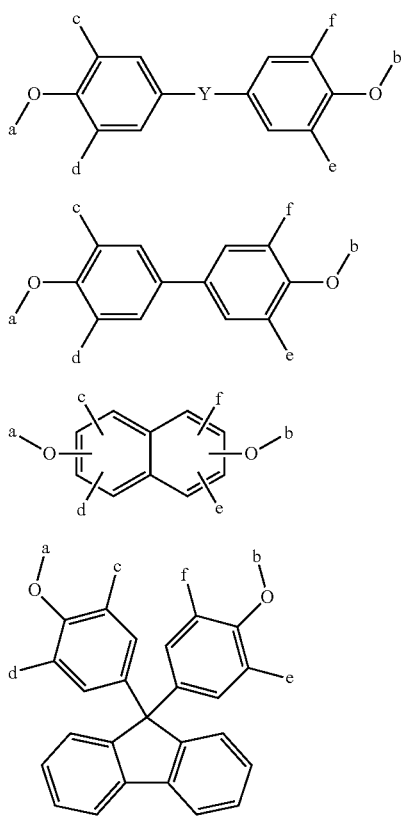

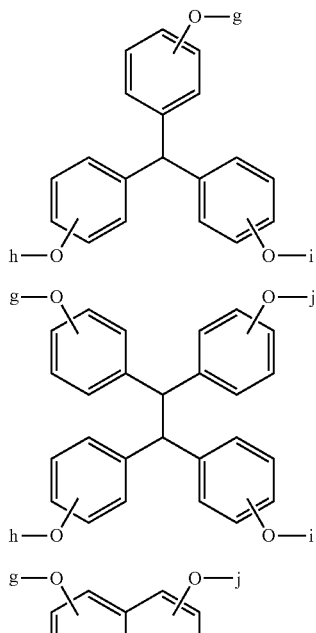

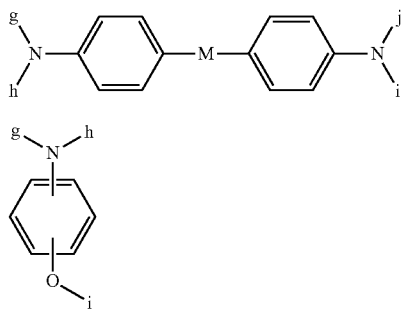

(in Formulae AI to DI, substituents a and b are each independently the following Formula S2, and substituents c to f are each independently selected from the group consisting of hydrogen, a $C_{1-10}$alkyl group, a $C_{1-10}$alkenyl group, and a $C_{6-30}$aryl group, in Formula AI, Y is —$CH_2$—, —$C(CH_3)_2$—, —$C(CF_3)_2$—, —S— or —$SO_2$—, in Formulae EI to II, at least two substituents of g to j are the following Formula S2, and the remainder thereof may be selected from the group consisting of hydrogen, a $C_{1-10}$alkyl group, a $C_{1-10}$alkenyl group, and a $C_{6-30}$aryl group, in Formula HI, M is —$CH_2$—, —$C(CH_3)_2$—, —$C(CF_3)_2$—, —S— or —$SO_2$—, and a meta position of oxygen in the above Formula II may be substituted with a linear or branched $C_{1-10}$alkyl group)

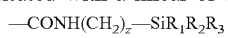 [Formula S2]

(in Formula S2, at least one of $R_1$ to $R_3$ is a linear or branched $C_{1-10}$ alkoxy group, the other thereof is a linear or branched $C_{1-10}$ alkyl group, and z is an integer of 3 to 10).

According to a thirty-ninth embodiment of the present invention, there is provided a method for preparing an alkoxysilyl compound according to the thirty-eighth embodiment, wherein the reaction is performed by reacting 0.1 to 5 equivalents of the isocyanate-based alkoxysilane of the above Formula M1 based on 1 equivalent of a hydroxyl group of one starting material among AS to IS.

According to a fortieth embodiment of the present invention, there is provided a method for preparing an alkoxysilyl compound according to the thirty-eighth embodiment, wherein the reaction is performed at a temperature of 15° C. to 120° C. for 1 to 72 hours.

According to a forty-first embodiment of the present invention, there is provided a method for preparing an alkoxysilyl compound comprising 1-1$^{st}$ step of reacting one starting material among the following Formulae AS to IS and an alkenyl compound of the following Formula M2 in the presence of an optional base and an optional solvent to obtain one intermediate (1) among the following Formulae A1 to I1; and 1-2$^{nd}$ step of reacting the intermediate (1) and an alkoxysilane of the following Formula M3 in the presence of a metal catalyst and an optional solvent to obtain one final product among the following Formulae AI to II:

[Starting Materials]

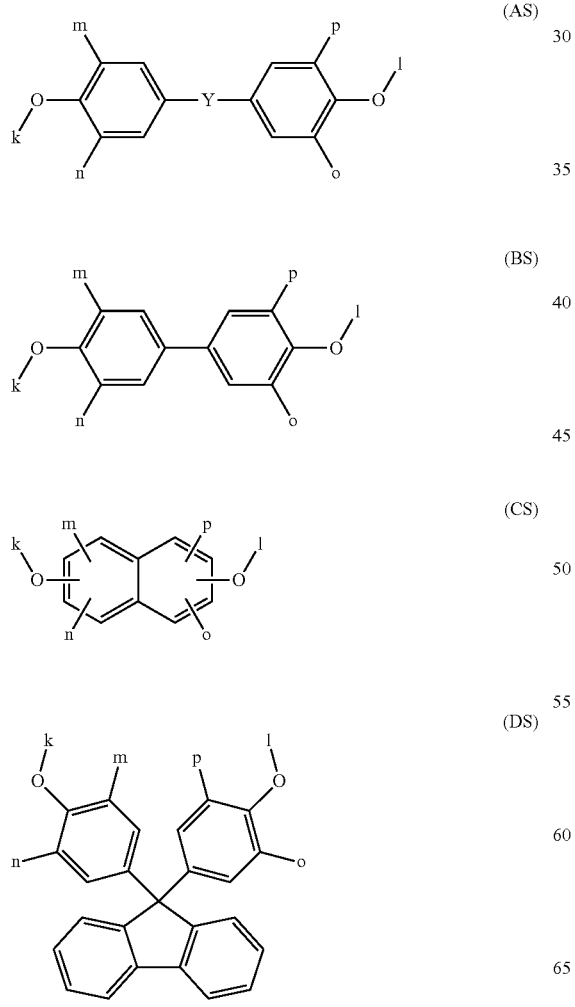

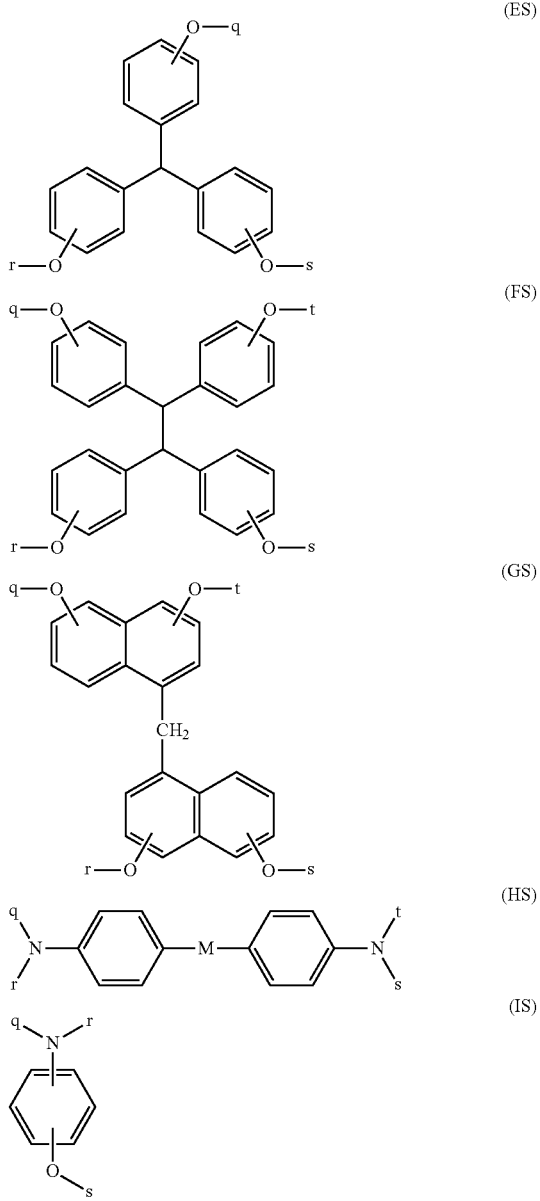

(in Formulae AS to DS, substituents k and l are each independently hydrogen, m to p are each independently selected from the group consisting of hydrogen, a $C_{1-10}$alkyl group, a $C_{1-10}$alkenyl group, and a $C_{6-30}$aryl group, in Formula AS, Y is —CH$_2$—, —C(CH$_3$)$_2$—, —C(CF$_3$)$_2$—, —S—, or —SO$_2$—, in Formulae ES to IS, at least two substituents of q to t are hydrogen, and the remainder thereof may be each independently selected from the group consisting of a $C_{1-10}$alkyl group, a $C_{1-10}$alkenyl group, and a $C_{6-30}$aryl group, in Formula HS, M is —CH$_2$—, —C(CH$_3$)$_2$—, —C(CF$_3$)$_2$—, —S—, or —SO$_2$—, and a meta position of oxygen in Formula IS may be substituted with a linear or branched $C_{1-10}$alkyl group)

$$X—(CH_2)_{z-2}—CH=CH_2 \qquad \text{[Formula M2]}$$

(in Formula M2, X is Cl, Br, I, —O—SO$_2$—CH$_3$, —O—SO$_2$—CF$_3$, —O—SO$_2$—C$_6$H$_4$—CF$_3$, —O—SO$_2$—C$_6$H$_4$—NO$_2$ or —O—SO$_2$—C$_6$H$_4$—CH$_3$, and z is an integer of 3 to 10),

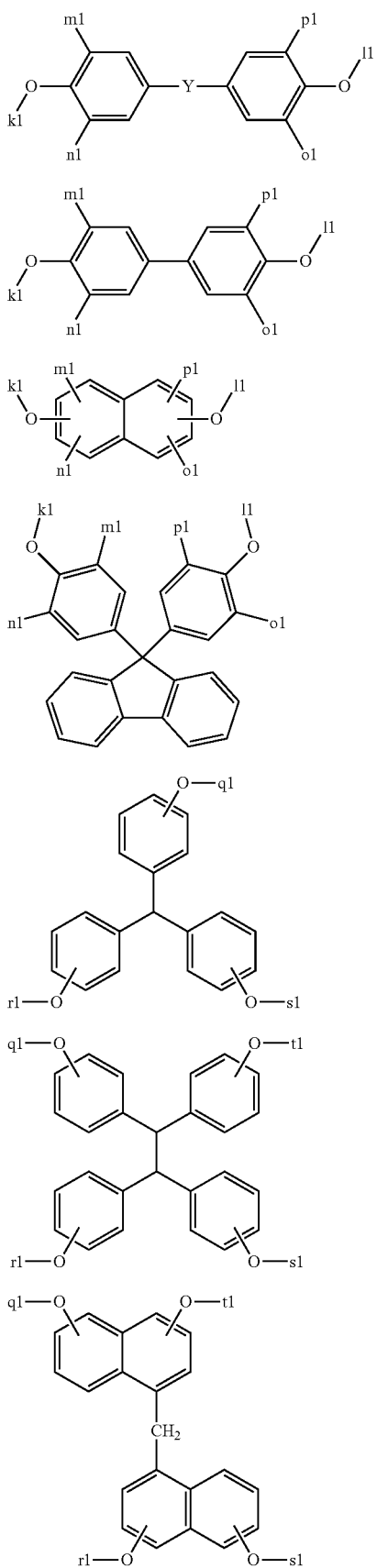

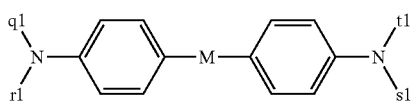

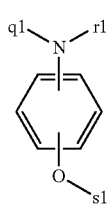

[Intermediates (1)]

(in Formulae A1 to D1, substituents k1 and l1 are each independently —(CH$_2$)$_{Z-2}$CH=CH$_2$ (z is an integer of 3 to 10), substituents m1 to p1 are each independently selected from the group consisting of hydrogen, alkyl, alkenyl and aryl, in Formula A1, Y is —CH$_2$—, —C(CH$_3$)$_2$—, —C(CF$_3$)$_2$—, —S—, or —SO$_2$—, in Formulae E1 to I1, at least two substituents of q1 to t1 are —(CH$_2$)$_{Z-2}$CH=CH$_2$ (z is an integer of 3 to 10), and the remainder thereof may be each independently selected from the group consisting of hydrogen, alkyl, alkenyl and aryl, in Formula H1, M is —CH$_2$—, —C(CH$_3$)$_2$—, —C(CF$_3$)$_2$—, —S—, or —SO$_2$—, and a meta position of oxygen in Formula I1 may be substituted with a linear or branched C$_{1-10}$alkyl group), HSiR$_1$R$_2$R$_3$  [Formula M3]

(in Formula M3, at least one of R$_1$ to R$_3$ is a linear or branched C$_{1-10}$ alkoxy group, and the other thereof is each independently a linear or branched C$_{1-10}$ alkyl group)

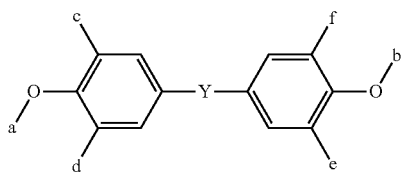

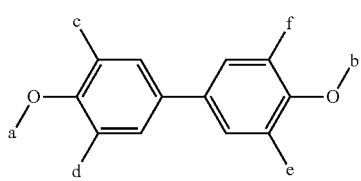

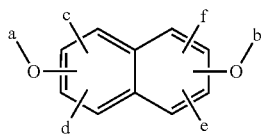

in Formulae EI to II, at least two substituents of g to j are the following Formula S1, and the remainder thereof may be each independently selected from the group consisting of hydrogen, a $C_{1-10}$alkyl group, a $C_{1-10}$alkenyl group, and a $C_{6-30}$aryl group, in Formula HI, M is —$CH_2$—, —$C(CH_3)_2$—, —$C(CF_3)_2$—, —S— or —$SO_2$—, and a meta position of oxygen in the above Formula II may be substituted with a linear or branched $C_{1-10}$alkyl group)

$$—(CH_2)_z—SiR_1R_2R_3 \qquad \text{[Formula S1]}$$

(in Formula S1, at least one of $R_1$ to $R_3$ is a linear or branched $C_{1-10}$ alkoxy group, the other thereof is a linear or branched $C_{1-10}$ alkyl group, and z is an integer of 3 to 10).

According to a forty-second embodiment of the present invention, there is provided a method for preparing an alkoxysilyl compound according to the forty-first embodiment, wherein the 1-1$^{st}$ step is performed by reacting 0.5 to 10 equivalents of —$(CH_2)_{z-2}CH=CH_2$ (z is an integer of 3 to 10) of the alkenyl compound of Formula M2 based on 1 equivalent of a hydroxyl group of the starting materials.

According to a forty-third embodiment of the present invention, there is provided a method for preparing an alkoxysilyl compound according to the forty-first embodiment, wherein the 1-1$^{st}$ step is performed at 15° C. to 100° C. for 1 to 120 hours.

According to a forty-fourth embodiment of the present invention, there is provided a method for preparing an alkoxysilyl compound according to the forty-first embodiment, wherein the 1-2$^{nd}$ step is performed by reacting 1 to 5 equivalents of the alkoxysilane of Formula M3 based on 1 equivalent of the alkenyl group of the intermediate (1).

According to a forty-fifth embodiment of the present invention, there is provided a method for preparing an alkoxysilyl compound according to the forty-first embodiment, wherein the 1-2$^{nd}$ step is performed at 15° C. to 120° C. for 1 to 72 hours.

(in Formulae AI to DI, substituents a and b may be the following Formula S1 or S2; hydrogen; or alkenyl, and substituents c to f may be Formula S1, hydrogen, alkyl, alkenyl, or aryl, in Formula AI, Y may be —$CH_2$—, —$C(CH_3)_2$—, —$C(CF_3)_2$—, —S— or —$SO_2$—, in Formulae EI to II, at least two substituents of g to j may be the following Formula S1 or S2; the remainder thereof may be hydrogen, alkyl, alkenyl, or aryl, in Formula HI, M is —$CH_2$—, —$C(CH_3)_2$—, —$C(CF_3)_2$—, —S— or —$SO_2$—, and a meta position of oxygen in the above Formula II may be substituted with a linear or branched $C_{1-10}$alkyl group)

$$—(CH_2)_z—SiR_1R_2R_3 \qquad \text{[Formula S1]}$$

$$—CONH(CH_2)_z—SiR_1R_2R_3 \qquad \text{[Formula S2]}$$

(in Formulae S1 and S2, at least one of $R_1$ to $R_3$ is a $C_{1-10}$ alkoxy group, the other thereof is a $C_{1-10}$ alkyl group, the alkyl group and the alkoxy group are linear or branched, and z is an integer of 3 to 10)

Advantageous Effects

A thermosetting alkoxysilyl composition including a novel alkoxysilyl compound according to the present invention shows improved heat resistance properties in a composite, i.e., the decrease of CTE and disappearance of glass transition temperature (hereinafter Tg-less) of the composition of the alkoxysilyl compound. Further, a cured product

[Final Products]

(in Formulae AI to DI, substituents a and b are the following Formula S1, and substituents c to f are each independently selected from the group consisting of Formula S1, hydrogen, —OH, a $C_{1-10}$alkyl group, a $C_{1-10}$alkenyl group, and a $C_{6-30}$aryl group, in Formula AI, Y is —$CH_2$—, —$C(CH_3)_2$—, —$C(CF_3)_2$—, —S— or —$SO_2$—, including the alkoxysilyl compound according to the present invention shows excellent flame retardant properties due to an alkoxysilyl group.

BRIEF DESCRIPTION OF DRAWINGS

FIG. 1 is a graph illustrating dimensional changes with the variation of temperature for Example 34 and Comparative Example 1;

FIG. 2 is a graph illustrating dimensional changes with the variation of temperature for Example 1 and Comparative Example 1;

FIG. 3 is a graph illustrating dimensional changes with the variation of temperature for Example 46; and FIGS. 4A and 4B illustrate photographic images of combusted composites strips according to Example 1 and Comparative Example 1.

BEST MODE FOR INVENTION

Preferred embodiments of the present invention will be described below with reference to the accompanying drawings. The present invention may, however, be embodied in different forms and should not be construed as being limited to the embodiments set forth herein. In addition, these embodiments of the present invention are provided so as to more completely explain the present invention to a person having average knowledge in the art.

The present invention provides a novel thermosetting alkoxysilyl compound, where a composite obtained by curing the composition of the alkoxysilyl compound exhibits improved heat resistance properties, particularly a low CTE and Tg-less and/or a cured product thereof exhibits good flame retardant properties, an alkoxysilyl composition including the same, a cured product formed by using the composition, a use of the composition, and a method for preparing the alkoxysilyl compound.

In the present invention, "composite" refers to a cured product of a composition including an alkoxysilyl compound and a filler (fiber and/or particles). In the present invention, "cured product" refers to a cured product of a composition including an alkoxysilyl compound, and refers to a cured product of a composition including any alkoxysilyl compound, together with optionally at least one selected from the group consisting of a curing catalyst, a filler, an epoxy compound, a curing agent, a curing catalyst and other additives. In addition, the cured product is also used to denote a partially cured product. Generally, only a cured product reinforced with inorganic particles or a fiber is referred to as a composite. Thus, the cured product has a broader meaning than the composite. However, the cured product reinforced with the inorganic particles or the fiber may be considered to have the same meaning as the composite.

Hereinafter, a thermosetting alkoxysilyl compound, a composition including the same, a cured product thereof, a use thereof, and a method of preparing the alkoxysilyl compound, provided in example embodiments of the present invention will be described in detail.

1. Alkoxysilyl Compound

According to an embodiment of the present invention, an alkoxysilyl compound selected from the group consisting of the following Formulae AI to II, and having two or more alkoxysilyl groups is provided.

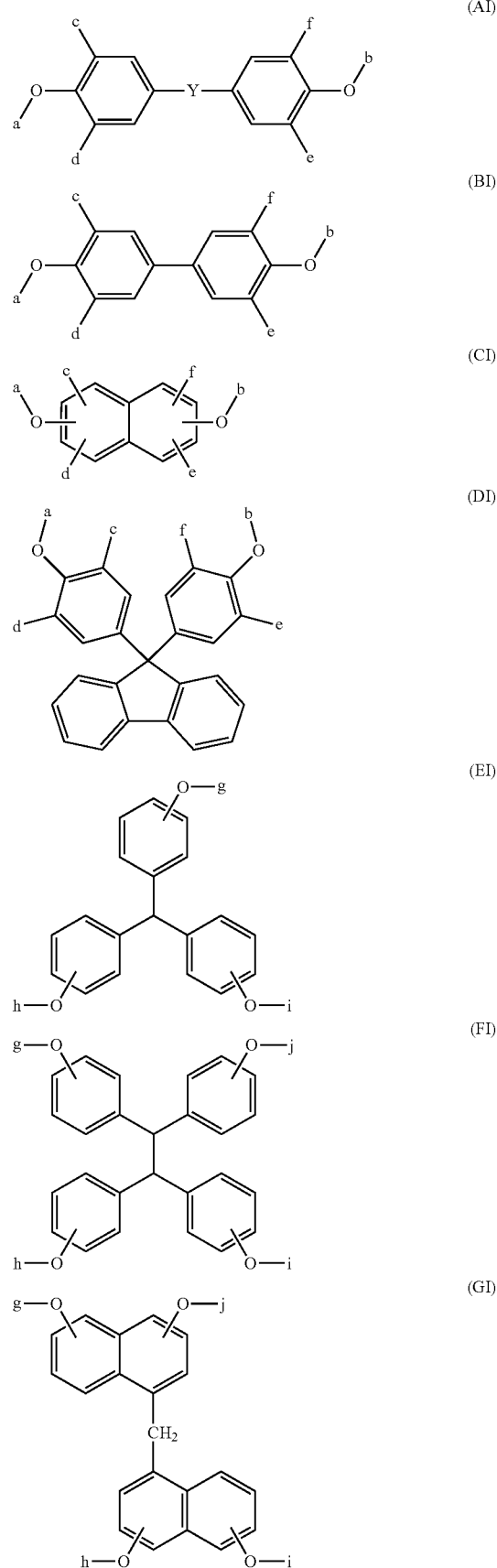

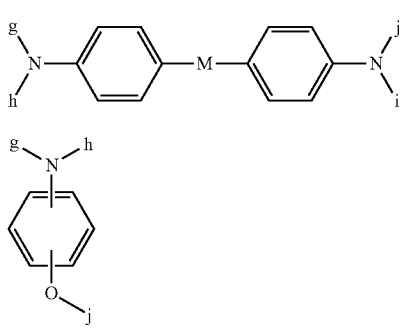

In Formulae AI to DI, substituents a and b are each independently selected from the group consisting of the following Formulae S1 and S2, hydrogen, and a $C_{1-10}$alkenyl group, substituents c to f are each independently selected from the group consisting of the following Formula S1, hydrogen, a $C_{1-10}$alkyl group, a $C_{1-10}$alkenyl group, and a $C_{6-30}$aryl group, and at least two substituents among a to f are selected from the group consisting of the following Formulae S1 and S2;

in Formula AI, Y may be —CH$_2$—, —C(CH$_3$)$_2$—, —C(CF$_3$)$_2$—, —S— or —SO$_2$—;

in Formulae EI to II, at least two of substituents g to j are selected from the group consisting of the following Formulae S1 and S2, and the remainder thereof may be hydrogen, a $C_{1-10}$alkyl group, a $C_{1-10}$alkenyl group, or a $C_{6-30}$aryl group;

in Formula HI, M is —CH$_2$—, —C(CH$_3$)$_2$—, —C(CF$_3$)$_2$—, —S— or —SO$_2$—; and a meta position of oxygen in the above Formula II may be substituted with a linear or branched $C_{1-10}$alkyl group:

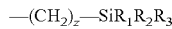  [Formula S1]

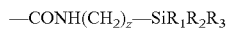  [Formula S2]

In Formulae S1 and S2, at least one of $R_1$ to $R_3$ is a linear or branched $C_{1-10}$ alkoxy group, the other thereof is a linear or branched $C_{1-10}$ alkyl group, and z is an integer of 3 to 10. More preferably, at least one of $R_1$ to $R_3$ is a linear or branched $C_{1-3}$alkoxy group, and further more preferably, at least one of R1 to R3 is a linear or branched C1-2alkoxy group.

The term "alkoxy" used in the present disclosure refers to a monovalent —OR (R is alkyl) group which may be a linear chain or a branched chain, cyclic or acyclic, and may or may not include a heteroatom such as N, O, S and P.

The term "alkyl" used in the present disclosure refers to a monovalent $C_{1-10}$hydrocarbon group which may be a linear chain or a branched chain, cyclic or acyclic, and may or may not include a heteroatom such as N, O, S and P.

The term "alkenyl" used in the present disclosure refers to alkyl having at least one carbon-carbon double bond, and may be a linear chain or a branched chain, cyclic or acyclic, and may or may not include a heteroatom such as N, O, S and P. The carbon number of the alkenyl may be C3-C10, and —(CH$_2$)$_{Z-2}$CH=CH$_2$ (Z is an integer of 3 to 10), which will be described later may be included in the alkenyl, without specific limitation.

The term "aryl" used in the present disclosure refers to a residual group of an aromatic hydrocarbon in which one hydrogen atom is removed from the core thereof. The carbon number of the aryl may be C6-C30, for example, C6-C15, without specific limitation, and the aryl may be monocyclic or polycyclic.

Specific alkoxysilyl compound according to the present invention may be, for example, selected from the group consisting of Formulae AI to DI, at least one of substituents a and b may be hydrogen, and at least two of substituents c to f may be alkoxysilyl compounds of Formula S1.

Another example embodiment of the specific alkoxysilyl compound according to the present invention may be selected from the group consisting of Formulae EI to GI, at least one of substituents g to j is hydrogen, and at least two thereof may be selected from the group consisting of Formula S1 and Formula S2.

2. Composition of Alkoxysilyl Compound

According to another embodiment of the present invention, a composition including at least one alkoxysilyl compound selected from the group consisting of Formulae AI to II according to any example embodiments of the present invention is provided.

Any compositions provided in the present invention may be used in various uses such as an electronic material, for example, a semiconductor substrate, an encapsulating material (packaging material), a film, an electronic part such as a printed circuit board, an adhesive, a paint, a composite material, or the like, without limitation. In addition, any compositions provided in the present invention may be a curable composition and/or a curable composition including an inorganic material.

In the conventional technique, an alkoxysilyl compound is used for surface treating agent of inorganic particles, additives, the preparation of a silica or organic-inorganic hybrid via sol-gel reaction. However, the alkoxysilyl compound of the present invention may be differentiated from the conventional technique as it is used as a thermosetting binder. That is, the alkoxysilyl compound of the present invention included in such a composition acts as a thermally curable monomer or a binder, and a reaction may be performed by an imidazole curing agent or a novolac curing agent during curing, without limitation.

The composition of an alkoxysilyl compound is understood to have the meaning of a composition of an alkoxysilyl compound including, as an alkoxysilyl compound, at least one type of alkoxysilyl compound selected from the group consisting of Formulae AI to II (hereinafter an "alkoxysilyl compound of the present invention"), which are provided by any embodiments of the present invention. The kind and the mixing ratio of a catalyst, an inorganic material (filler) (for example, inorganic particles and/or a fiber), and other additives, which may be additionally included in the composition of an alkoxysilyl compound, are not limited.

Further, according to an embodiment of the present invention, a composition of an alkoxysilyl compound including at least one type of alkoxysilyl compound selected from the group consisting of Formulae AI to II, which are provided by any embodiments of the present invention, and an inorganic material (filler) (for example, inorganic particles and/or a fiber), is provided. The composite composition is understood to include a composition of an alkoxysilyl compound including at least one type of alkoxysilyl compound selected from the group consisting of Formulae AI to II and a filler, and the kind and the mixing ratio of a catalyst, an inorganic material (filler) (for example, inorganic particles and/or a fiber), and other additives, which may be additionally included in the composition of an alkoxysilyl compound, are not limited.

To the above composite composition and any types of composition according to example embodiments of the present invention, which will be explained later, inorganic particles as a filler of an inorganic material and/or a fiber may be additionally included.

Any inorganic particles generally known to be used to decrease the coefficient of thermal expansion of a organic resin may be used. Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxanes, ladder type silsesquioxanes, and cage type silsesquioxanes. The inorganic particles may be used alone or as a mixture of two or more thereof.

In the case in which a particularly large amount of the inorganic particles is filled, the fused silica is preferably used. The fused silica may have any shape among a cataclastic shape and a spherical shape. However, the spherical shape is preferable, in order to increase the mixing ratio of the fused silica and to restrain the increase of the fused viscosity of a forming material.

Inorganic particles having a particle size of 0.5 nm to several tens of μm (for example, from 50 μm to 100 μm) may be used, without limitation, in consideration of the use of a composite, particularly, the dispersibility of the inorganic particles, or the like. Since the inorganic particles are dispersed in an epoxy compound, and the dispersibility is different according to the particle size, the inorganic particles having the above-described size may preferably be used. In addition, the wide range of the inorganic particles size is used preferably increased to increase the mixing ratio of the inorganic particles.

In the composition of an alkoxysilyl compound in accordance with an embodiment of the present invention, the mixing amount of the inorganic particles with respect to the alkoxysilyl compound may be appropriately controlled in consideration of the CTE decrease of an alkoxysilyl composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total solids content of the alkoxysilyl composition.

More particularly, in an embodiment, when the composition of an alkoxysilyl compound is used as a semiconductor encapsulating agent, or the like, the amount of the inorganic particles may be, for example, 30 wt % to 95 wt %, for example, 30 wt % to 90 wt %, without limitation, based on the total solids content of the alkoxysilyl composition in consideration of the CTE value and material processability. In another embodiment, when the composition of an alkoxysilyl compound is used in a semiconductor substrate, the amount of the inorganic particles may be 5 wt % to 60 wt %, for example, 10 wt % to 50 wt % based on the total solids content of the composition of an alkoxysilyl compound in consideration of the CTE value and the intensity of the substrate.

Meanwhile, when a fiber is used as the inorganic material, any type and size of fiber commonly used in the technical field of a thermosetting resin may be used.

Any commonly used fibers for improving physical properties of a common organic resin cured product may be used without limitation. Particularly, a glass fiber, an organic fiber or a mixture thereof may be used. In addition, the term 'glass fiber' used in this disclosure may include a glass fiber fabric, a glass fiber nonwoven product, or the like, as well as the glass fiber. Examples of the glass fibers may include, without limitation, the glass fiber of an E-glass fiber, a T-glass fiber, an S-glass fiber, an NE-glass fiber, a D-glass fiber, a quartz glass fiber, or the like. For example, the glass fiber of E or T may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more thereof.

In the case in which the fiber is used as the filler in any compositions of an alkoxysilyl compound according to the present invention, the amount of the fiber in the composition of an alkoxysilyl compound may be 10 wt % to 90 wt %, for example, 30 wt % to 70 wt %, in addition, for example, 35 wt % to 65 wt % based on the total solids content of the composition of an alkoxysilyl compound. Meanwhile, in the composition of an alkoxysilyl compound including the fiber, when solid parts excluding the fiber from the total solids content is referred to as a resin component, the remaining amount other than the fiber in the composition of an alkoxysilyl compound including the fiber is the amount of the resin component. Thus, the resin content may be 10 wt % to 90 wt %, for example, 30 wt % to 70 wt %, in addition, for example, 35 wt % to 65 wt %. The amount of the fiber within the above-described range may be preferred in consideration of the increase in heat resistance and the processability aspect. The total solids content of the composition of an alkoxysilyl compound refers to the sum of the components constituting the composition of an alkoxysilyl compound excluding solvents and other liquid materials from the components constituting the composition of an alkoxysilyl compound.

Further, in the composition of an alkoxysilyl compound including the fiber may additionally include inorganic particles as occasion demands. In this case, the inorganic particles may be included in an amount of 1 wt % to 70 wt % in the composition, based on the total amount of the resin in consideration of the improvement of the physical properties and processability. In this case, the type of inorganic particles is not specifically limited, and any inorganic particles known in the art may be used. For example, the above-described inorganic particles may be used.

According to further another embodiment of the present invention, a composition of an alkoxysilyl compound including the alkoxysilyl compound of the present invention and an epoxy compound is provided, and in this technical field, the composition of an alkoxysilyl compound, the cured product and/or composite thereof may be used with various kinds of common epoxy compounds according to the application and/or use thereof. Thus, in the compositions of an alkoxysilyl compound according to any embodiments described above or later in the present invention, at least one type of alkoxysilyl compound selected from the group consisting of Formulae AI to II according to any embodiments of the present invention, and any kind of epoxy compounds commonly known in the art (hereinafter a 'common epoxy compound') may be included.

The common epoxy compounds may be any epoxy compounds commonly known in the art without limitation, and may be, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. Further, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including, as a core structure, bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, an aminophenol cyclo aliphatic compound, or a novolac unit.

For example, the common epoxy compound may be at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, a aliphatic polyglycidyl-based epoxy compound and an aliphatic glycidyl amine-based epoxy compound including, as a core structure, bisphenol A, bisphenol F, bisphenol S, biphenyl, naphthalene, or fluorene.

Any compositions of an alkoxysilyl compound in accordance with an embodiment of the present invention may include without limitation, based on the total amount of an alkoxysilyl compound, from 1 wt % to 99 wt % of the alkoxysilyl compound according to any embodiments of the present invention and from 1 wt % to 99 wt % of the common epoxy compound; for example, from 10 wt % to 90 wt % of the alkoxysilyl compound of the present invention and from 10 wt % to 90 wt % of the common epoxy compound; for example, from 30 wt % to 99 wt % of the alkoxysilyl compound of the present invention and from 1 wt % to 70 wt % of the common epoxy compound; for example, from 50 wt % to 99 wt % of the alkoxysilyl compound of the present invention and from 1 wt % to 50 wt % of the common epoxy compound; for example, from 10 wt % to below 100 wt % of the alkoxysilyl compound of the present invention and from in excess of 0 wt % to 90 wt % of the common epoxy compound; for example, from 30 wt % to below 100 wt % of the alkoxysilyl compound of the present invention and from in excess of 0 wt % to 70 wt % of the common epoxy compound; for example, from 50 wt % to below 100 wt % of the alkoxysilyl compound of the present invention and from in excess of 0 wt % to 50 wt % of the common epoxy compound.

More particularly, in the composition in which an epoxy compound is mixed, the molar ratio of the alkoxy group of the alkoxysilyl compound to the epoxy group of the epoxy compound may preferably be 0.1-10:1, and more preferably, 0.2-1:1. If the molar ratio of the alkoxy group of the alkoxysilyl compound is included in an amount of less than 0.1 moles per 1 mole of the epoxy group of the epoxy compound, the improving effect of heat resistance due to an alkoxysilyl compound may not be attained, and if the amount included is greater than 10 moles, the curing degree of a cured product including the epoxy group may be insufficient.

The composition of an alkoxysilyl compound including the epoxy compound may be, for example, a composition including an alkoxysilyl compound selected from the group consisting of the following Formulae AI to CI, and an epoxy compound.

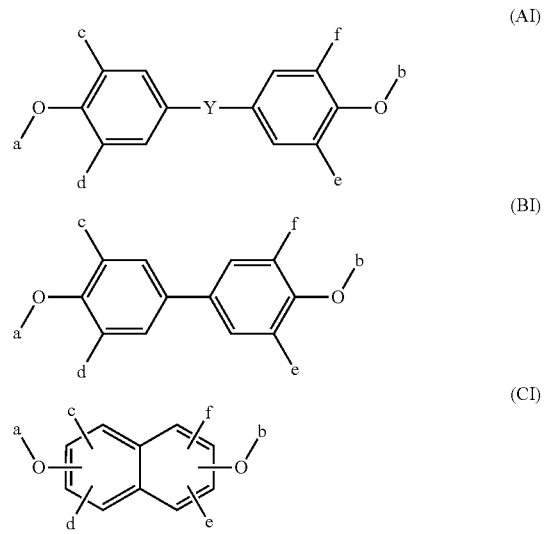

In which, Y is —CH$_2$— or —C(CH$_3$)$_2$—,
c to f are hydrogen, and
a and b are each independently selected from the group consisting of the following Formulae S1 and S2.

In Formulae S1 and S2, R$_1$ to R$_3$ are linear or branched C$_{1-2}$alkoxy, and z is an integer of 3 to 10.

Another particular embodiment of the composition of an alkoxysilyl compound is a composition including an alkoxysilyl compound selected from the group consisting of the following Formulae AI to CI, and an epoxy compound.

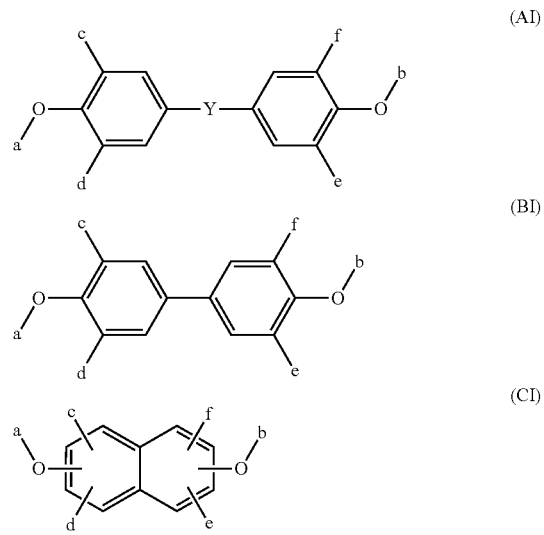

In which, Y is —CH$_2$— or —C(CH$_3$)$_2$—,
a and b are hydrogen, and
at least two of c to f are the following Formulae S1.

In Formula S1, R$_1$ to R$_3$ are C$_{1-2}$alkoxy, and z is an integer of 3 to 10. Another particular embodiment of the composition of an alkoxysilyl compound is a composition including an alkoxysilyl compound selected from the group consisting of the following Formulae EI to GI, and an epoxy compound.

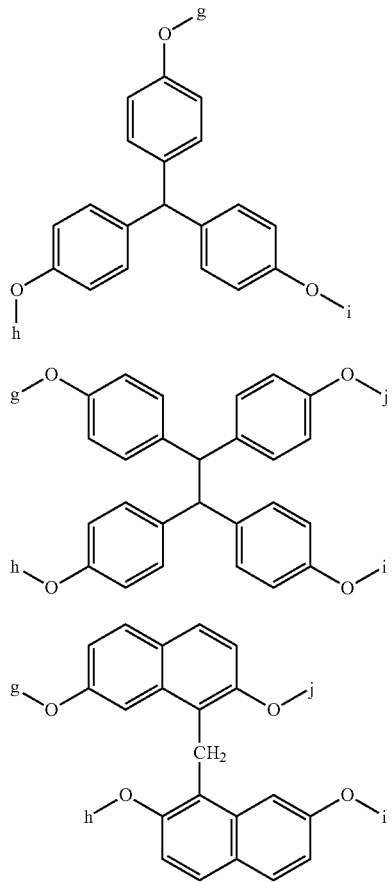

In this case, at least one of g to j is hydrogen, and at least two thereof are selected from the group consisting of the following Formula S1 and Formula S2.

—(CH$_2$)$_z$—SiR$_1$R$_2$R$_3$ [Formula S1]

In Formula S1, R$_1$ to R$_3$ are linear or branched C$_{1-4}$alkoxy, and z is an integer of 3 to 10.

—CONH(CH$_2$)$_z$—SiR$_1$R$_2$R$_3$ [Formula S2]

In Formula S2, at least one of R$_1$ to R$_3$ is linear or branched C$_{1-10}$alkoxy, the other thereof is linear or branched C$_{1-10}$alkyl, and z is an integer of 3 to 10.

The composition of an alkoxysilyl compound may further include a curing agent, and the curing agent may be any commonly known curing agents, without specific limitation. For example, imidazoles, amines, phenol resins, acid anhydrides, or the like may be used.

More particularly, an imidazole curing agent may include, without specific limitation, imidazoles such as 2-methylimidazole (2MZ), 2-undecylimidazole, 2-ethyl-4-methylimidazole (2E4M), 2-phenylimidazole, 1-(2-cyanoethyl)-2-alkyl imidazole, and 2-hepadecylimidazole (2HDI), and potential imidazoles.

An aliphatic amine, an alicyclic amine, an aromatic amine, other amines and a modified polyamine may be used as the amine curing agent without limitation. In addition, an amine compound including two or more primary amine groups may be used. Particular examples of the amine curing agent may include at least one aromatic amine selected from the group consisting of 4,4'-dimethylenedianiline (diamino diphenyl methane, DAM or DDM), and diamino diphenyl sulfone (DDS), and m-phenylene diamine, at least one aliphatic amine selected from the group consisting of diethylene triamine (DETA), diethylene tetraamine, triethylene tetraamine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl)methane, and larominc 260, other amines such as dicyanamide (DICY), or the like, and a modified amine such as a polyamide-based compound, an epoxide-based compound, or the like.

Examples of the phenol curing agent may include, without limitation, a phenol novolac resin, a cresol novolac resin, a bisphenol A novolac resin, a xylene novolac resin, a triphenyl novolac resin, a biphenyl novolac resin, a dicyclopentadiene-based novolac resin, phenol p-xylene, a naphthalene-based phenol novolac resin, a triazine-based compound, or the like.

Examples of the acid anhydride curing agent may include, without limitation, aliphatic acid anhydrides such as dodecenyl succinic anhydride (DDSA), poly azelaic poly anhydride, or the like, alicyclic acid anhydrides such as hexahydrophthalic anhydride (HHPA), methyl tetrahydrophthalic anhydride (MeTHPA), methylnadic anhydride (MNA), or the like, aromatic acid anhydrides such as trimellitic anhydride (TMA), pyromellitic acid dianhydride (PMDA), benzophenonetetracarboxylic dianhydride (BTDA), or the like, and halogen-based acid anhydrides such as tetrabromophthalic anhydride (TBPA), chlorendic anhydride, or the like.

According to the range of the target curing degree of a thermosetting composite, the amount of the curing agent may be controlled based on the concentration of the alkoxysilyl group of an alkoxysilyl compound. If an epoxy compound is additionally added to the composition, the amount of the curing agent may be controlled based on the concentration of the alkoxysilyl group and the epoxy group. For example, when an imidazole curing agent is used, 0.1 to 7 phr based on the weight of (alkoxysilyl compound+epoxy compound) is used, when a phenol curing agent is used, the amount of the curing agent is controlled to have an equivalent ratio of (alkoxysilyl group+epoxy) equivalent/phenol equivalent of 0.5 to 10, for example, 0.8 to 5.0 in an equivalent reaction of the phenol curing agent and the alkoxysilyl group, or the phenol curing agent and the alkoxysilyl group and the epoxy group.

Though the mixing amount of the curing agent has been explained with respect to the imidazole curing agent and the phenol curing agent, an amine curing agent, an acid anhydride curing agent and any curing agents for curing epoxy compounds not separately illustrated in this application but used for curing, may be used by appropriately mixing a stoichiometric amount according to the chemical reaction of the thermosetting functional group and a reactive functional group of the curing agent based on the concentration of the total alkoxysilyl group, or the alkoxysilyl group and the epoxy group in the alkoxysilyl composition according to the desired range of the curing degree. The above-described parts may be appropriately controlled by a person skilled in the art.

An optional curing accelerator (catalyst) may be additionally included as occasion demands to promote the curing reaction of the alkoxysilyl compound and an optionally added epoxy compound. Any curing accelerators (catalysts) commonly used for curing an epoxy composition in this field may be used without limitation, for example, an imidazole-based, a tertiary amine-based, a quaternary ammonium-based, an organic acid salt-based, a Lewis acid, a phosphor compound-based curing accelerator may be used.

More particularly, for example, an imidazole-based curing accelerator such as 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); a tertiary amine-based curing accelerator such as benzyldimethylamine (BDMA), tris dimethylaminomethyl phenol (DMP-30), and triethylenediamine; a quaternary ammonium salt curing accelerator such as tetrabutylammonium bromide, or the like; a curing accelerator of diazabicycloundecene (DBU), or DBU an organic acid salt; a phosphor compound-based curing accelerator such as triphenyl phosphine, phosphoric acid ester, or the like, and a Lewis acid curing accelerator such as $BF_3$-monoethylamine ($BF_3$-MEA), or the like, may be illustrated without limitation. Potential curing accelerators such as a micro capsule coated one or a chelate formed one may also be used as the curing accelerator. These compounds may be used alone or as a mixture of two or more thereof according to curing conditions.

The mixing amount of the curing accelerator may be a commonly applied mixing amount in this technical art without specific limitation. For example, 0.1 to 10 parts per hundred resin (phr, parts by weight based on 100 parts by weight of an epoxy compound), for example, 0.2 to 5 phr of the curing accelerator may be used, based on the epoxy compound. The above-described amount range of the curing accelerator may be preferably used in consideration of curing reaction accelerating effect and curing reaction rate control. Through using the above-described amount range of the curing accelerator, the curing may be rapidly achieved, and the improvement of working throughput may be expected.

In the composition of an alkoxysilyl compound, other additives such as a releasing agent, a surface treating agent, a flame retardant, a plasticizer, bactericides, a leveling agent, a defoaming agent, a colorant, a stabilizer, a coupling agent, a viscosity controlling agent, a diluent, or the like, which are commonly mixed additives, may be mixed, if necessary, within the range of undamaging the physical properties of the cured product of the composition.

As described above, the term "alkoxysilyl composition" used in the present disclosure is understood to include an alkoxysilyl compound of the present invention and other components if necessary, for example, a catalyst, an inorganic material (filler) (for example, inorganic particles and/or a fiber), other common epoxy compounds, a solvent, or the like used in this field, if necessary. In general, the solvent may be optionally used to control the amount and/or the viscosity of the solid content of the composition of an alkoxysilyl compound in consideration of the processability of the composition, and the like.

Any compositions of an alkoxysilyl compound provided in accordance with any exemplary embodiments of the present invention may be used as an electronic material. The electronic material may include, without limitation, for example, a substrate for a semiconductor, a film, a prepreg, a laminated plate obtained by placing a metal layer on a base layer formed by using the composition of the present invention, a substrate, an encapsulating material (a packaging material), a build-up film, a build-up substrate, a printed circuit board, or the like. In addition, the epoxy composition may be used in various applications such as an adhesive, a paint and a composite material. In accordance with another embodiment of the present invention, an electronic material including or manufactured using the composition including an alkoxysilyl compound of the present invention is provided. Further, a semiconductor apparatus including or manufactured using the electronic material, is provided. Particularly, the semiconductor apparatus may be a semiconductor apparatus including a printed circuit board (for example, for installing a semiconductor device) including or manufactured using the composition including an alkoxysilyl compound of the present invention and/or may be a semiconductor apparatus including a semiconductor packaging material. In addition, a curing agent, an adhesive, a paint or a composite material including or manufactured using any compositions of an alkoxysilyl compound provided in any embodiments of the present invention, may be provided. In this case, the alkoxysilyl compound included in the composition of an alkoxysilyl compound of the present invention is not used as an additive but acts as a monomer for curing and/or a binder.

In accordance with another embodiment of the present invention, a cured product including or manufactured using the composition of an alkoxysilyl compound provided in an embodiment of the present invention is provided. In the case in which application of the composition of an alkoxysilyl compound provided in an embodiment of the present invention is practically conducted, for example, when the composition is applied as the electronic material, or the like, a cured product formed of the composition including an alkoxysilyl compound and a filler as an inorganic component may be commonly referred to as a composite.

The alkoxysilyl compound provided in the above-described embodiment of the present invention shows excellent heat resistance in the composite thereof and/or excellent flame retardant properties in the cured product thereof.

Particularly, the composite of the present invention may show a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are good when the CTE value is low, and the lower value of the CTE is not particularly limited.

For example, a composite including any alkoxysilyl compounds according to the present invention, and a glass fiber, for example, an E-glass fiber and/or a T-glass fiber as an inorganic material, and having the resin content (the resin content may or may not include inorganic particles) of 15 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite including any alkoxysilyl compounds according to the present invention, and inorganic particles as an inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product including an inorganic material) according to the present invention may be higher than 100° C., or may be Tg-less. The physical properties of the composite are good when the Tg value is high, and the upper value of the Tg is not particularly limited. In addition, a common thermosetting resin shows a large CTE-mismatch before and after Tg. However, the composition of the present invention has Tg-less properties, and no CTE change is observed in a measurement temperature section, or even Tg is observed, the deterioration of physical properties at a temperature of Tg or more is markedly decreased when compared to the common thermosetting resin.

Meanwhile, the cured product formed by using the alkoxysilyl compound itself (a cured product excluding an inorganic material) according to the present invention may have a CTE of 50 ppm/° C. to 100 ppm/° C.

In the present specification, the values limited by the range include the lower limit, the upper limit, any sub ranges in the range, and all numerals included in the range, unless specifically stated. For example, C1 to C10 is understood to include all of C1, C2, C3, C4, C5, C6, C7, C8, C9 and C10. In addition, in the case in which the lower limit or the upper limit of the numerical range is not defined, it may be found that the smaller or the larger value may provide better properties. In addition, in the case when the limit is not defined, any values may be included. For example, CTE of 4 ppm/° C. or less is understood to include every value in the range such as the CTE of 4, 3.5, 3, 2.7, 2, 1.4, 1, 0.5 ppm/° C., or the like.

In particular, in the composition of an alkoxysilyl compound according to the present invention, a composition including an alkoxysilyl compound and an epoxy compound may be easily synthesized when compared to silylepoxy having a silyl group and an epoxy group at the same time, and efficient processing may be possible.

Further, in the composition of an alkoxysilyl compound including an alkoxysilyl compound and an epoxy compound, where the alkoxysilyl compound includes at least one —OH group, a CTE may decrease further and Tg-less properties which has no glass transition temperature than a composition of an alkoxysilyl compound without an OH group were observed, and heat resistance properties may further improved.

In this case, the alkoxysilyl compound which may be included is selected from the group consisting of Formulae AI to DI, where at least one of substituents a and b is hydrogen, and at least two of substituents c to f may be Formula S1.

In addition, a particular alkoxysilyl compound according to the present invention may be selected from the group consisting of Formulae EI to GI, where at least one of substituents g to j is hydrogen, and at least two thereof re selected from the group consisting of Formula S1 and Formula S2.

3. Method for Preparing Alkoxysilyl Compounds

The alkoxysilyl compounds of Formulae AI to II according to the present invention may be prepared by the following methods, and each method will be explained in particular.

A. Method for preparing alkoxysilyl compound having at least two substituents of —CONH(CH$_2$)$_z$—SiR$_1$R$_2$R$_3$ and unreacted substituent (Method 1).

An alkoxysilyl compound may be obtained by reacting one starting material of the following Formulae AI to IS having at least two substituents of —CONH(CH$_2$)$_z$—SiR$_1$R$_2$R$_3$ and an unreacted substituent and with an isocyanate-based alkoxysilane of the following Formula M1 in the presence of an optional base and an optional solvent.

[Starting Materials]

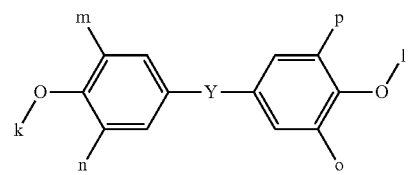
(AS)

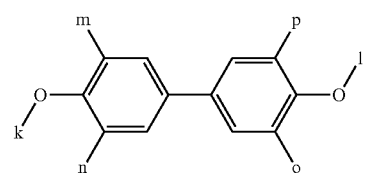
(BS)

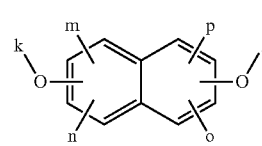
(CS)

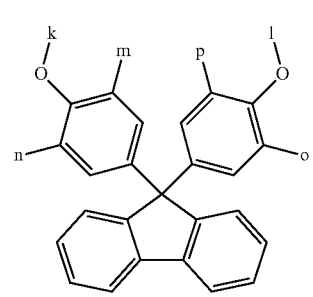
(DS)

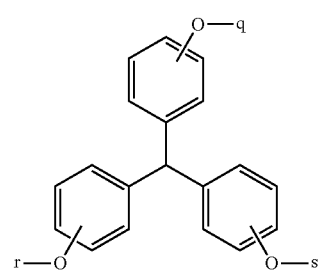
(ES)

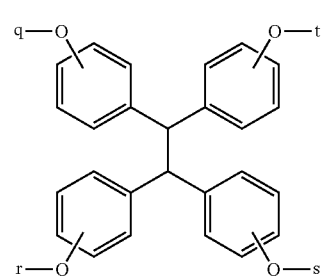
(FS)

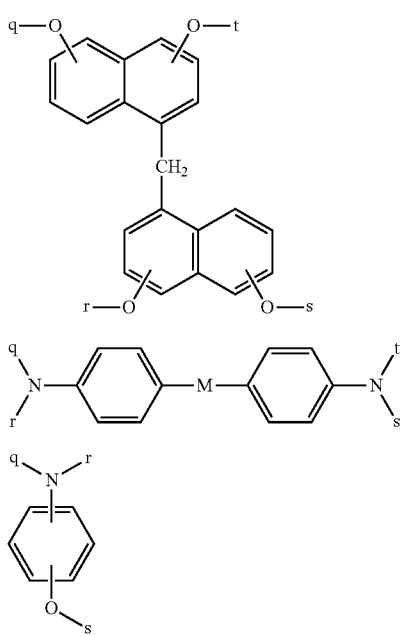

(GS)

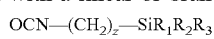

(HS)

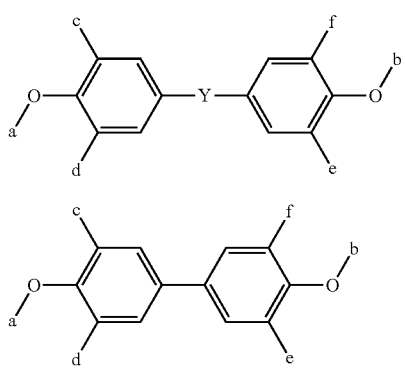

(IS)

(in Formulae AS to DS, substituents k and l are each independently hydrogen, m to p are each independently selected from the group consisting of hydrogen, $C_{1-10}$alkyl, $C_{1-10}$alkenyl, and $C_{6-30}$aryl, in Formula AS, Y is —$CH_2$—, —$C(CH_3)_2$—, —$C(CF_3)_2$—, —S—, or —$SO_2$—, in Formulae ES to IS, at least two substituents of q to t are hydrogen, and the remainder thereof may be each independently selected from $C_{1-10}$alkyl, $C_{1-10}$alkenyl, and $C_{6-30}$aryl, in Formula HS, M is —$CH_2$—, —$C(CH_3)_2$—, —$C(CF_3)_2$—, —S—, or —$SO_2$—, and a meta position of oxygen in Formula IS may be substituted with a linear or branched $C_{1-10}$alkyl group)

$$OCN—(CH_2)_z—SiR_1R_2R_3 \quad \text{[Formula M1]}$$

(where at least one of $R_1$ to $R_3$ is a linear or branched $C_{1-10}$alkoxy, the other thereof is linear or branched $C_{1-10}$alkyl, and z is an integer of 3 to 10)

[Final Products]

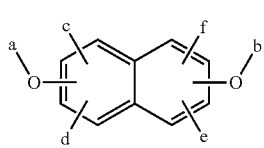

(AI)

(BI)

(CI)

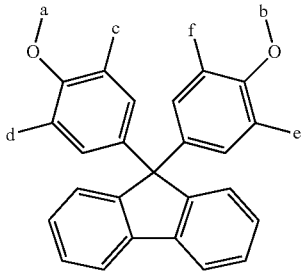

(DI)

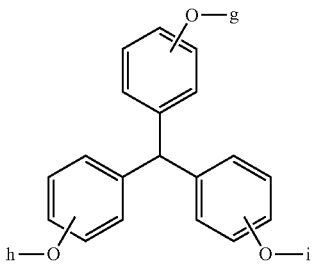

(EI)

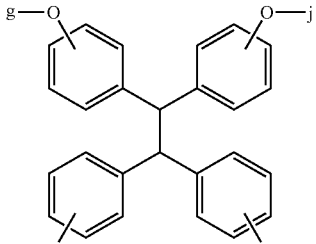

(FI)

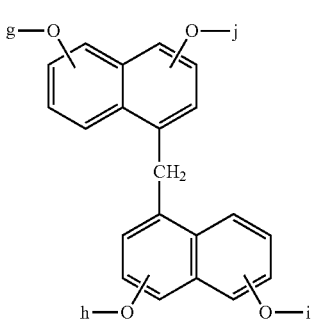

(GI)

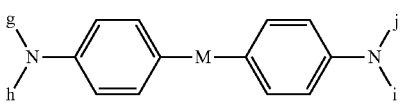

(HI)

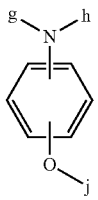

(II)

(in Formulae AI to DI, substituents a and b are each independently the following Formula S2, and substituents c to f are each independently selected from the group consisting of hydrogen, $C_{1-10}$alkyl, $C_{1-10}$alkenyl, and $C_{6-30}$aryl, in Formula AI, Y is —$CH_2$—, —$C(CH_3)_2$—, —$C(CF_3)_2$—, —S— or —$SO_2$—, in Formulae EI to II, at least two of substituents g to j are the following Formula S2, and the remainder thereof may be selected from the group consisting of hydrogen, $C_{1-10}$alkyl, $C_{1-10}$alkenyl, and $C_{6-30}$aryl, in Formula HI, M is —$CH_2$—, —$C(CH_3)_2$—, —$C(CF_3)_2$—, —S— or —$SO_2$—, and a meta position of oxygen in the above Formula II may be substituted with a linear or branched $C_{1-10}$alkyl group)

—CONH(CH$_2$)$_z$—SiR$_1$R$_2$R$_3$      [Formula S2]

(in Formula S2, at least one of $R_1$ to $R_3$ is a linear or branched $C_{1-10}$ alkoxy group, the other thereof is a linear or branched $C_{1-10}$ alkyl group, and z is an integer of 3 to 10)

In the above method 1, an alkoxysilyl compound may be prepared by reacting 0.1 to 5 equivalents of the isocyanate-based alkoxysilane of Formula M1 based on 1 equivalent of a hydroxyl group of one starting material of Formulae AS to IS in the presence of an optional base and an optional solvent. In addition, such reaction may be performed at 15° C. to 120° C. for 1 to 72 hours.

In method 1, the hydroxyl group of one starting material of Formulae AS to IS may be substituted with —CONH (CH$_2$)$_z$—SiR$_1$R$_2$R$_3$, and an alkoxysilyl compound having at least two alkoxysilyl groups and hydrogen, alkyl, alkenyl or aryl as unreacted substituents may be prepared.

The usable base may include, without limitation, for example, $K_2CO_3$, $Na_2CO_3$, $KHCO_3$, $NaHCO_3$, triethylamine, and diisopropylethylamine. These bases may be used alone or as a combination of two or more thereof. 0.1 to 5 equivalents of the base may be used based on 1 equivalent of the hydroxyl group of the starting material in consideration of reaction efficiency.

The solvents may be optionally used as occasion demands. For example, when the viscosity of the reactants at the reaction temperature is appropriate for conducting the reaction in the first step without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used, without specific limitation. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

B. Method for preparing alkoxysilyl compound having at least two substituents of —(CH$_2$)$_z$—SiR$_1$R$_2$R$_3$ and unreacted substituent (Method 2).

An alkoxysilyl compound having at least two substituents of —(CH$_2$)$_z$—SiR$_1$R$_2$R$_3$ and an unreacted substituent may be obtained by conducting a 1-1$^{st}$ step of reacting one starting material of Formulae AS to IS and an alkenyl compound of the following Formula M2 in the presence of an optional base and an optional solvent to obtain one of intermediates (1) of the following Formulae A1 to I1; and a 1-2$^{nd}$ step of reacting the intermediate (1) and an alkoxysilane of the following Formula M3 in the present of a metal catalyst and an optional solvent to obtain one final product of the following Formulae AI to II.

[Starting Materials]

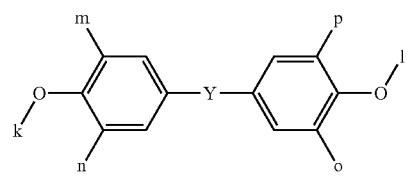
(AS)

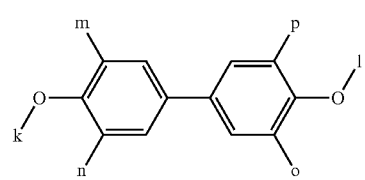
(BS)

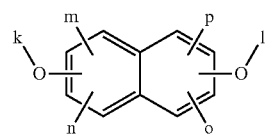
(CS)

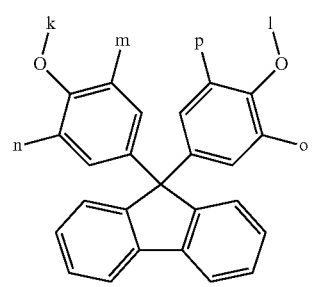
(DS)

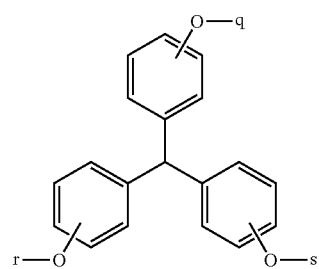
(ES)

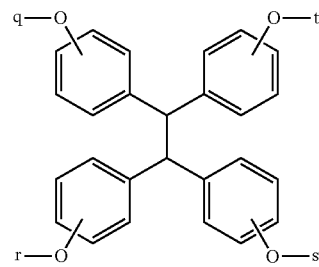
(FS)

-continued

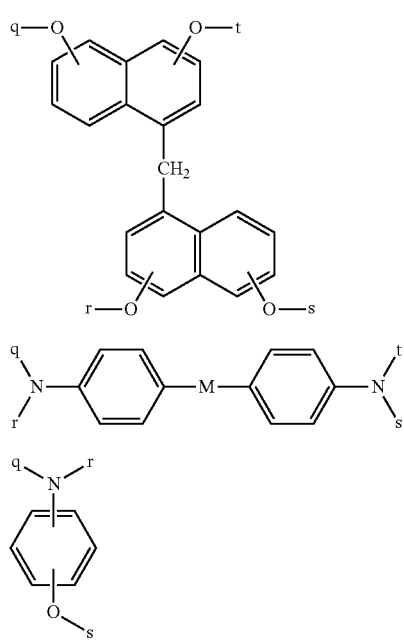

(GS)

(HS)

(IS)

(in Formulae AS to DS, substituents k and l are each independently hydrogen, m to p are each independently selected from the group consisting of hydrogen, $C_{1-10}$alkyl, $C_{1-10}$alkenyl, and $C_{6-30}$aryl, in Formula AS, Y is —$CH_2$—, —$C(CH_3)_2$—, —$C(CF_3)_2$—, —S—, or —$SO_2$—, in Formulae ES to IS, at least two substituents of q to t are hydrogen, and the other thereof is each independently selected from the group consisting of $C_{1-10}$alkyl, $C_{1-10}$alkenyl, and $C_{6-30}$aryl, in Formula HS, M is —$CH_2$—, —$C(CH_3)_2$—, —$C(CF_3)_2$—, —S—, or —$SO_2$—, and a meta position of oxygen in Formula IS may be substituted with a linear or branched $C_{1-10}$alkyl group)

$$X\text{—}(CH_2)_{z-2}\text{—}CH\text{=}CH_2 \qquad \text{[Formula M2]}$$

(in Formula M2, X is Cl, Br, I, —O—$SO_2$—$CH_3$, —O—$SO_2$—$CF_3$, —O—$SO_2$—$C_6H_4$—$CF_3$, —O—$SO_2$—$C_6H_4$—$NO_2$, or —O—$SO_2$—$C_6H_4$—$CH_3$, and z is an integer of 3 to 10)

[Intermediates (1)]

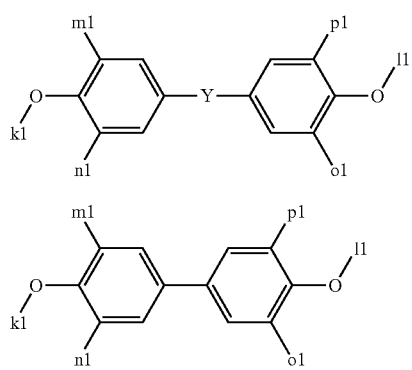

(A1)

(B1)

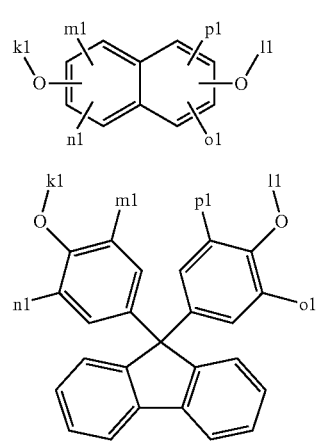

(C1)

(D1)

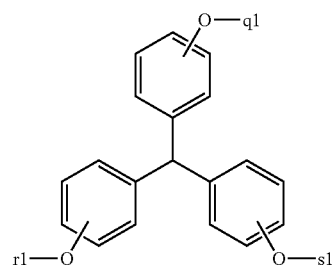

(E1)

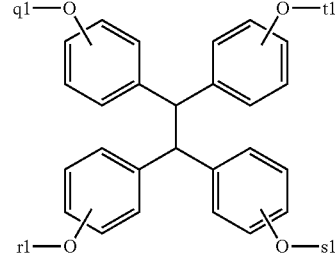

(F1)

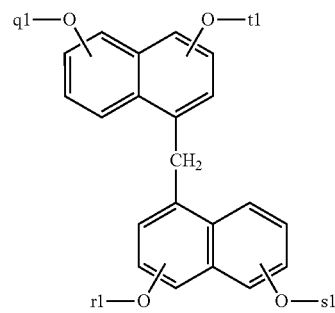

(G1)

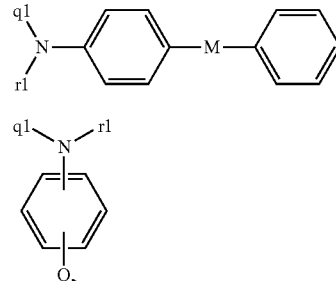

(H1)

(I1)

(in Formulae A1 to D1, substituents k1 and l1 are each independently —$(CH_2)_{z-2}CH\text{=}CH_2$ (z is an integer of 3 to 10), substituents m1 to p1 are each independently selected from the group consisting of hydrogen, alkyl, alkenyl and aryl, in Formula A1, Y is —$CH_2$—, —$C(CH_3)_2$—, —$C(CF_3)_2$—, —S—, or —$SO_2$—, in Formulae E1 to I1, at least two substituents of q1 to t1 is —$(CH_2)_{Z-2}CH$=$CH_2$ (z is an integer of 3 to 10), and the other thereof is each independently selected from the group consisting of hydrogen, alkyl, alkenyl and aryl, in Formula H1, M is —$CH_2$—, —$C(CH_3)_2$—, —$C(CF_3)_2$—, —S—, or —$SO_2$—, and a meta position of oxygen in Formula I1 may be substituted with a linear or branched $C_{1-10}$alkyl group)

$$HSiR_1R_2R_3 \quad [\text{Formula M3}]$$

(in Formula M3, at least one of $R_1$ to $R_3$ is linear or branched $C_{1-10}$alkoxy, and the other thereof is each independently linear or branched $C_{1-10}$alkyl)

[Final Products]

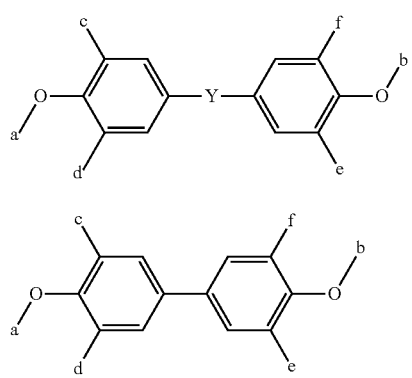

(AI)

(BI)

(CI)

(DI)

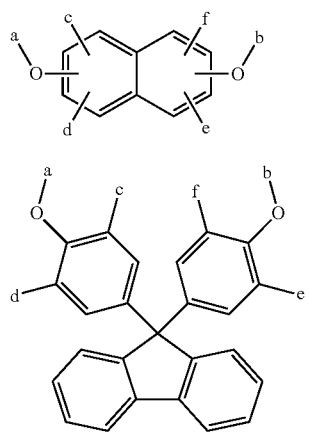

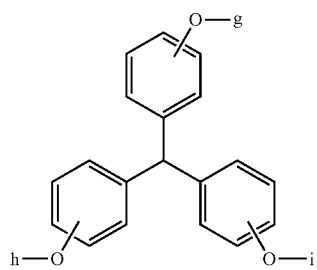

(EI)

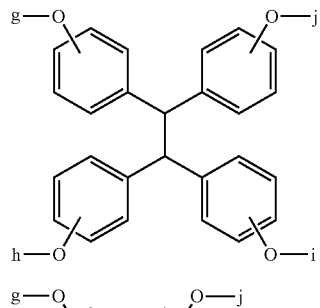

(FI)

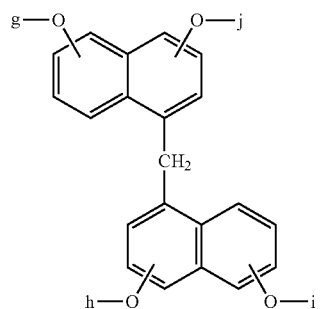

(GI)

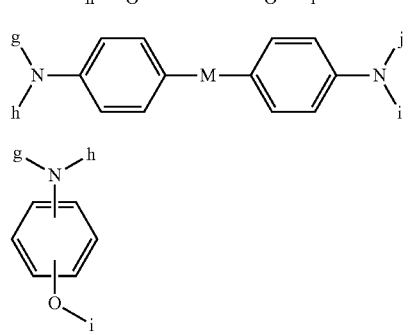

(HI)

(II)

(in Formulae AI to DI, substituents a and b are the following Formula S1, and substituents c to f are each independently selected from the group consisting of Formula S1, hydrogen, —OH, $C_{1-10}$alkyl, $C_{1-10}$alkenyl, and $C_{6-30}$aryl, in Formula AI, Y is —$CH_2$—, —$C(CH_3)_2$—, —$C(CF_3)_2$—, —S— or —$SO_2$—, in Formulae EI to II, at least two substituents of g to j are the following Formula S1, and the remainder thereof may be selected from the group consisting of hydrogen, $C_{1-10}$alkyl, $C_{1-10}$alkenyl, and $C_{6-30}$aryl, in Formula HI, M is —$CH_2$—, —$C(CH_3)_2$—, —$C(CF_3)_2$—, —S— or —$SO_2$—, and a meta position of oxygen in the above Formula II may be substituted with a linear or branched $C_{1-10}$alkyl group)

$$—(CH_2)_z—SiR_1R_2R_3 \quad [\text{Formula S1}]$$

(in Formula S1, at least one of $R_1$ to $R_3$ is linear or branched $C_{1-10}$alkoxy, the other thereof is linear or branched $C_{1-10}$alkyl, and z is an integer of 3 to 10)

In the 1-1$^{st}$ step, one starting material of Formulae AS to IS and an alkenyl compound of Formula M2 are reacted to obtain an intermediate (1) in which the hydroxyl group of the starting material is substituted with —$(CH_2)_{Z-2}CH$=$CH_2$ (Z is an integer of 3 to 10).

In the 1-1$^{st}$ step, the reaction is performed by adding 0.5 to 10 equivalents of the —$(CH_2)_{Z-2}CH$=$CH_2$ (Z is an integer of 3 to 10) of the alkenyl compound of Formula M2 based on 1 equivalent of the hydroxyl group of the starting materials at 15° C. to 100° C. for 1 to 120 hours to obtain the intermediates (1).

The base used in the 1-1$^{st}$ step may include, without limitation, for example, KOH, NaOH, $K_2CO_3$, $Na_2CO_3$, $KHCO_3$, $NaHCO_3$, pyridine, triethylamine, and diisopropylethylamine. These bases may be used alone or as a combination of two or more thereof 0.1 to 5 equivalents of the base may be used based on 1 equivalent of the hydroxyl group of the starting material in consideration of reaction efficiency.

The solvents used in the 1-1$^{st}$ step may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), $H_2O$, alcohols (methanol, ethanol), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

In the 1-2$^{nd}$ step, the intermediates (1) and the alkoxysilane of Formula M3 are reacted in the presence of a metal catalyst and an optional solvent, to obtain final products of the following Formulae AI to II in which the alkenyl of the intermediates (1) is substituted with the following Formula S1. The alkenyl of the intermediate (1) includes the alkenyl present in the starting material and —$(CH_2)_{Z-2}CH=CH_2$ (Z is an integer of 3 to 10) which is substituted by Formula M2. In the 1-2$^{nd}$ step, the alkenyl of the intermediates (1) and the alkoxysilane may react in an equivalent ratio according to stoichiometry, and 1 to 5 equivalents of the alkoxysilane of Formula M3 is added based on 1 equivalent of the alkenyl of the intermediates (1), and the reaction may be performed at 15° C. to 120° C. for 1 to 72 hours.

In the reaction of the 1-2$^{nd}$ step, the metal catalyst may include a platinum catalyst, for example, $PtO_2$ or chloroplatinic acid ($H_2PtCl_6$), without limitation. 0.005 to 0.05 equivalents of the platinum catalyst may be preferably used based on 1 equivalent of the alkenyl of the intermediates (1) in consideration of reaction efficiency.

In the 1-2$^{nd}$ step, solvents may be optionally used as occasion demands. In the 1-2$^{nd}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

C. Method for preparing alkoxysilyl compound having at least two substituents of —$CONH(CH_2)_Z$—$SiR_1R_2R_3$, at least one substituent of —$(CH_2)_Z$—$SiR_1R_2R_3$, and unreacted substituent (Method 3)

An alkoxysilyl compound having at least two substituents of —$CONH(CH_2)_Z$—$SiR_1R_2R_3$, at least one substituent of —$(CH_2)_Z$—$SiR_1R_2R_3$, and an unreacted substituent may be obtained by additionally combining the substituent of —$(CH_2)_Z$—$SiR_1R_2R_3$ with any one of Formulae EI to II, which may have a hydroxyl group among alkoxysilyl compounds having at least two substituents of —$CONH(CH_2)_Z$—$SiR_1R_2R_3$ and an unreacted substituent, prepared in method 1.

Particularly, the alkoxysilyl compound may be prepared by performing a 1-3$^{rd}$ step of reacting one of Formulae EI to II which may have a hydroxyl group among the alkoxysilyl compounds prepared in method 1, and an alkenyl compound of the following Formula M2 in the presence of an optional base and an optional solvent to substitute the hydroxyl group with —$(CH_2)_{Z-2}CH=CH_2$ (Z is an integer of 3 to 10); and a 1-4$^{th}$ step of reacting the —$(CH_2)_{Z-2}CH=CH_2$ (Z is an integer of 3 to 10) substituted in the 1-3$^{rd}$ step with the alkoxysilane of the following Formula M3 in the presence of a metal catalyst and an optional solvent for the substitution with the following Formula S1.

X—$(CH_2)_{z-2}$—CH=$CH_2$     [Formula M2]

(where X is a halide of Cl, Br, or I, —O—$SO_2$—$CH_3$, —O—$SO_2$—$CF_3$, —O—$SO_2$—$C_6H_4$—$CF_3$, —O—$SO_2$—$C_6H_4$—$NO_2$, or —O—$SO_2$—$C_6H_4$—$CH_3$, and z is an integer of 3 to 10)

$HSiR_1R_2R_3$     [Formula M3]

(where at least one of $R_1$ to $R_3$ is linear or branched $C_{1-10}$alkoxy, the other thereof is linear or branched $C_{1-10}$alkyl, and the alkoxy and the alkyl are linear or branched)

—$(CH_2)_z$—$SiR_1R_2R_3$     [Formula S1]

(in Formula S1, at least one of $R_1$ to $R_3$ is $C_{1-10}$alkoxy, the other thereof is $C_{1-10}$alkyl, the alkoxy and the alkyl are linear or branched, and z is an integer of 3 to 10)

In the 1-3$^{rd}$ step, one of Formulae EI to II, which has a hydroxyl group and the alkenyl compound of Formula M2 are reacted to substitute a hydroxyl group of one of Formulae EI to II with —$(CH_2)_{Z-2}CH=CH_2$ (Z is an integer of 3 to 10).

In the 1-3$^{rd}$ step, the reaction is performed by adding 0.5 to 10 equivalents of the —$(CH_2)_{Z-2}CH=CH_2$ (Z is an integer of 3 to 10) of the alkenyl compound of Formula M2 based on 1 equivalent of the hydroxyl group of one of Formulae EI to II, and the reaction may be performed at 15° C. to 100° C. for 1 to 120 hours.

The base used in the 1-3$^{rd}$ step may include, without limitation, for example, KOH, NaOH, $K_2CO_3$, $Na_2CO_3$, KHCO$_3$, NaHCO$_3$, NaH, pyridine, triethylamine, and diisopropylethylamine. These bases may be used alone or as a combination of two or more thereof 0.1 to 5 equivalents of the base may be used based on 1 equivalent of the hydroxyl group of the starting materials in consideration of reaction efficiency.

The solvents used in the 1-3$^{rd}$ step may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), H$_2$O, alcohols (methanol, ethanol), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

In the 1-4$^{th}$ step, the —(CH$_2$)$_{Z-2}$CH=CH$_2$ (Z is an integer of 3 to 10) substituted in the 1-3$^{rd}$ step and the alkoxysilane of Formula M3 are reacted in the presence of a metal catalyst and an optional solvent, the —(CH$_2$)$_{Z-2}$CH=CH$_2$ (Z is an integer of 3 to 10) is substituted with Formula S1 to obtain an alkoxysilyl compound having at least two substituents of —CONH(CH$_2$)$_Z$—SiR$_1$R$_2$R$_3$, at least one substituent of —(CH$_2$)$_Z$—SiR$_1$R$_2$R$_3$ and an unreacted substituent. In the 1-4$^{th}$ step, the —(CH$_2$)$_{Z-2}$CH=CH$_2$ (Z is an integer of 3 to 10) substituted in the 1-3$^{rd}$ step and the alkoxysilane may react in an equivalent ratio according to stoichiometry, and 1 to 5 equivalents of the alkoxysilane of Formula M3 is added based on 1 equivalent of the —(CH$_2$)$_{Z-2}$CH=CH$_2$ (Z is an integer of 3 to 10) substituted in the 1-3$^{rd}$ step, and the reaction may be performed at 15° C. to 120° C. for 1 to 72 hours.

In the reaction of the 1-4$^{th}$ step, the metal catalyst may include a platinum catalyst, for example, PtO$_2$ or chloroplatinic acid (H$_2$PtCl$_6$), without limitation. 0.005 to 0.05 equivalents of the platinum catalyst may be preferably used based on 1 equivalent of the —(CH$_2$)$_{Z-2}$CH=CH$_2$ (Z is an integer of 3 to 10) substituted in the 1-3$^{rd}$ step in consideration of reaction efficiency.

In the 1-4$^{th}$ step reaction, solvents may be optionally used as occasion demands. For example, in the 1-4$^{th}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

D. Method for preparing alkoxysilyl compound having at least two substituents of —(CH$_2$)$_Z$—SiR$_1$R$_2$R$_3$, at least one substituent of —CONH(CH$_2$)$_Z$—SiR$_1$R$_2$R$_3$, and unreacted substituent (Method 4)

An alkoxysilyl compound having at least two substituents of —(CH$_2$)$_Z$—SiR$_1$R$_2$R$_3$, at least one substituent of —CONH(CH$_2$)$_Z$—SiR$_1$R$_2$R$_3$, and an unreacted substituent may be obtained by additionally combining the substituent of —CONH(CH$_2$)$_Z$—SiR$_1$R$_2$R$_3$ with any one of Formulae EI to II, which may have a hydroxyl group among alkoxysilyl compounds having at least two substituents of —(CH$_2$)$_Z$—SiR$_1$R$_2$R$_3$ and an unreacted substituent prepared in method 2.

Particularly, the alkoxysilyl compound may be prepared by substituting the hydroxyl group with Formula S2 by reacting one of Formulae EI to II, which may have a hydroxyl group unsubstituted with alkenyl in the 1-1$^{st}$ step among the alkoxysilyl compounds prepared in method 2, with an isocyanate-based alkoxysilane of the following Formula M1 in the presence of an optional base and an optional solvent.

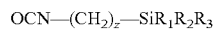

OCN—(CH$_2$)$_z$—SiR$_1$R$_2$R$_3$  [Formula M1]

(where at least one of R$_1$ to R$_3$ is C$_{1-10}$alkoxy, the other thereof is linear or branched C$_{1-10}$alkyl, the alkoxy and the alkyl are linear or branched, and z is an integer of 3 to 10)

In method 4, the alkoxysilyl compound may be prepared by reacting 1 to 5 equivalents of the isocyanate-based alkoxysilane of Formula M1 based on 1 equivalent of the hydroxyl group of one among Formulae EI to II in the presence of an optional base and an optional solvent. Such a reaction may be performed at 15° C. to 120° C. for 1 to 72 hours.

By method 4, the hydroxyl group of one of Formulae EI to II is substituted with —CONH(CH$_2$)$_Z$—SiR$_1$R$_2$R$_3$, and an alkoxysilyl compound having at least two substituents of —(CH$_2$)$_Z$—SiR$_1$1R$_2$R$_3$, at least one substituent of —CONH(CH$_2$)$_Z$—SiR$_1$R$_2$R$_3$, and selectively, an unreacted substituent of hydrogen, alkyl, alkenyl or aryl, may be prepared.

The usable base may include, without limitation, for example, K$_2$CO$_3$, Na$_2$CO$_3$, KHCO$_3$, NaHCO$_3$, triethylamine, and diisopropylethylamine. These bases may be used alone or as a combination of two or more thereof. 0.1 to 5 equivalents of the base may be used based on 1 equivalent of the hydroxyl group of the starting material in consideration of reaction efficiency.

In the reaction, the solvents may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

E. Method for preparing alkoxysilyl compound, by which starting materials (Formulae AS to DS) of which all substituents are hydrogen are alkenylated, and rearrangement reaction is performed once to have two substituents of —$(CH_2)_Z$—$SiR_1R_2R_3$, or rearrangement reaction is performed, and alkenylation is performed to have three or four substituents of —$(CH_2)_Z$—$SiR_1R_2R_3$ (Method 5)

Method 5-1: An alkoxysilyl compound having two substituents of —$(CH_2)_Z$—$SiR_1R_2R_3$ may be prepared by alkenylating starting materials (Formulae AS to DS) of which all substituents are hydrogen, and performing a rearrangement reaction once.

[Structure Example Synthesized by Method 5-1]

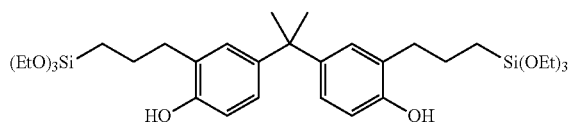

Preparation Method 5-2: An alkoxysilyl compound having 3-4 substituents of —$(CH_2)_Z$—$SiR_1R_2R_3$ may be prepared by alkenylating starting materials (Formulae AS to DS) of which all substituents are hydrogen, performing a rearrangement reaction once, and then alkenylating again.

[Structure Example Synthesized by Method 5-2]

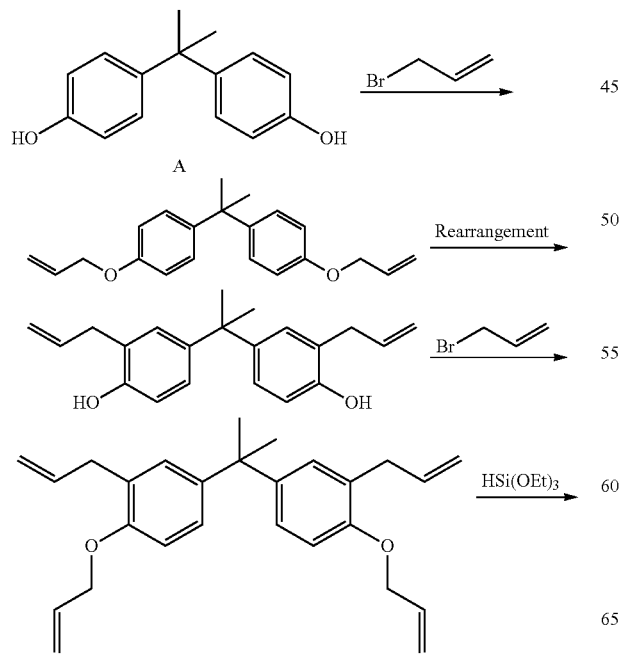

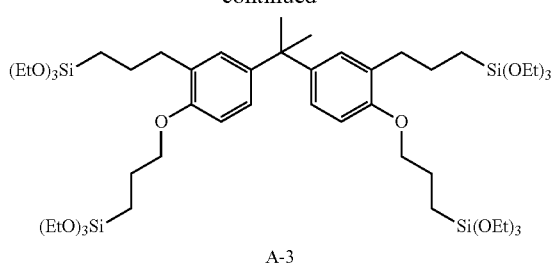

A-3

That is, an alkoxysilyl compound having 2-4 substituents of —$(CH_2)_Z$—$SiR_1R_2R_3$ may be prepared by alkenylating starting materials (Formulae AS to DS) of which all substituents are hydrogen, performing a rearrangement reaction once, and then alkenylating again to combine a substituent of —$(CH_2)_Z$—$SiR_1R_2R_3$.

Particularly, the alkoxysilyl compound may be obtained by performing 2-1$^{st}$ step of reacting one starting material of the following Formulae AS to DS with an alkenyl compound of the following Formula M2 in the presence of an optional base and an optional solvent to obtain one of intermediates (21) in which a hydroxyl group is substituted with —$(CH_2)_{Z-2}CH=CH_2$ (Z is an integer of 3 to 10); 2-2$^{nd}$ step of performing a rearrangement reaction with respect to the intermediate (21) to obtain one of intermediates (22) having a hydroxyl group; 2-3$^{rd}$ step of reacting the intermediate (22) with the alkenyl compound of the following Formula M2 in the presence of an optional base and an optional solvent to obtain one of intermediates (23) in which a hydroxyl group is substituted with —$(CH_2)_{Z-2}CH=CH_2$ (Z is an integer of 3 to 10); and 2-4$^{th}$ step of reacting the intermediate (23) with an alkoxysilane of the following Formula M3 in the presence of a metal catalyst and an optional solvent to obtain one final product of the following Formulae AI to DI.

[Starting Materials]

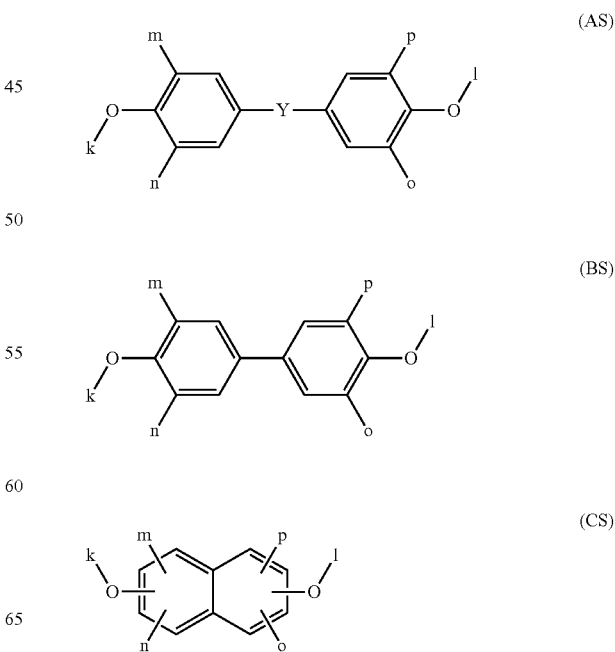

(DS)

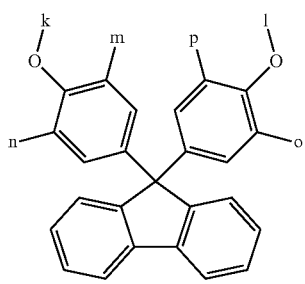

(in Formulae AS to DS, substituents k to p are hydrogen, and in Formula AS,
Y is —CH$_2$—, —C(CH$_3$)$_2$—, —C(CF$_3$)$_2$—, —S— or —SO$_2$—)

$$X-(CH_2)_{z-2}-CH=CH_2 \quad \text{[Formula M2]}$$

(where X is a halide of Cl, Br, or I, —O—SO$_2$—CH$_3$, —O—SO$_2$—CF$_3$, —O—SO$_2$—C$_6$H$_4$—CF$_3$, —O—SO$_2$—C$_6$H$_4$—NO$_2$, or —O—SO$_2$—C$_6$H$_4$—CH$_3$, and z is an integer of 3 to 10)

[Intermediates (21)]

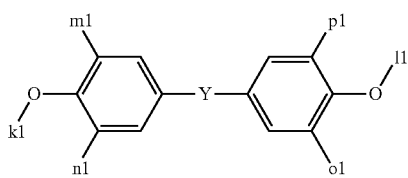 (A21)

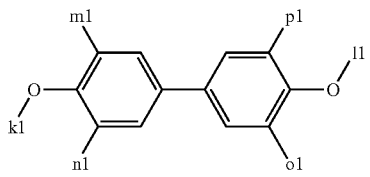 (B21)

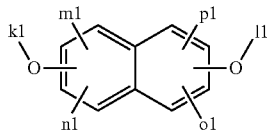 (C21)

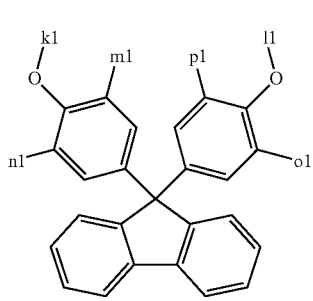 (D21)

(in Formulae A21 to D21, substituents k1 to l1 are —(CH$_2$)$_{z-2}$CH=CH$_2$ (Z is an integer of 3 to 10), m1 to p1 are hydrogen, and in Formula A21, Y is —CH$_2$—, —C(CH$_3$)$_2$—, —C(CF$_3$)$_2$—, —S— or —SO$_2$—)

[Intermediates (22)]

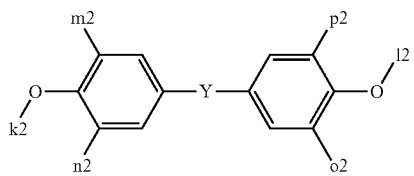 (A22)

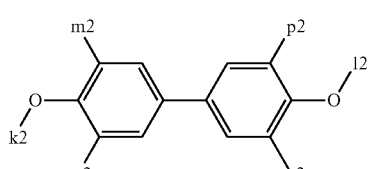 (B22)

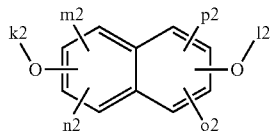 (C22)

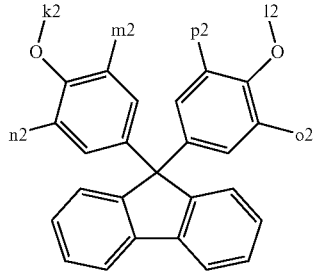 (D22)

(in Formulae A22 to D22, among substituents k2 to p2, one of m2 and n2 and one of o2 and p2 are —(CH$_2$)$_{Z-2}$CH=CH$_2$ (Z is an integer of 3 to 10), and the other thereof is hydrogen, and in Formula A22, Y is —CH$_2$—, —C(CH$_3$)$_2$—, —C(CF$_3$)$_2$—, —S— or —SO$_2$—)

[Intermediates (23)]

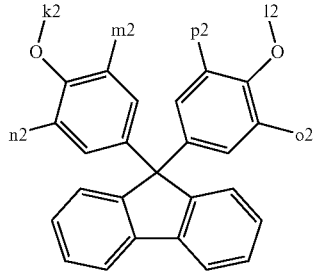 (A23)

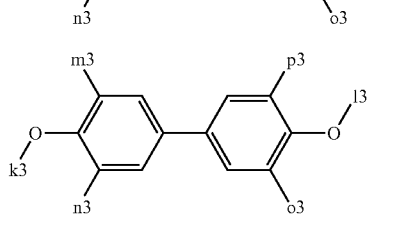 (B23)

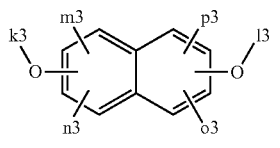 (C23)

-continued

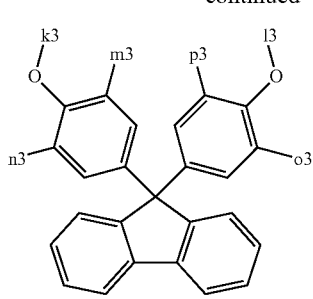

(D23)

(in Formulae A23 to D23, among substituents k3 to p3, k3; l3; one of m3 and n3; and one of o3 and p3 are —(CH$_2$)$_{Z-2}$CH=CH$_2$ (Z is an integer of 3 to 10), and the other thereof is hydrogen, and in Formula A23, Y is —CH$_2$—, —C(CH$_3$)$_2$—, —C(CF$_3$)$_2$—, —S— or —SO$_2$—)

HSiR$_1$R$_2$R$_3$ [Formula M3]

(where at least one of R$_1$ to R$_3$ is C$_{1-10}$alkoxy, the other thereof is linear or branched C$_{1-10}$alkyl, and the alkoxy and the alkyl are linear or branched)

[Final Products]

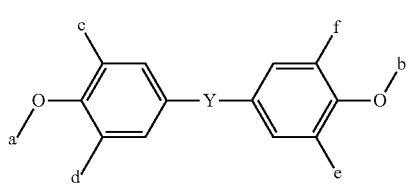

(AI)

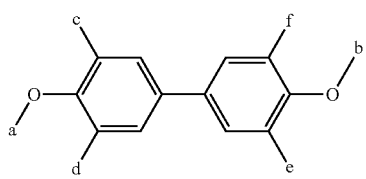

(BI)

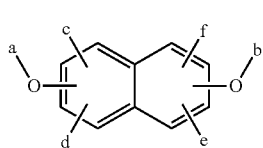

(CI)

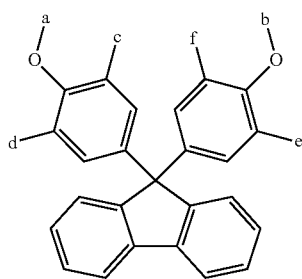

(DI)

(in Formulae AI to DI, at least two substituents of a to f are the following Formula S1, and the other thereof is hydrogen or —(CH$_2$)$_{Z-2}$CH=CH$_2$ (Z is an integer of 3 to 10), and in Formula AI, Y is —CH$_2$—, —C(CH$_3$)$_2$—, —C(CF$_3$)$_2$—, —S— or —SO$_2$—)

—(CH$_2$)$_z$—SiR$_1$R$_2$R$_3$ [Formula S1]

(in Formula S1, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the 2-1$^{st}$ step, an intermediate (21) in which a hydroxyl group is substituted with —(CH$_2$)$_{Z-2}$CH=CH$_2$ (Z is an integer of 3 to 10) may be obtained by reacting one starting material of Formulae AS to DS of which all substituents are hydrogen with an alkenyl compound of Formula M2 in the presence of an optional base and an optional solvent.

The 2-1$^{st}$ step may be performed by reacting 0.5 to 10 equivalents of the —(CH$_2$)$_{Z-2}$CH=CH$_2$ (Z is an integer of 3 to 10) of the alkenyl compound of Formula M2 based on 1 equivalent of the hydroxyl group of one among Formulae AS to DS, and the reaction may be performed at 15° C. to 100° C. for 1 to 120 hours.

In the 2-1$^{st}$ step, the base used may include, without limitation, for example, KOH, NaOH, K$_2$CO$_3$, Na$_2$CO$_3$, KHCO$_3$, NaHCO$_3$, NaH, pyridine, triethylamine, and diisopropylethylamine. These bases may be used alone or as a combination of two or more thereof 0.1 to 5 equivalents of the base may be used based on 1 equivalent of the hydroxyl group of the starting material in consideration of reaction efficiency.

In the 2-1$^{st}$ step, the solvents may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), H$_2$O, alcohols (methanol, ethanol) or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

The 2-2$^{nd}$ step for obtaining the intermediates (22) having a hydroxyl group may be performed by performing a rearrangement reaction with respect to the intermediates (21) alkenylated in the 2-1$^{st}$ step.

Since the rearrangement reaction is a unimolecular reaction, a equivalent number is not limited, and the reaction may be performed at 140° C. to 250° C. for 1 to 200 hours, or at 120° C. to 250° C. for 1 to 1,000 minutes by irradiating microwaves of 100 W to 750 W.

According to the increase of the temperature during the rearrangement reaction, and if the viscosity of the reactants is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. However, the reaction may be performed in the presence of a solvent if necessary, and xylene, 1,2-dichlorobenzene, N,N-diethylaniline, or the like may be used, without specific limitation. The rearrangement reaction which will be described later may be performed by the same method as the 2-2$^{nd}$ step.

In the 2-3$^{rd}$ step, intermediates (23) in which a hydroxyl group is substituted with —(CH$_2$)$_{Z-2}$CH=CH$_2$ (Z is an integer of 3 to 10) may be obtained by reacting the intermediates (22) having a hydroxyl group prepared in the 2-2$^{nd}$ step with the alkenyl compound of Formula M2 in the presence of an optional base and an optional solvent.

The 2-3$^{rd}$ step is a step of alkenylating the intermediates (22), and the same conditions for the alkenylation reaction performed in the 2-1$^{st}$ step may be applied.

In the 2-4$^{th}$ step, the following final products of Formulae AI to DI, that is, alkoxysilyl compounds having 2-4 substituents of —(CH$_2$)$_Z$—SiR$_1$R$_2$R$_3$ may be obtained by reacting the intermediates (23) alkenylated in the 2-3$^{rd}$ step and the alkoxysilane of Formula M3 in the presence of a metal catalyst and an optional solvent. In the 2-4$^{th}$ step, the —(CH$_2$)$_{Z-2}$CH=CH$_2$(Z is an integer of 3 to 10) substituted in the 2-3$^{rd}$ step and the alkoxysilane react in an equivalent ratio according to stoichiometry, and 1 to 5 equivalents of the alkoxysilane of Formula M3 is added and reacted based on 1 equivalent of the —(CH$_2$)$_{Z-2}$CH=CH$_2$ (Z is an integer of 3 to 10) substituted in the 2-3$^{rd}$ step, and the reaction may be performed at 15° C. to 120° C. for 1 to 72 hours.

In the reaction of the 2-4$^{th}$ step, the metal catalyst may include a platinum catalyst, for example, PtO$_2$ or chloroplatinic acid (H$_2$PtCl$_6$), without limitation. 0.005 to 0.05 equivalents of the platinum catalyst may preferably be used based on 1 equivalent of the alkenyl which is substituted in the 1-3$^{rd}$ step in consideration of reaction efficiency.

In the 2-4$^{th}$ step, solvents may be optionally used as occasion demands. In the 2-4$^{th}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

F. Method for preparing alkoxysilyl compound, by which starting materials (Formulae AS to DS) of which all substituents are hydrogen are alkenylated, and rearrangement reaction is performed once to have two substituents of —CONH(CH$_2$)$_Z$—SiR$_1$R$_2$R$_3$ (Method 6)

An alkoxysilyl compound having two substituents of —CONH(CH$_2$)$_Z$—SiR$_1$R$_2$R$_3$ and alkenyl may be prepared by alkenylating starting materials (Formulae AS to DS) of which all substituents are hydrogen, performing a rearrangement reaction once, and combining the substituent of —CONH(CH$_2$)$_Z$—SiR$_1$R$_2$R$_3$.

Particularly, the alkoxysilyl compound is prepared by performing 2-5$^{th}$ step for obtaining one final product of the following Formulae AI to DI by reacting one of the intermediates (22) obtained by alkenylating one of starting materials (Formulae AS to DS) of which all substituents are hydrogen and performing a rearrangement reaction once in method 5, with an isocyanate-based alkoxysilane of Formula M1 in the presence of an optional base and an optional solvent.

[Intermediates (22)]

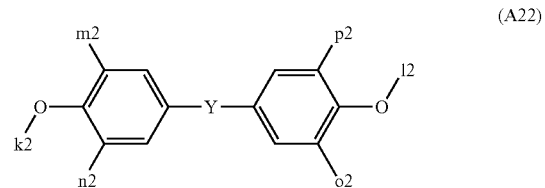

(A22)

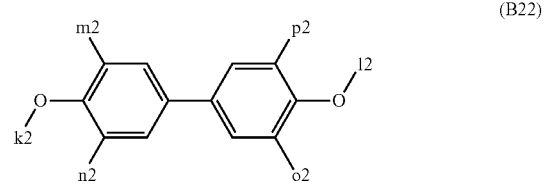

(B22)

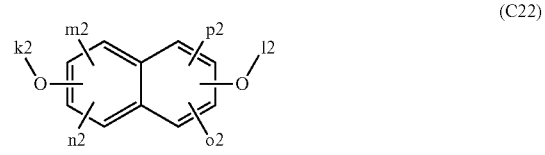

(C22)

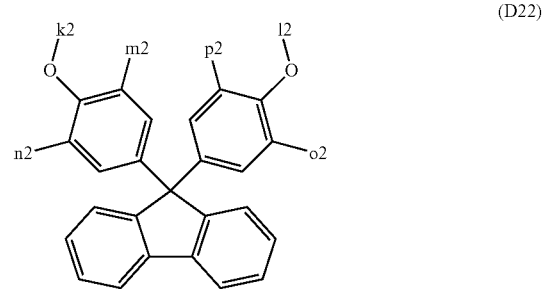

(D22)

(in Formulae A22 to D22, among substituents k2 to p2, one of m2 and n2 and one of o2 and p2 are —(CH$_2$)$_{Z-2}$CH=CH$_2$ (Z is an integer of 3 to 10), and the other thereof is hydrogen, and in Formula A22, Y is —CH$_2$—, —C(CH$_3$)$_2$—, —C(CF$_3$)$_2$—, —S— or —SO$_2$—)

OCN—(CH$_2$)$_z$—SiR$_1$R$_2$R$_3$ [Formula M1]

(where at least one of R$_1$ to R$_3$ is C$_{1-10}$alkoxy, the other thereof is linear or branched C$_{1-10}$alkyl, the alkoxy and the alkyl are linear or branched, and z is an integer of 3 to 10)

[Final Products]

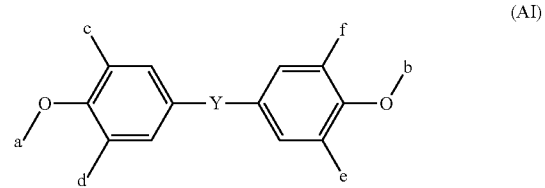

(AI)

-continued

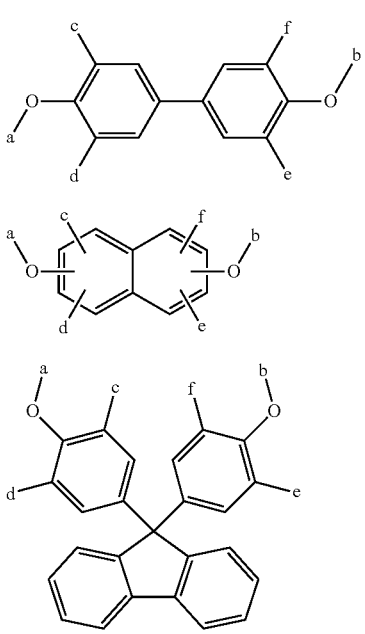

(in Formulae AI to DI, substituents a and b are the following Formula S2, one of c and d and one of e and f are —(CH$_2$)$_{Z-2}$CH=CH$_2$ (Z is an integer of 3 to 10), and the other thereof is hydrogen, and in Formula AI, Y is —CH$_2$—, —C(CH$_3$)$_2$—, —C(CF$_3$)$_2$—, —S— or —SO$_2$—)

—CONH(CH$_2$)$_z$—SiR$_1$R$_2$R$_3$      [Formula S2]

(in Formula S2, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the 2-5$^{th}$ step, the alkoxysilyl compound may be prepared by reacting 1 to 5 equivalents of the isocyanate-based alkoxysilane of Formula M1 based on 1 equivalent of the hydroxyl group of the intermediates (22) in the presence of an optional base and an optional solvent. In addition, the reaction may be performed at 15° C. to 120° C. for 1 to 72 hours.

In the 2-5$^{th}$ step, the base may include, without limitation, for example, K$_2$CO$_3$, Na$_2$CO$_3$, KHCO$_3$, NaHCO$_3$, NaH, pyridine, triethylamine, and diisopropylethylamine. These bases may be used alone or as a combination of two or more thereof. 0.1 to 5 equivalents of the base may be used based on 1 equivalent of the hydroxyl group of the intermediates (22) in consideration of reaction efficiency.

In the 2-5$^{th}$ step, solvents may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

G. Method for preparing alkoxysilyl compound, by which starting materials (Formulae AS to DS) of which all substituents are hydrogen are alkenylated, and rearrangement reaction is performed once to have two substituents of —CONH(CH$_2$)$_z$—SiR$_1$R$_2$R$_3$, and at least one substituent of —(CH$_2$)$_z$—SiR$_1$R$_2$R$_3$ (Method 7)

An alkoxysilyl compound having two substituents of —CONH(CH$_2$)$_z$—SiR$_1$R$_2$R$_3$ and at least one substituent of —(CH$_2$)$_z$—SiR$_1$R$_2$R$_3$ may be prepared by additionally combining the sub stituent of —(CH$_2$)$_z$—SiR$_1$R$_2$R$_3$ with the alkoxysilyl compound having two sub stituents of —CONH (CH$_2$)$_z$—SiR$_1$R$_2$R$_3$ and alkenyl by method 6.

Particularly, the alkoxysilyl compound is prepared by performing the 2-6$^{th}$ step for obtaining one final product of the following Formulae AI to DI by reacting the one of the alkoxysilyl compounds prepared in method 6 with the alkoxysilane of the following Formula M3 in the presence of a metal catalyst and an optional solvent.

HSiR$_1$R$_2$R$_3$      [Formula M3]

(in which, at least one of R$_1$ to R$_3$ is C$_{1-10}$alkoxy, the other thereof is linear or branched C$_{1-10}$alkyl, and the alkoxy and the alkyl are linear or branched)

[Final Products]

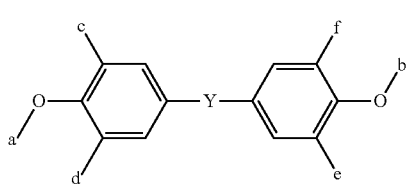

(AI)

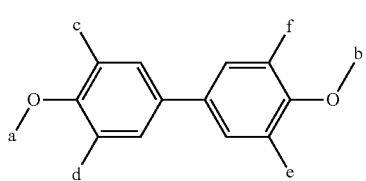

(BI)

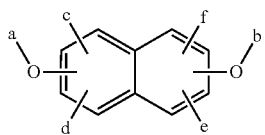

(CI)

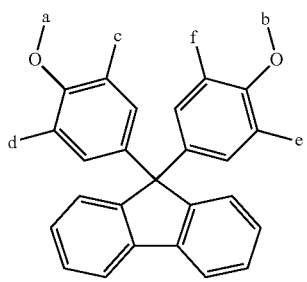

(DI)

(in Formulae AI to DI, substituents a and b are the following Formula S2, one of c and d and one of e and f are the following Formula S2, and the other thereof is hydrogen, and in Formula AI, Y is —CH$_2$—, —C(CH$_3$)$_2$—, —C(CF$_3$)$_2$—, —S— or —SO$_2$—)

—(CH$_2$)$_z$—SiR$_1$R$_2$R$_3$ [Formula S1]

—CONH(CH$_2$)$_z$—SiR$_1$R$_2$R$_3$ [Formula S2]

(in Formulae S1 and S2, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the reaction of the 2-6$^{th}$ step, the —(CH$_2$)$_{z-2}$CH=CH$_2$ (Z is an integer of 3 to 10) of the alkoxysilyl compound prepared in the 2-5$^{th}$ step and the alkoxysilane may react in an equivalent ratio according to stoichiometry, and 1 to 5 equivalents of the alkoxysilane of Formula M3 is added and reacted based on 1 equivalent of the —(CH$_2$)$_{z-2}$CH=CH$_2$ (Z is an integer of 3 to 10) of the alkoxysilyl compound prepared in the 2-5$^{th}$ step, and the reaction may be performed at 15° C. to 120° C. for 1 to 72 hours.

In the reaction of the 2-6$^{th}$ step, the metal catalyst may include a platinum catalyst, for example, PtO$_2$ or chloroplatinic acid (H$_2$PtCl$_6$), without limitation. 0.005 to 0.05 equivalents of the platinum catalyst may preferably be used based on 1 equivalent of the —(CH$_2$)$_{Z-2}$CH=CH$_2$ (Z is an integer of 3 to 10) of the alkoxysilyl compound prepared in the 2-5$^{th}$ step in consideration of reaction efficiency.

In the 2-6$^{th}$ step reaction, solvents may be optionally used as occasion demands. In the 2-6$^{th}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

H. Method for preparing alkoxysilyl compound, by which starting materials (Formulae AS to DS) of which all substituents are hydrogen are alkenylated, and rearrangement reaction is performed twice to have four substituents of —(CH$_2$)$_Z$—SiR$_1$R$_2$R$_3$ and hydroxyl group (Method 8)

An alkoxysilyl compound having four substituents of —(CH$_2$)$_Z$—SiR$_1$R$_2$R$_3$ and a hydroxyl group may be prepared by additionally performing a rearrangement reaction with respect to the intermediates (23) prepared in method 5 and additionally combining the sub stituent of —(CH$_2$)$_Z$—SiR$_1$R$_2$R$_3$.

Particularly, the alkoxysilyl compound may be prepared by performing the 3-1$^{st}$ step of performing a rearrangement reaction with respect to the intermediates (23) prepared in method 5 to obtain the intermediates (31) having one hydroxyl group; and 3-2$^{nd}$ step of reacting the intermediates (31) with the alkoxysilane of the following Formula M3 in the presence of a metal catalyst and an optional solvent to obtain one final product of the following Formulae AI to DI.

[Intermediates (23)]

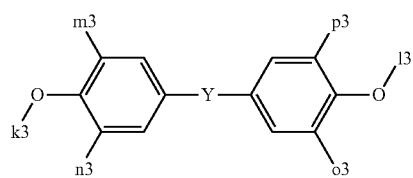
(A23)

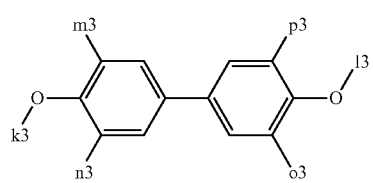
(B23)

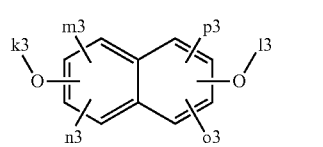
(C23)

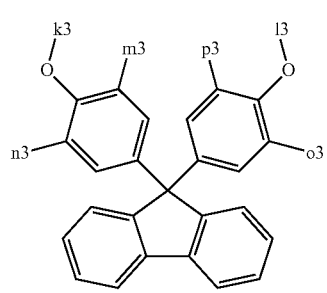
(D23)

(in Formulae A23 to D23, among substituents k3 to p3, k3; l3; one of m3 and n3; and one of o3 and p3 are —(CH$_2$)$_{Z-2}$CH=CH$_2$ (Z is an integer of 3 to 10), and the other thereof is hydrogen, and in Formula A23, Y is —CH$_2$—, —C(CH$_3$)$_2$—, —C(CF$_3$)$_2$—, —S— or —SO$_2$—)

[Intermediates (31)]

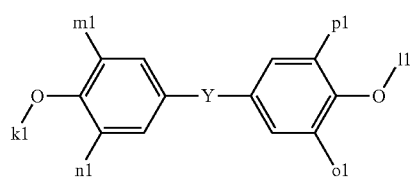
(A31)

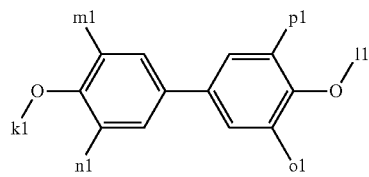
(B31)

-continued

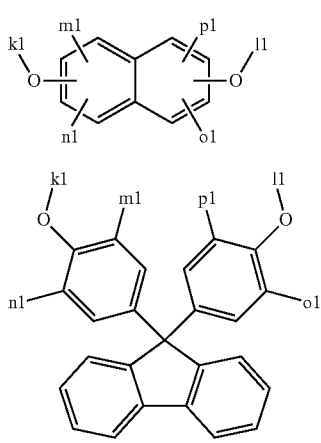

(C31)

(D31)

(in Formulae A31 to D31, substituents k1 to l1 are hydrogen, m1 to p1 are —(CH$_2$)$_{Z\text{-}2}$CH=CH$_2$ (Z is an integer of 3 to 10), and in Formula A31, Y is —CH$_2$—, —C(CH$_3$)$_2$—, —C(CF$_3$)$_2$—, —S— or —SO$_2$—)

HSiR$_1$R$_2$R$_3$ [Formula M3]

(where at least one of R$_1$ to R$_3$ is C$_{1\text{-}10}$alkoxy, the other thereof is linear or branched C$_{1\text{-}10}$alkyl, and the alkoxy and the alkyl are linear or branched)

[Final Products]

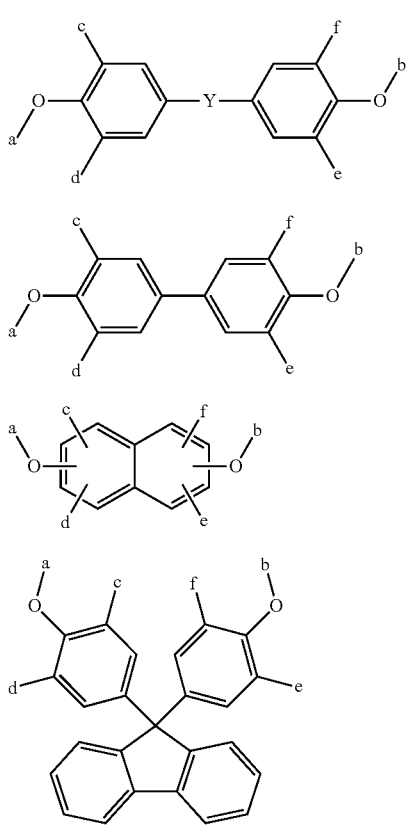

(AI)

(BI)

(CI)

(DI)

(in Formulae AI to DI, substituents a and b are hydrogen, at least two of c to f are the following Formula S1, and the other thereof is —(CH$_2$)$_{Z\text{-}2}$CH=CH$_2$ (Z is an integer of 3 to 10), and in Formula AI, Y is —CH$_2$—, —C(CH$_3$)$_2$—, —C(CF$_3$)$_2$—, —S— or —SO$_2$—)

—(CH$_2$)$_z$—SiR$_1$R$_2$R$_3$ [Formula S1]

(in Formula S1, at least one of R$_1$ to R$_3$ is C$_{1\text{-}10}$alkoxy, the other thereof is C$_{1\text{-}10}$alkyl, the alkoxy and the alkyl are linear or branched, and z is an integer of 3 to 10)

The rearrangement reaction in the 3-1$^{st}$ step may be performed according to the same rearrangement reaction as the 2-2$^{nd}$ step in method 5. Through the rearrangement reaction, intermediates (31) having four substituents of —(CH$_2$)$_{Z\text{-}2}$CH=CH$_2$ (Z is an integer of 3 to 10) and a hydroxyl group may be obtained.

In the 3-2$^{nd}$ step, the final products of Formulae AI to DI may be obtained by reacting the intermediates (31) prepared in the 3-1$^{st}$ step and the alkoxysilane of Formula M3 in the presence of a metal catalyst and an optional solvent.

In the 3-2$^{nd}$ step, the —(CH$_2$)$_{Z\text{-}2}$CH=CH$_2$ (Z is an integer of 3 to 10) of the intermediates (31) prepared in the 3-1$^{st}$ step and the alkoxysilane react in an equivalent ratio according to stoichiometry, and 1 to 5 equivalents of the alkoxysilane of Formula M3 is added and reacted based on 1 equivalent of the —(CH$_2$)$_{Z\text{-}2}$CH=CH$_2$(Z is an integer of 3 to 10) of the intermediates (31) prepared in the 3-1$^{st}$ step, and the reaction may be performed at 15° C. to 120° C. for 1 to 72 hours.

In the reaction of the 3-2$^{nd}$ step, the metal catalyst may include a platinum catalyst, for example, PtO$_2$ or chloroplatinic acid (H$_2$PtCl$_6$), without limitation. 0.005 to 0.05 equivalents of the platinum catalyst may preferably be used based on 1 equivalent of the —(CH$_2$)$_{Z\text{-}2}$CH=CH$_2$ (Z is an integer of 3 to 10) of the intermediates (31) prepared in the 3-1$^{st}$ step in consideration of reaction efficiency.

In the 3-2$^{nd}$ step, solvents may be optionally used as occasion demands. In the 3-2$^{nd}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

I. Method for preparing alkoxysilyl compound, by which starting materials (Formulae AS to DS) of which all substituents are hydrogen are alkenylated, and rearrangement reaction is performed twice to have six substituents of —(CH$_2$)$_Z$—SiR$_1$R$_2$R$_3$ and no hydroxyl group (Method 9)

An alkoxysilyl compound having six substituents of —(CH$_2$)$_Z$—SiR$_1$R$_2$R$_3$ and no hydroxyl group may be prepared by alkenylating the intermediates (31) of method 8 and additionally combining the substituent of —(CH$_2$)$_Z$—SiR$_1$R$_2$R$_3$.

Particularly, the alkoxysilyl compound may be prepared by performing a 3-3$^{rd}$ step of reacting the intermediates (31) prepared in the 3-1$^{st}$ step of method 8 with the following Formula M2 in the presence of an optional base and an optional solvent to obtain the intermediates (32) in which the hydroxyl group is substituted with —(CH$_2$)$_{Z-2}$CH═CH$_2$ (Z is an integer of 3 to 10); and 3-4$^{th}$ step of reacting the intermediates (32) with the alkoxysilane of the following Formula M3 in the presence of a metal catalyst and an optional solvent to obtain one final product of the following Formulae AI to DI.

[Intermediates (31)]

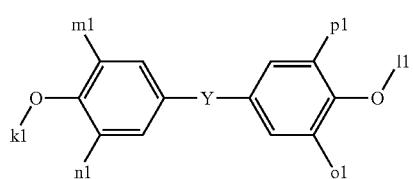
(A31)

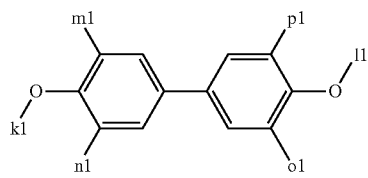
(B31)

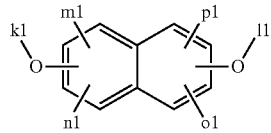
(C31)

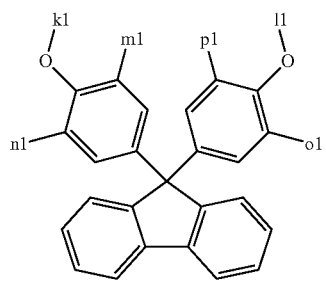
(D31)

(in Formulae A31 to D31, substituents k1 and l1 are hydrogen, and m1 to p1 are —(CH$_2$)$_{Z-2}$CH═CH$_2$ (Z is an integer of 3 to 10), and in Formula A31 Y is —CH$_2$—, —C(CH$_3$)$_2$—, —C(CF$_3$)$_2$—, —S— or —SO$_2$—)

X—(CH$_2$)$_{z-2}$—CH═CH$_2$     [Formula M2]

(where X is a halide of Cl, Br, or I, —O—SO$_2$—CH$_3$, —O—SO$_2$—CF$_3$, —O—SO$_2$—C$_6$H$_4$—CF$_3$, —O—SO$_2$—C$_6$H$_4$—NO$_2$, or —O—SO$_2$—C$_6$H$_4$—CH$_3$, and z is an integer of 3 to 10)

[Intermediates (32)]

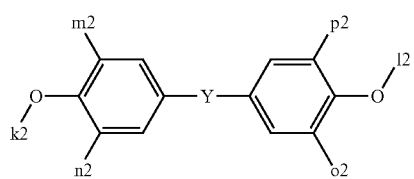
(A32)

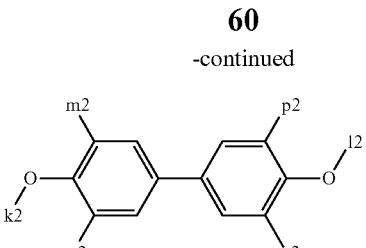
(B32)

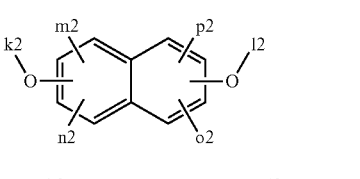
(C32)

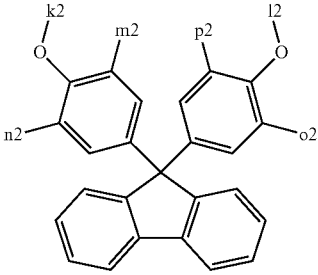
(D32)

(in Formulae A32 to D32, substituents k2 to p2 are —(CH$_2$)$_{Z-2}$CH═CH$_2$ (Z is an integer of 3 to 10), and in Formula A31, Y is —CH$_2$—, —C(CH$_3$)$_2$—, —C(CF$_3$)$_2$—, —S— or —SO$_2$—)

HSiR$_1$R$_2$R$_3$     [Formula M3]

(where at least one of R$_1$ to R$_3$ is C$_{1-10}$alkoxy, the other thereof is linear or branched C$_{1-10}$alkyl, and the alkoxy and the alkyl are linear or branched)

[Final Products]

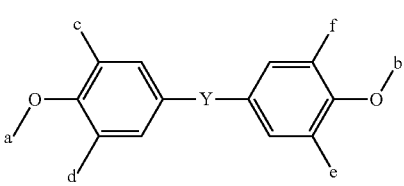
(AI)

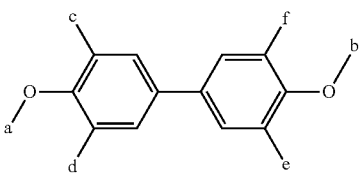
(BI)

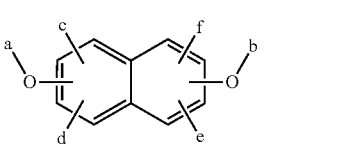
(CI)

-continued

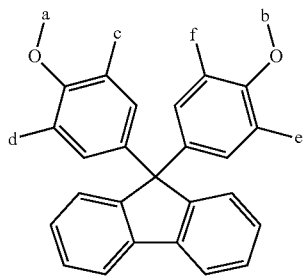

(DI)

(in Formulae AI to DI, at least two substituents of a to f are the following Formula S1, and the other thereof is —(CH$_2$)$_{Z-2}$CH═CH$_2$ (Z is an integer of 3 to 10), and in Formula AI, Y is —CH$_2$—, —C(CH$_3$)$_2$—, —C(CF$_3$)$_2$—, —S— or —SO$_2$—)

—(CH$_2$)$_z$—SiR$_1$R$_2$R$_3$         [Formula S1]

(in Formula S1, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the 3-3$^{rd}$ step, intermediates (32) in which a hydroxyl group is substituted with is —(CH$_2$)$_{Z-2}$CH═CH$_2$ (Z is an integer of 3 to 10) may be obtained by reacting the intermediates (31) prepared in 3-1$^{st}$ step with the alkenyl compound of Formula M2 in the presence of an optional base and an optional solvent.

The 3-3$^{rd}$ step may be performed by adding and reacting 0.5 to 10 equivalents of the —(CH$_2$)$_{Z-2}$CH═CH$_2$ (Z is an integer of 3 to 10) of the alkenyl compound of Formula M2 based on 1 equivalent of the hydroxyl group of the intermediates (31), and the reaction may be performed at 15° C. to 100° C. for 1 to 120 hours.

In the 3-3$^{rd}$ step, the base may include, without limitation, for example, KOH, NaOH, K$_2$CO$_3$, Na$_2$CO$_3$, KHCO$_3$, NaHCO$_3$, NaH, pyridine, triethylamine, and diisopropylethylamine. These bases may be used alone or as a combination of two or more thereof 0.1 to 5 equivalents of the base may be used based on 1 equivalent of the hydroxyl group of the intermediates (31) prepared in the 3-1$^{st}$ step in consideration of reaction efficiency.

In the 3-3$^{rd}$ step, solvents may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), H$_2$O, alcohols (methanol, ethanol), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

In the 3-4$^{th}$ step, the final products of Formulae AI to DI may be obtained by reacting the intermediates (32) prepared in the 3-3$^{rd}$ step with the alkoxysilane of Formula M3 in the presence of a metal catalyst and an optional solvent.

In the 3-4$^{th}$ step, the —(CH$_2$)$_{Z-2}$CH═CH$_2$ (Z is an integer of 3 to 10) of the intermediates (32) prepared in 3-3$^{rd}$ step react with alkoxysilane in an equivalent ratio according to stoichiometry, and 1 to 5 equivalents of the alkoxysilane of Formula M3 may be added and reacted based on 1 equivalent of the —(CH$_2$)$_{Z-2}$CH═CH$_2$ (Z is an integer of 3 to 10) of the intermediates (32) prepared in 3-3$^{rd}$ step, and the reaction may be performed at 15° C. to 120° C. for 1 to 72 hours.

In the reaction of the 3-4$^{th}$ step, the metal catalyst may include a platinum catalyst, for example, PtO$_2$ or chloroplatinic acid (H$_2$PtCl$_6$), without limitation. 0.005 to 0.05 equivalents of the platinum catalyst may preferably be used based on 1 equivalent of the —(CH$_2$)$_{Z-2}$CH═CH$_2$ (Z is an integer of 3 to 10) of the intermediates (31) prepared in the 3-1$^{st}$ step in consideration of reaction efficiency.

In the 3-4$^{th}$ step, solvents may be optionally used as occasion demands. In the 3-4$^{th}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

J. Method for preparing alkoxysilyl compound, by which starting materials (Formulae AS to DS) of which all substituents are hydrogen are alkenylated, and rearrangement reaction is performed twice to have two substituents of —CONH(CH$_2$)$_Z$—SiR$_1$R$_2$R$_3$ and four alkenyl groups (Method 10)

An alkoxysilyl compound having two substituents of —CONH(CH$_2$)$_Z$—SiR$_1$R$_2$R$_3$ and four —(CH$_2$)$_{Z-2}$CH═CH$_2$ (Z is an integer of 3 to 10) groups may be prepared by additionally combining the substituent of —CONH(CH$_2$)$_Z$—SiR$_1$R$_2$R$_3$ with the intermediates (31) prepared in the 3-1$^{st}$ step in method 8.

Particularly, by performing a 3-5$^{th}$ step by reacting the intermediates (31) prepared by the 3-1$^{st}$ step of method 8 with the isocyanate-based alkoxysilane of the following Formula M1 in the presence of an optional base and an optional solvent, one of final products of the following Formulae AI to DI may be prepared.

[Intermediates (31)]

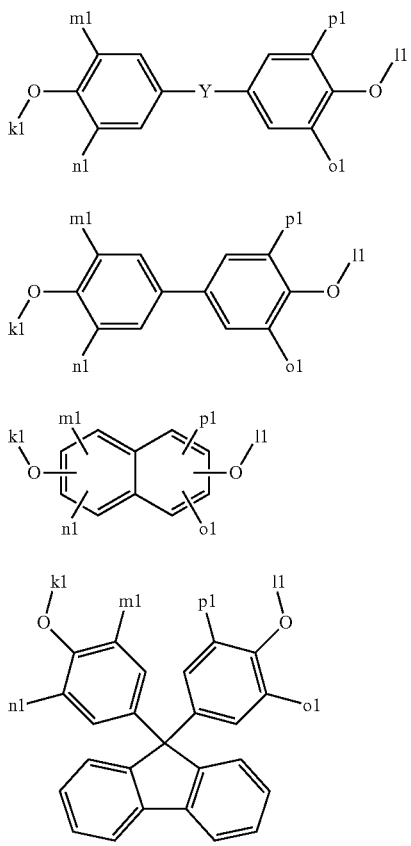

(in Formulae A31 to D31, substituents k1 and l1 are hydrogen, and m1 to p1 are —(CH$_2$)$_{Z-2}$CH=CH$_2$ (Z is an integer of 3 to 10), and in Formula A31, Y is —CH$_2$—, —C(CH$_3$)$_2$—, —C(CF$_3$)$_2$—, —S— or —SO$_2$—)

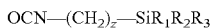

(where at least one of R$_1$ to R$_3$ is C$_{1-10}$alkoxy, the other thereof is linear or branched C$_{1-10}$alkyl, the alkoxy and the alkyl are linear or branched, and z is an integer of 3 to 10)

[Final Products]

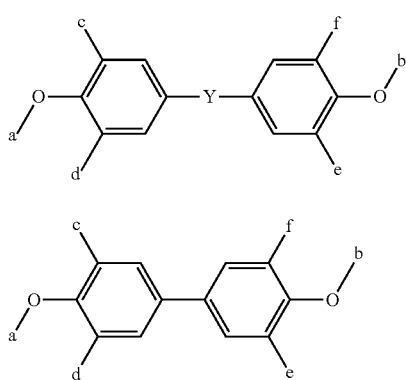

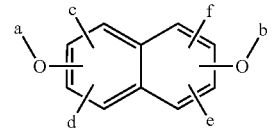

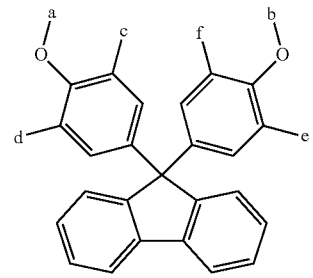

(in Formulae AI to DI, substituents a and b are the following Formula S1, and c to f are —(CH$_2$)$_{Z-2}$CH=CH$_2$ (Z is an integer of 3 to 10), and in Formula AI, Y is —CH$_2$—, —C(CH$_3$)$_2$—, —C(CF$_3$)$_2$—, —S— or —SO$_2$—)

—CONH(CH$_2$)$_z$—SiR$_1$R$_2$R$_3$            [Formula S2]

(in Formula S2, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the 3-5$^{th}$ step, an alkoxysilyl compound may be prepared by reacting 1 to 5 equivalents of the isocyanate-based alkoxysilane of the following Formula M1 based on 1 equivalent of the hydroxyl group of the intermediates (31) in the presence of an optional base and an optional solvent. In addition, such a reaction may be performed at 15° C. to 120° C. for 1 to 72 hours.

In the 3-5$^{th}$ step, the base used may include, without limitation, for example, K$_2$CO$_3$, Na$_2$CO$_3$, KHCO$_3$, NaHCO$_3$, NaH, pyridine, triethylamine, and diisopropylethylamine. These bases may be used alone or as a combination of two or more thereof. 0.1 to 5 equivalents of the base may be used based on 1 equivalent of the hydroxyl group of the intermediates (31) in consideration of reaction efficiency.

In the 3-5$^{th}$ step, solvents may be optionally used as occasion demands. When the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

K. Method for preparing alkoxysilyl compound, by which starting materials (Formulae AS to DS) of which all substituents are hydrogen are alkenylated, and rearrangement reaction is performed twice to have two substituents of —CONH(CH$_2$)$_Z$—SiR$_1$R$_2$R$_3$ and at least two substituents of —(CH$_2$)$_Z$—SiR$_1$R$_2$R$_3$ (Method 11)

An alkoxysilyl compound having two substituents of —CONH(CH$_2$)$_Z$—SiR$_1$R$_2$R$_3$ and at least two substituents of —(CH$_2$)$_Z$—SiR$_1$R$_2$R$_3$ groups may be prepared by additionally combining the substituent of —(CH$_2$)$_Z$—SiR$_1$R$_2$R$_3$ with the alkoxysilyl compound prepared in method 10.

Particularly, one of final products of the following Formulae AI to DI may be prepared by performing a 3-6$^{th}$ step in which one of the alkoxysilyl compounds prepared in method 10 reacts with the alkoxysilane of the following Formula M3 in the presence of a metal catalyst and an optional solvent.

HSiR$_1$R$_2$R$_3$      [Formula M3]

(where at least one of R$_1$ to R$_3$ is C$_{1-10}$alkoxy, the other thereof is linear or branched C$_{1-10}$alkyl, and the alkoxy and the alkyl are linear or branched)

[Final Products]

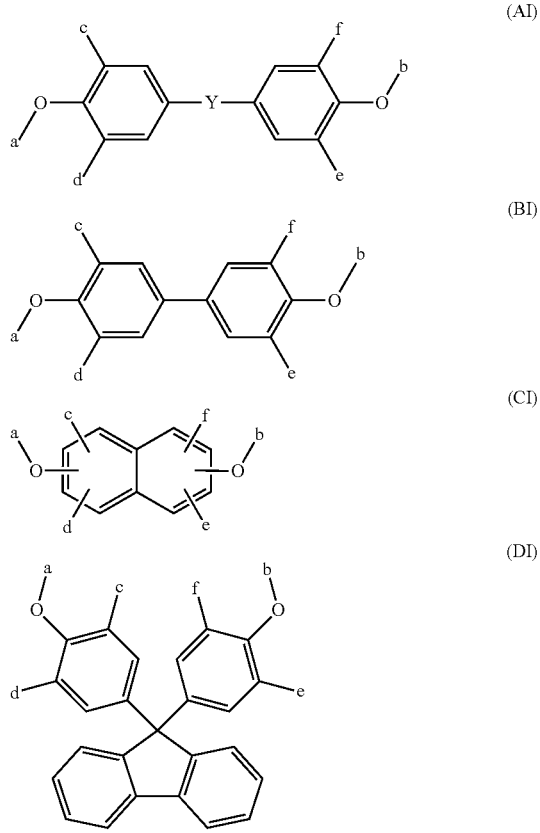

(in Formulae AI to DI, substituents a and b are the following Formula S2, at least two of c to f are the following Formula S1, and the other thereof is —(CH$_2$)$_{Z-2}$CH═CH$_2$ (Z is an integer of 3 to 10), and in Formula AI, Y is —CH$_2$—, —C(CH$_3$)$_2$—, —C(CF$_3$)$_2$—, —S— or —SO$_2$—)

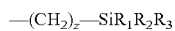

—(CH$_2$)$_z$—SiR$_1$R$_2$R$_3$      [Formula S1]

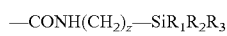

—CONH(CH$_2$)$_z$—SiR$_1$R$_2$R$_3$      [Formula S2]

(in Formulae S1 and S2, at least one of R$_1$ to R$_3$ is C$_{1-10}$alkoxy, the other thereof is C$_{1-10}$alkyl, the alkoxy and the alkyl are linear or branched, and z is an integer of 3 to 10)

In the 3-6$^{th}$ step, the —(CH$_2$)$_{Z-2}$CH═CH$_2$ (Z is an integer of 3 to 10) of the alkoxysilyl compounds prepared in method 10 reacts with an alkoxysilane in an equivalent ratio according to stoichiometry, and 1 to 5 equivalents of the alkoxysilane of Formula M3 may be added and reacted based on 1 equivalent of the —(CH$_2$)$_{Z-2}$CH═CH$_2$ (Z is an integer of 3 to 10) of the alkoxysilyl compound prepared in method 10. The reaction may be performed at 15° C. to 120° C. for 1 to 72 hours.

In the reaction of the 3-6$^{th}$ step, the metal catalyst may include a platinum catalyst, for example, PtO$_2$ or chloroplatinic acid (H$_2$PtCl$_6$), without limitation. 0.005 to 0.05 equivalents of the platinum catalyst may preferably be used based on 1 equivalent of the —(CH$_2$)$_{Z-2}$CH═CH$_2$ (Z is an integer of 3 to 10) of the alkoxysilyl compounds prepared in method 10 in consideration of reaction efficiency.

In the 3-6$^{th}$ step, solvents may be optionally used as occasion demands. In the 3-6$^{th}$ step, when the viscosity of the reactants at the reaction temperature is appropriate for conducting the reaction without a separate solvent, the solvent may not be used. That is, when the viscosity of the reactants is sufficiently decreased that the mixing and the stirring of the reactants may be conducted smoothly without a solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used. These solvents may be used alone or as a mixture of two or more thereof. The amount of the solvent may not be limited to being within a specific range, and an appropriate amount of the solvent may be used within a range for sufficiently dissolving the reactants and not adversely affecting the reaction. A person skilled in the art may select an appropriate amount of a solvent considering the above-mentioned points.

Hereinafter, the present invention will be explained more particularly with reference to preferred embodiments. The following embodiments are only illustrative to assist the understanding of the present invention, and the scope of the present invention is not limited thereto.

Synthetic Example 1

Synthesis of Bisphenol A-Based Alkoxysilyl Compound (Compound AI) (Hydrosilylation, A-1) (Method 2)

(1) First Step

To a two-necked flask, 25 g of bisphenol A (A), 39.7 g of allyl bromide, and 400 ml of tetrahydrofuran (THF) were added and stirred at room temperature. Then, a NaOH solution prepared by dissoving 10.5 g of NaOH in 400 ml of H$_2$O was slowly added thereto at room temperature for 1 hour, followed by further stirring for 4 hours. After that, THF was removed by using an evaporator, and the reaction product was worked-up by adding 400 ml of ethyl acetate with H$_2$O to remove inorganic materials. To an organic layer, MgSO$_4$ was added to remove remaining H$_2$O, and the organic layer was filtered using a celite filter and dried by evaporation to obtain an intermediate.

(2) Second Step

To a flask, 10 g of the intermediate, 0.15 g of $PtO_2$, 11.7 g of triethoxysilane, and 150 ml of toluene were added and stirred at room temperature for 5 minutes. Then, the temperature was elevated to 80° C., and heating and stirring were continued for 12 hours. Then, the reaction product was cooled to room temperature and filtered using a celite filter to remove inorganic materials. Toluene was removed by evaporation and drying, and the product thus obtained was completely dried using a vacuum pump to obtain a final product (A-1).

The synthetic reaction of Synthetic Example 1 is as follows.

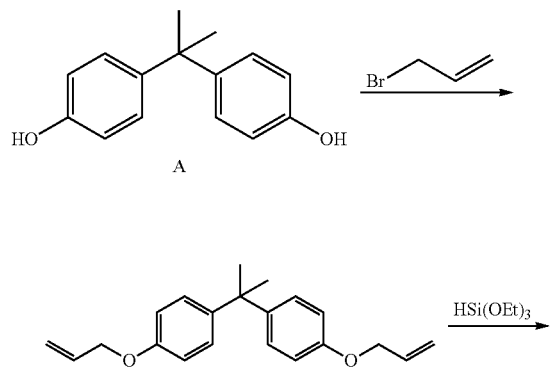

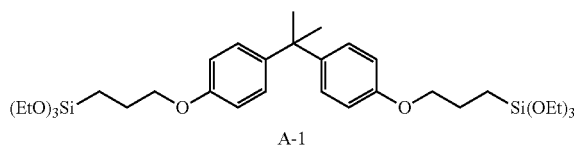

A-1

Synthetic Examples 2 to 7

Alkoxysilyl Compounds (Hydrosilylation, B-1 to G-1) (Method 2)

Alkoxysilyl compounds of Formulae B-1 to G-1 were synthesized by performing a first step reaction and a second step reaction according to the same method described in Synthetic Example 1 except for the amounts used of reactants. Each amount of the reactants used in the first step and the second step is shown in Table 1 and Table 2 below.

TABLE 1

| Synthetic example | Starting material | Allyl bromide | THF | NaOH (in 400 ml $H_2O$) |
|---|---|---|---|---|
| 2 | Biphenyl-4,4'-diol | 48.7 g | 400 ml | 12.9 g |
| 3 | Naphthalene-2,7-diol | 56.6 g | 400 ml | 15.0 g |
| 4 | 4,4'-(9H-fluorene-9,9' diyl)diphenol | 25.9 g | 400 ml | 6.8 g |
| 5 | 4,4',4''-methanetriyltriphenol | 46.6 g | 400 ml | 12.3 g |
| 6 | 4,4',4'',4'''-(ethane-1,1,2,2-tetrayl)tetraphenol | 45.5 g | 400 ml | 12.0 g |
| 7 | 1,1'-methylenedinaphthalene-2,7-diol | 54.6 g | 400 ml | 14.4 g |

TABLE 2

| Synthetic example | Intermediate synthesized in the first step | $PtO_2$ | $HSi(OEt)_3$ | Toluene | Final compound |
|---|---|---|---|---|---|
| 2 | 10 g | 0.17 g | 13.6 g | 150 ml | B-1 |
| 3 | 10 g | 0.19 g | 15.0 g | 150 ml | C-1 |
| 4 | 10 g | 0.11 g | 8.4 g | 150 ml | D-1 |
| 5 | 10 g | 0.11 g | 13.1 g | 150 ml | E-1 |
| 6 | 10 g | 0.08 g | 12.9 g | 150 ml | F-1 |
| 7 | 10 g | 0.09 g | 14.7 g | 150 ml | G-1 |

Synthetic Reaction of Synthetic Example 2

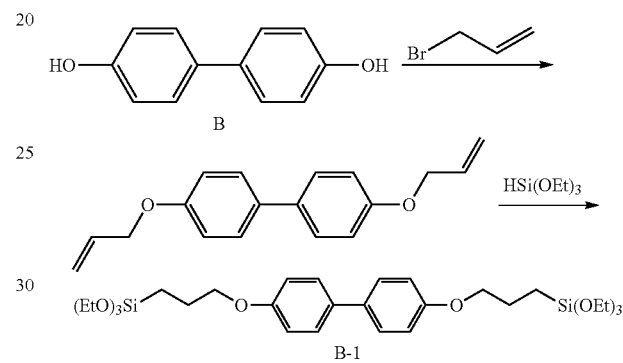

Synthetic Reaction of Synthetic Example 3

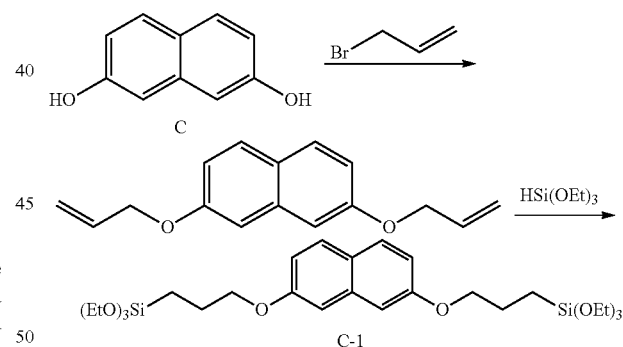

Synthetic Reaction of Synthetic Example 4
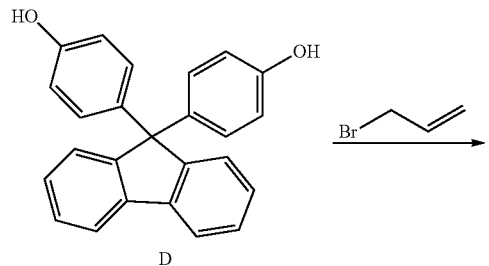
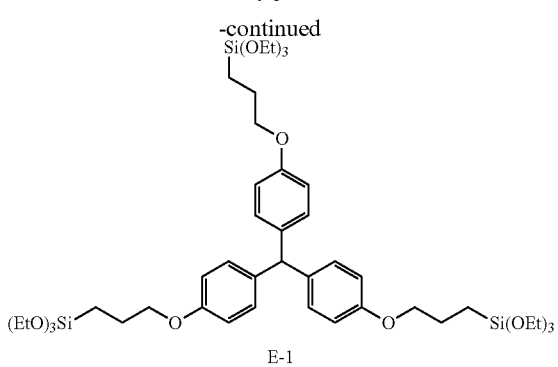
Synthetic Reaction of Synthetic Example 5
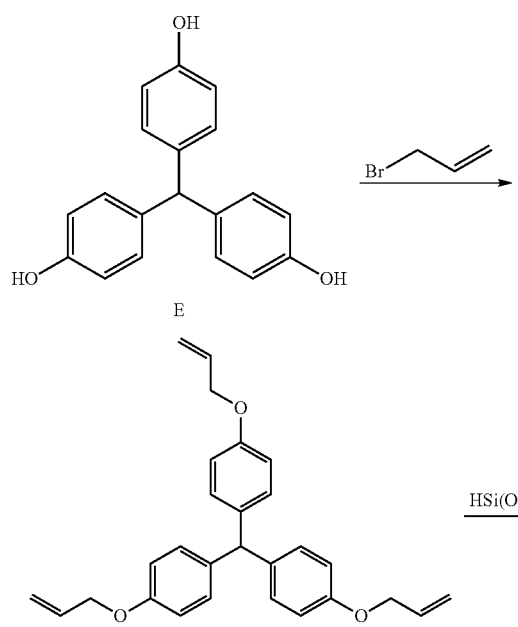
Synthetic Reaction of Synthetic Example 6
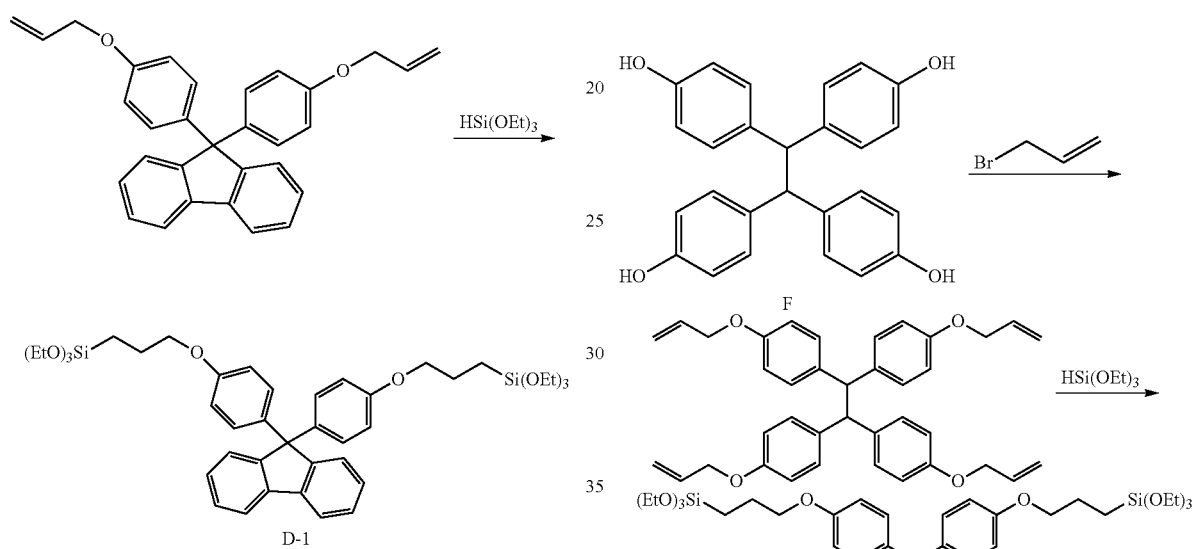
Synthetic Reaction of Synthetic Example 7
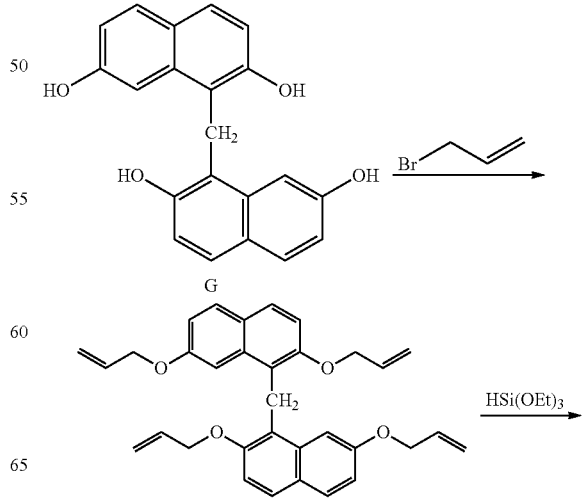

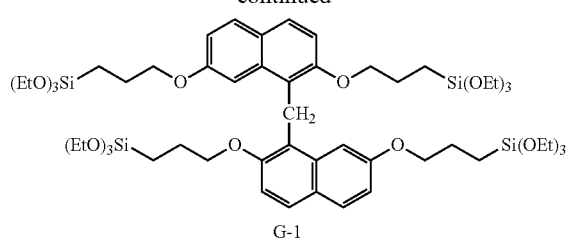

G-1

Synthetic Example 8

Diaminodiphenylmethane-Based Alkoxysilyl Compound (Hydrosilylation, H-1) (Method 2)

(1) First Step

To a two-necked flask, 20 g of diaminodiphenylmethane (I), and 400 ml of CH$_3$CN were added and stirred at room temperature, and then, 73.2 g of allyl bromide was added thereto at 0° C. Then, 47.9 g of pyridine was slowly added thereto for 1 hour, and stirred and reacted at 80° C. for 2 hours. After finishing the reaction, solvents were removed by using an evaporator, and the reaction product was worked-up by using 400 ml of ethyl acetate with a 1 M NaOH solution. An organic layer was separated, MgSO$_4$ was added to the organic layer to remove remaining H$_2$O, and the organic layer was filtered and evaporated to obtain an intermediate.

(2) Second Step

To a flask, 10 g of the intermediate, 0.13 g of PtO$_2$, 20.2 g of triethoxysilane, and 150 ml of toluene were added and stirred at room temperature for 5 minutes. Then, the temperature was elevated to 80° C., and heating and stirring were continued for 12 hours. Then, the reaction product was cooled to room temperature and filtered using a celite filter to remove inorganic materials. Toluene was removed by evaporation and drying, and the product thus obtained was completely dried using a vacuum pump to obtain a final product (H-1).

The synthetic reaction of Synthetic Example 8 is as follows.

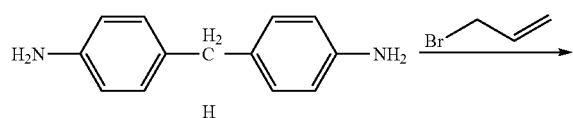

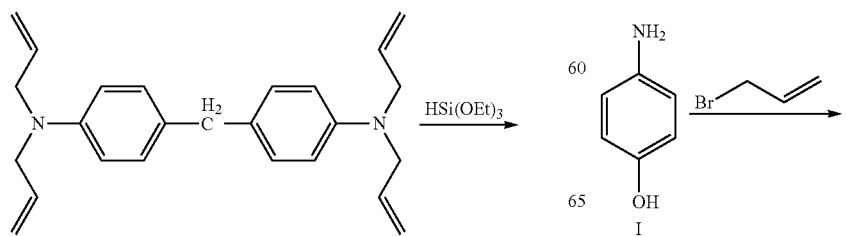

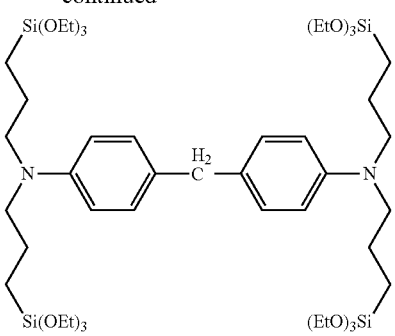

H-1

Synthetic Example 9

Aminophenol-Based Alkoxysilyl Compound (Hydrosilylation, I-1) (Method 2)

(1) First Step

To a two-necked flask, 25 g of aminophenol (I), 124.7 g of allyl bromide, and 400 ml of tetrahydrofuran (THF) were added and stirred at room temperature. Then, a NaOH solution prepared by dissoving 33.0 g of NaOH in 400 ml of H$_2$O was slowly added thereto for 1 hour at room temperature, and stirred further for 4 hours. After that, THF was removed by using an evaporator, and the reaction product was worked-up by adding 400 ml of ethyl acetate with H$_2$O to remove inorganic materials. To an organic layer, MgSO$_4$ was added to remove remaining H$_2$O, and the organic layer was filtered using a celite filter and dried by evaporation to obtain an intermediate.

(2) Second Step

To a flask, 10 g of the intermediate, 0.20 g of PtO$_2$, 23.6 g of triethoxysilane, and 150 ml of toluene were added and stirred at room temperature for 5 minutes. Then, the temperature was elevated to 80° C., and heating and stirring were continued for 12 hours. Then, the reaction product was cooled to room temperature and filtered using a celite filter to remove inorganic materials. Toluene was removed by evaporation and drying, and the product thus obtained was completely dried using a vacuum pump to obtain a final product (I-3).

The synthetic reaction of Synthetic Example 9 is as follows.

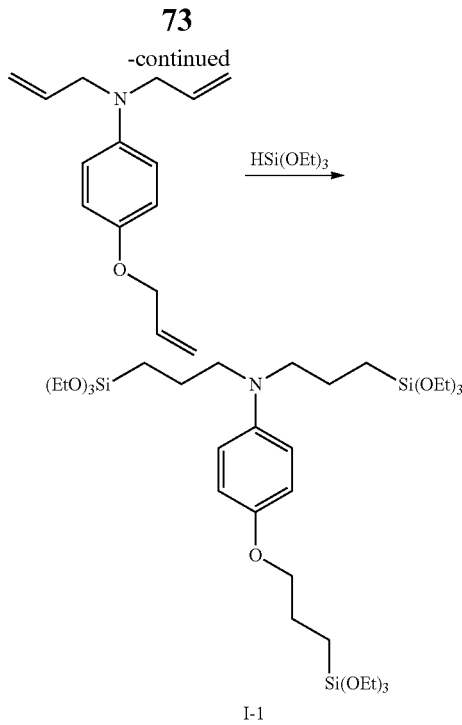

I-1

Synthetic Example 10

Bisphenol A-Based Alkoxysilyl Compound (Carbamate, A-2) (Method 1)

To a flask, 25 g of bisphenol A (A), 34.0 g of diisopropylethylamine (DIPEA), and 200 ml of methylene chloride were added and stirred at room temperature for 5 minutes. Then, 54.2 g of triethoxysilyl propyl isocyanate was added thereto at room temperature, and the temperature was elevated to 60° C., followed by performing reaction for 12 hours. After finishing the reaction, the reaction product was cooled to room temperature and worked-up using $H_2O$. An organic layer was separated, and remaining $H_2O$ was removed by adding $MgSO_4$. The organic layer was filtered using a celite filter and dried by evaporation to obtain a final product (A-2).

The synthetic reaction carried out in Synthetic Example 10 is as follows.

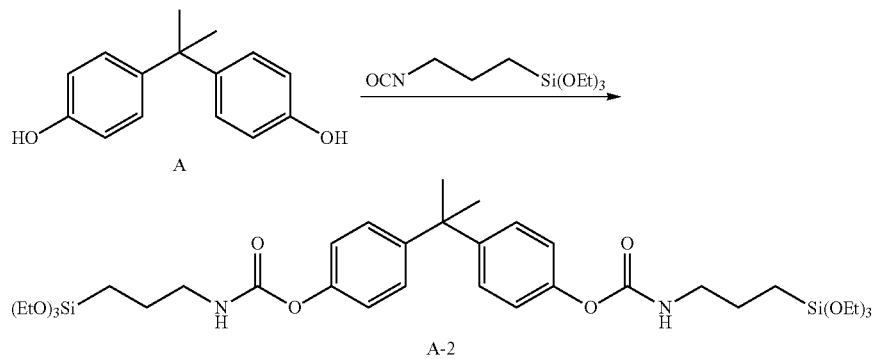

Synthetic Examples 11 to 16

Alkoxysilyl Compounds (Carbamate, B-2 to G-2) (Method 1)

Alkoxysilyl compounds of Formulae B-2 to G-2 were synthesized by performing the same method described in Synthetic Example 10 except for the amounts used of reactants. The amounts of the reactants used in each synthetic step are shown in the following table.

TABLE 3

| Synthetic example | Starting material | DIPEA | Methylene chloride | Triethoxysilyl propyl isocyanate | Final product |
|---|---|---|---|---|---|
| 11 | Biphenyl-4,4'-diol | 41.6 g | 200 ml | 66.4 g | B-2 |
| 12 | Naphthalene-2,7-diol | 48.4 g | 200 ml | 77.2 g | C-2 |
| 13 | 4,4'-(9H-fluorene-9,9'diyl)diphenol | 22.1 g | 200 ml | 35.3 g | D-2 |
| 14 | 4,4',4''-methanetriyltriphenol | 39.8 g | 200 ml | 64.5 g | E-2 |
| 15 | 4,4',4'',4'''-(ethane-1,1,2,2-terayl) tetraphenol | 38.9 g | 200 ml | 62.1 g | F-2 |
| 16 | 1,1'-methylenedinaphthalene-2,7-diol | 46.7 g | 200 ml | 74.4 g | G-2 |

The synthetic reaction carried out in Synthetic Example 11 is as follows.
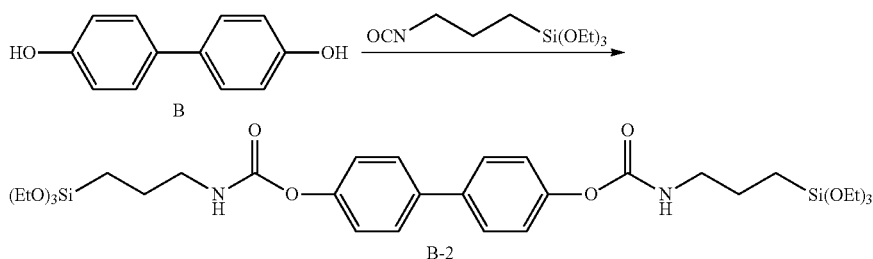
The synthetic reaction carried out in Synthetic Example 12 is as follows.
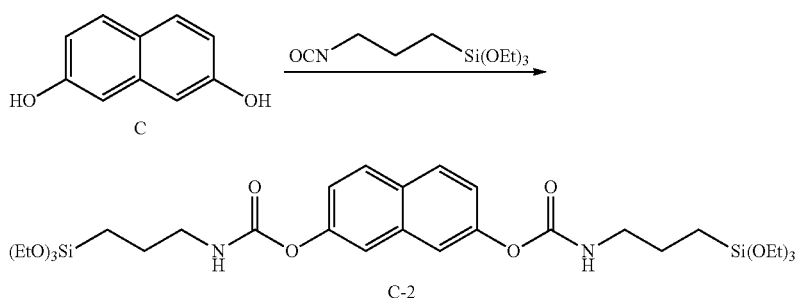
The synthetic reaction carried out in Synthetic Example 13 is as follows.
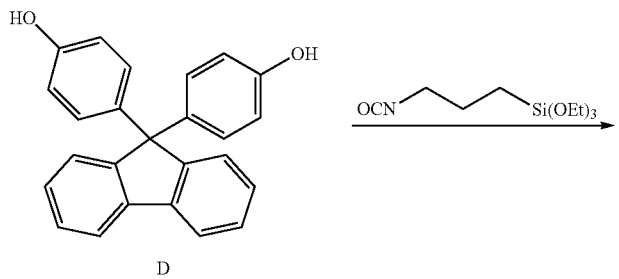
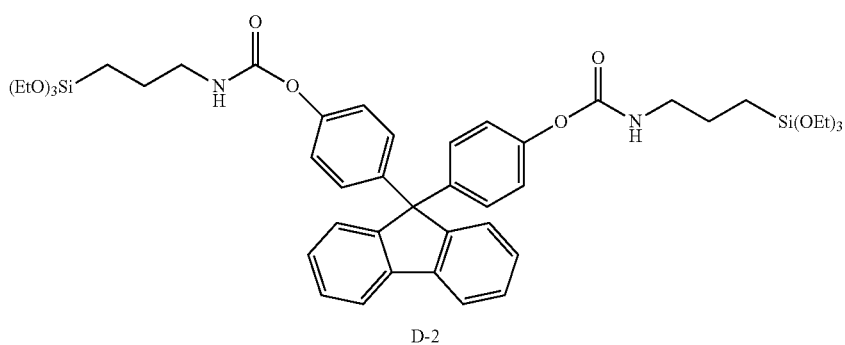
The synthetic reaction carried out in Synthetic Example 14 is as follows.

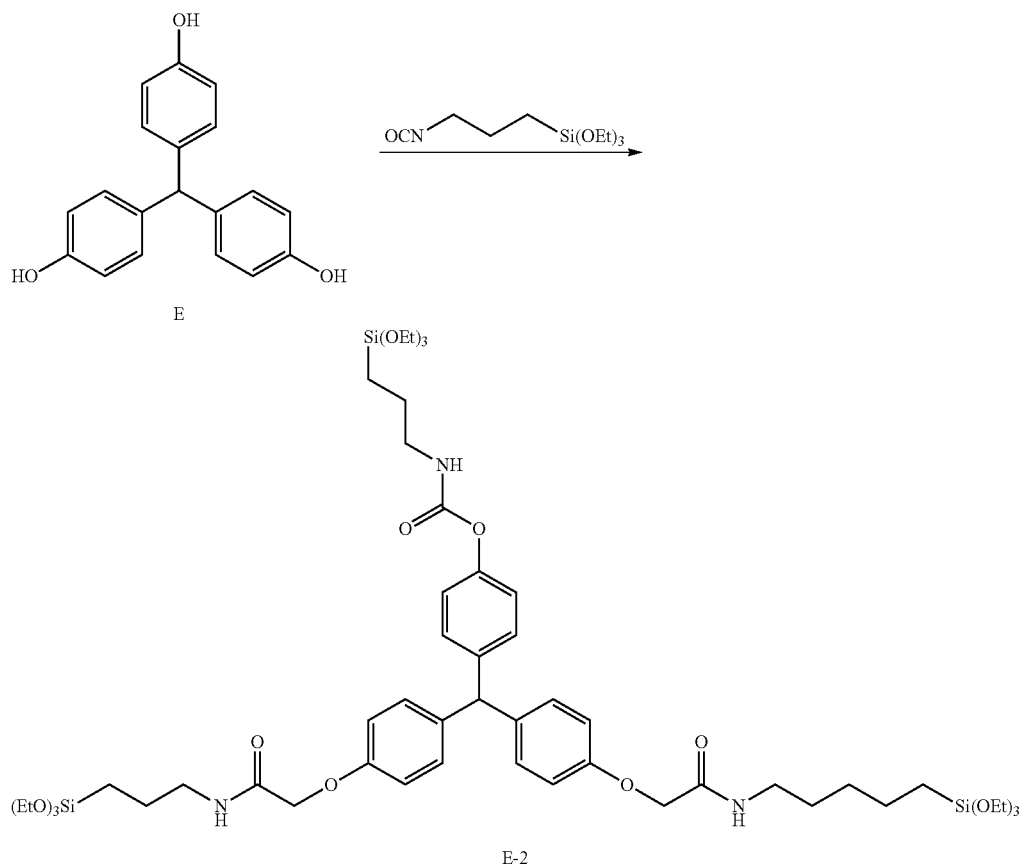
The synthetic reaction carried out in Synthetic Example 15 is as follows.
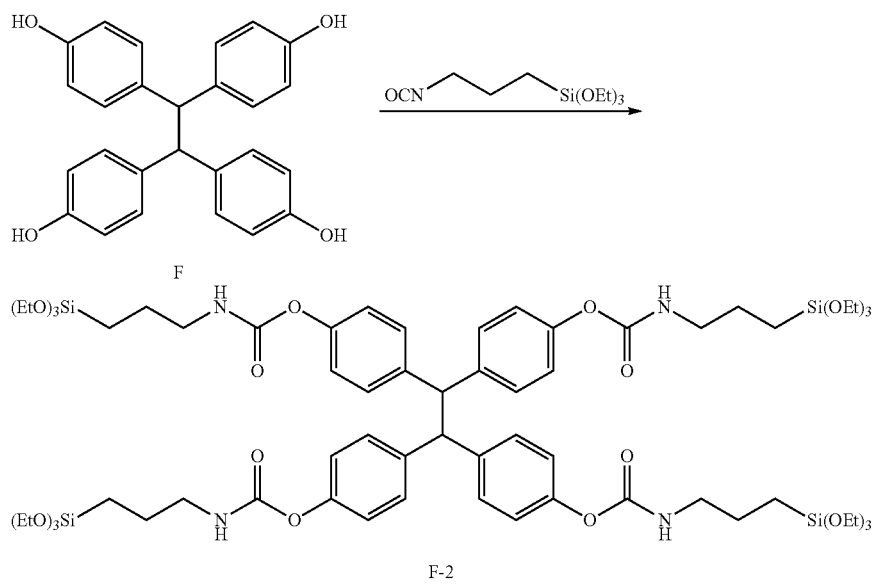
The synthetic reaction carried out in Synthetic Example 16 is as follows.

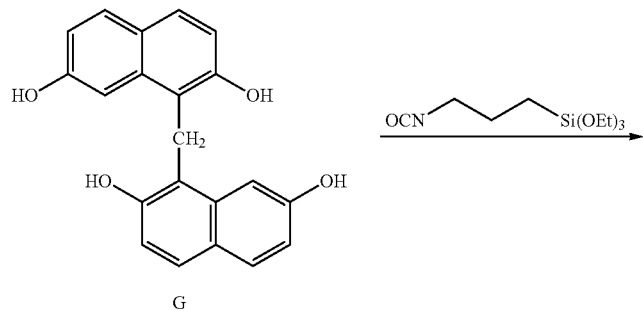

G

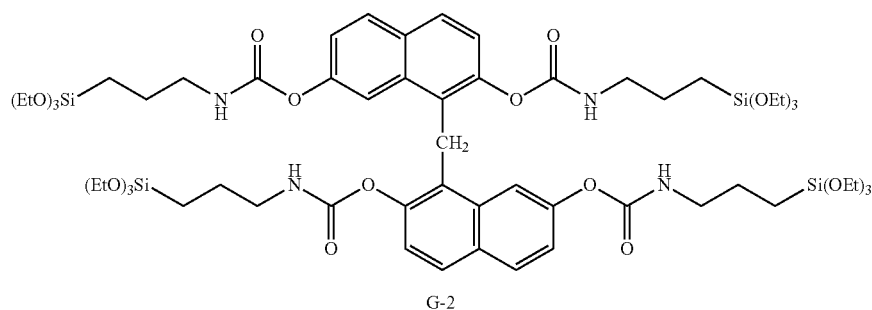

G-2

Synthetic Example 17

Diaminodiphenylmethane-based Alkoxysilyl Compound (Carbamate, H-2) (Method 1)

To a flask, 25 g of diaminodiphenylmethane (H), 97.8 g of diisopropylethylamine (DIPEA), and 200 ml of methylene chloride were added and stirred at room temperature. Then, 374.3 g of triethoxysilyl propyl isocyanate was added thereto at room temperature for 30 minutes, and the reaction was further performed for 30 minutes at room temperature. After removing solvents by using an evaporator, the temperature was elevated to 80° C., and the reaction was performed for 12 hours. After finishing the reaction, the reaction product was cooled to room temperature and worked-up using H$_2$O. An organic layer was separated, and remaining H$_2$O was removed by adding MgSO$_4$. The organic layer was filtered using a celite filter and dried by evaporation to obtain a final product (H-2).

The synthetic reaction carried out in Synthetic Example 17 is as follows.

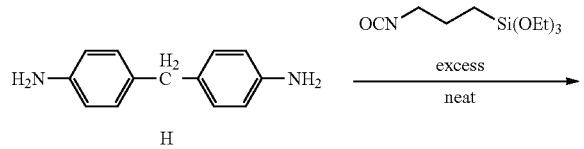

H

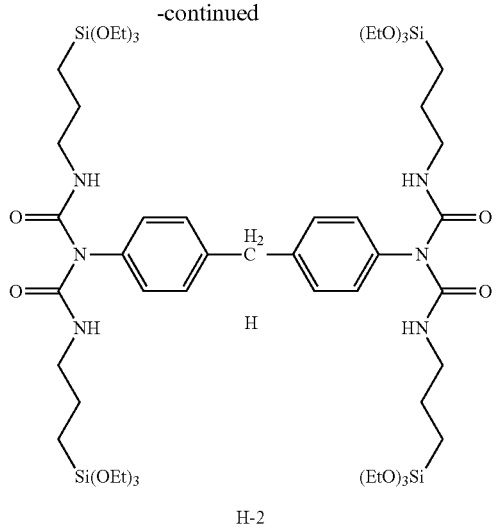

H-2

Synthetic Example 18

Aminophenol-Based Alkoxysilyl Compound (Carbamate, 1-2) (Method 1)

To a flask, 10 g of aminophenol (I), 28.4 g of per diisopropylethylamine (DIPEA), and 400 ml of methylene chloride were added and stirred at room temperature. Then, 45.3 g of triethoxysilyl propyl isocyanate was added thereto at room temperature for 30 minutes, and the reaction was further performed for 30 minutes at room temperature. After that, the temperature was elevated to 60° C., and the reaction was performed for 12 hours. After finishing the reaction, the reaction product was cooled to room temperature and worked-up using H₂O. An organic layer was separated, and remaining H₂O was removed by adding MgSO₄. The organic layer was filtered using a celite filter and dried by evaporation to obtain a final product (I-2).

The synthetic reaction carried out in Synthetic Example 18 is as follows.

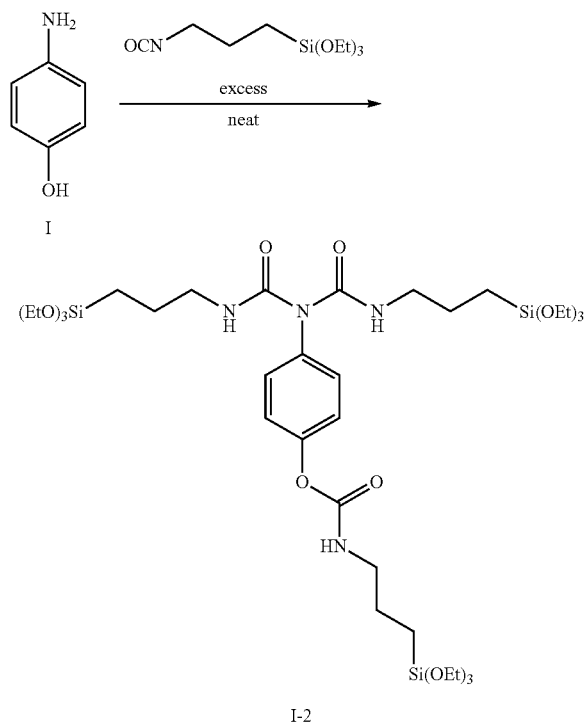

Synthetic Example 19

Bisphenol A-Based Alkoxysilyl Compound (Hydrosilylation, A-3) (Method 5)

(1) First Step

An intermediate was obtained by conducting the same reaction as the reaction of the first step in Synthetic Example 1.

(2) Second Step

To a flask, 10 g 4,4'-(propane-2,2-diyl)bis(allyloxybenzene) as the intermediate of the first step was added and reacted at 180° C. for 8 hours to achieve rearrangement (Claisen rearrangement) and to obtain 4,4'-(propane-2,2-diyl)bis(2-allylphenol).

(3) Third Step

To a two-necked flask, a reflux condenser was installed, and 9 g of the intermediate of the second step, 4,4'-(propane-2,2-diyl)bis(2-allylphenol) was dissolved in acetone at 80° C. Then, 6.4 ml of allyl bromide and 24.7 g of K₂CO₃ were added thereto and stirred at 80° C. for 24 hours. The product thus obtained was cooled to room temperature and filtered using a celite filter, and solvents were removed by evaporation to obtain a reaction product. The reaction product was dissolved in ethyl acetate and washed with water and a brine solution. An organic solvent layer was dried with MgSO₄ and filtered, and solvents were removed by using an evaporator to obtain 4,4'-(propane-2,2-diyl)bis(2-allyl-1-(allyloxy)benzene) having four allyl groups.

(4) Fourth Step

To a flask, 10 g of the intermediate of the third step, 0.23 g of PtO₂, 22.1 ml of triethoxysilane, and 150 ml of toluene were added and stirred at room temperature for 5 minutes. Then, the temperature was elevated to 85° C. and stirring was performed for 36 hours. Then, the reaction product was cooled to room temperature and filtered using a celite filter to remove inorganic materials. Toluene was removed by evaporation and drying, and the product thus obtained was completely dried using a vacuum pump to obtain a final product (A-3).

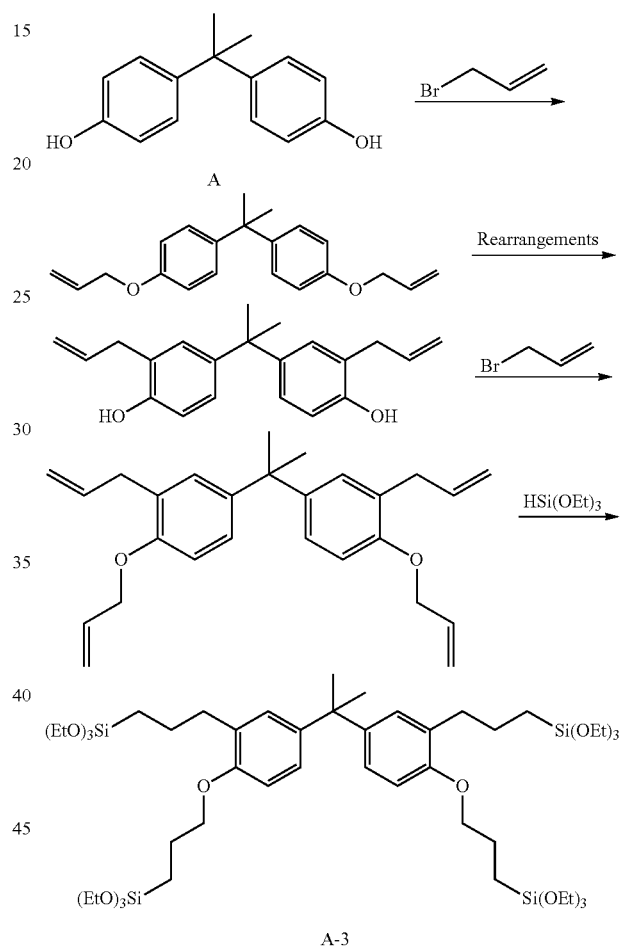

The synthetic reaction carried out in Synthetic Example 19 is as follows.

Synthetic Examples 20 to 22

Alkoxysilyl Compounds (Hydrosilylation, B-3 to D-3) (Method 5)

Alkoxysilyl compounds of Formulae B3 to D3, having four alkoxysilyl groups were synthesized by performing the first step to the fourth step according to the same method as Synthetic Example 19 except for the amounts used of the reactants. The amounts used in the third step and the fourth step are shown in Table 4 and Table 5 below.

TABLE 4

| Synthetic example | Compound having two allyl groups produced in the second step reaction | Allyl bromide | Acetone | $K_2CO_3$ |
|---|---|---|---|---|
| 20 | 10 g | 11.4 g | 150 ml | 31.1 g |
| 21 | 10 g | 12.6 g | 150 ml | 34.5 g |
| 22 | 10 g | 7.0 g | 150 ml | 19.3 g |

TABLE 5

| Synthetic example | Compound having four allyl groups produced in the third step reaction | $PtO_2$ | $HSi(OEt)_3$ | Toluene | Final product |
|---|---|---|---|---|---|
| 20 | 10 g | 0.26 g | 19.9 g | 150 ml | B-3 |
| 21 | 10 g | 0.28 g | 21.5 g | 150 ml | C-3 |
| 22 | 10 g | 0.18 g | 13.5 g | 150 ml | D-3 |

The synthetic reaction carried out in Synthetic Example 20 is as follows.

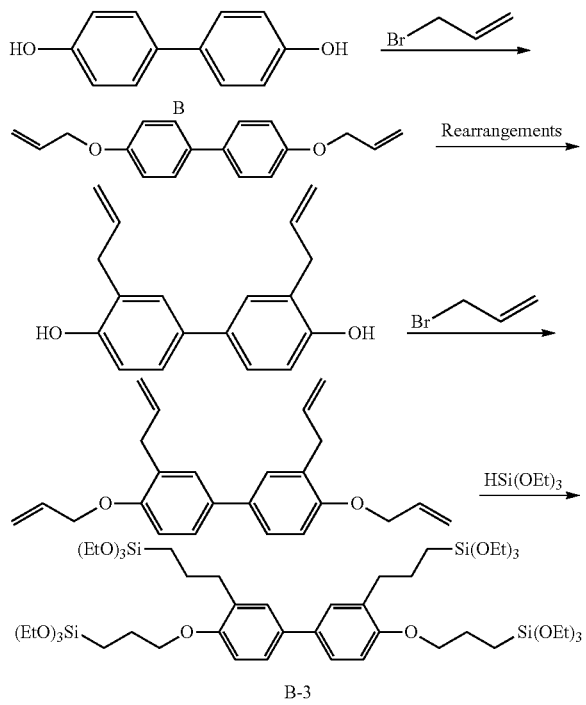

The synthetic reaction carried out in Synthetic Example 21 is as follows.

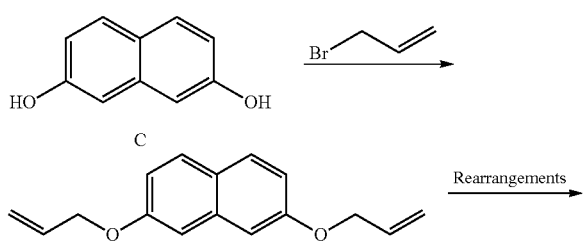

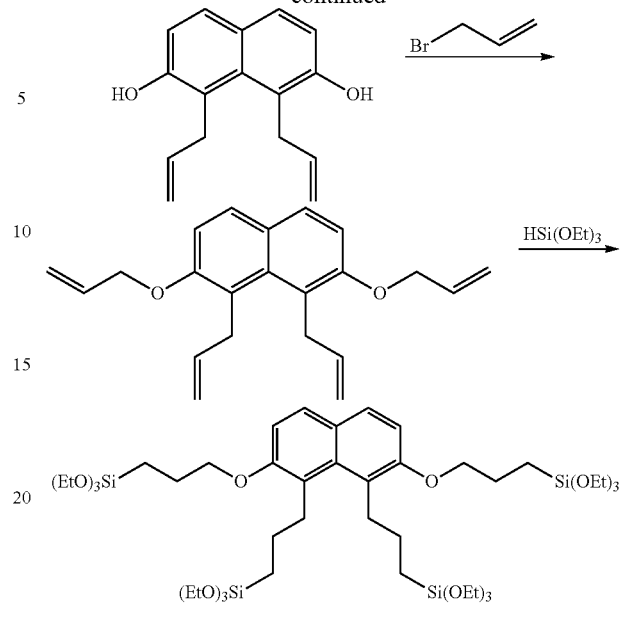

The synthetic reaction carried out in Synthetic Example 22 is as follows.

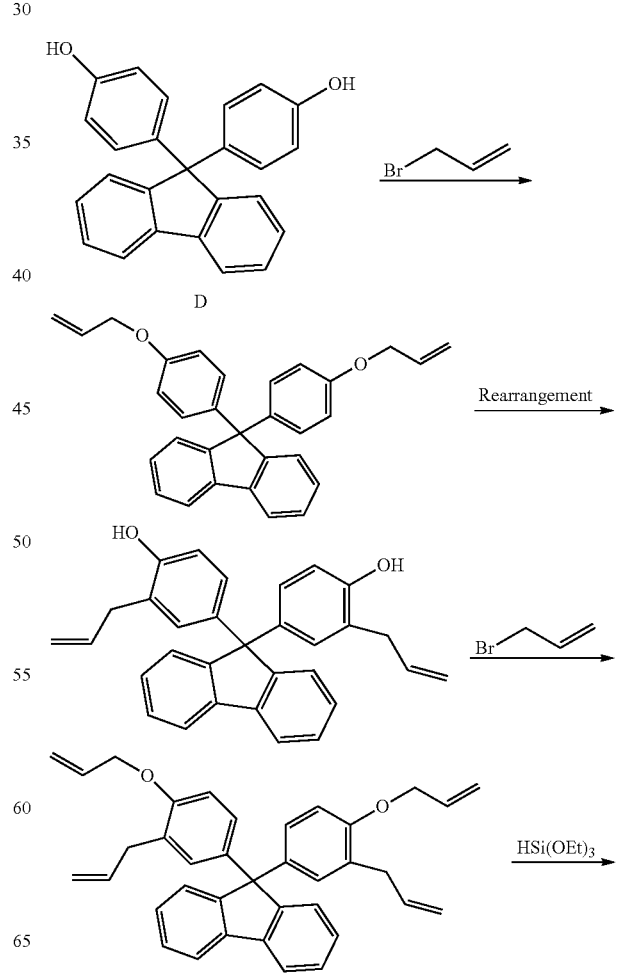

-continued

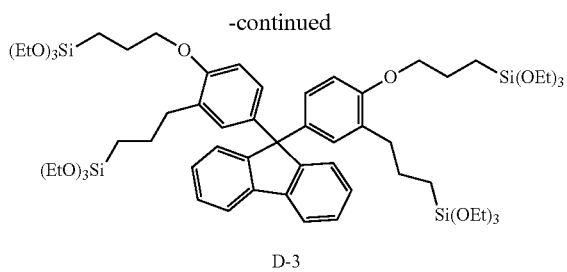

D-3

Synthetic Example 23

Bisphenol A-Based Alkoxysilyl Compound Having Allyl Group (Carbamate, A-4) (Method 6)

(1) First Step and Second Step

An intermediate of 4,4'-(propane-2,2-diyl)bis(2-allylphenol) having two allyl groups was obtained by performing the same reaction as the first step and the second step in Synthetic Example 19.

(2) Third Step

To a flask, 10 g of the intermediate of 4,4'-(propane-2,2-diyl)bis(2-allylphenol), 10.1 g of per diisopropylethylamine (DIPEA), and 300 ml of methylene chloride were added and stirred at room temperature. Then, 16.0 g of triethoxysilyl propyl isocyanate ($OCN(CH_2)_3Si(OEt)_3$) was added thereto at room temperature for 5 minutes, the temperature was elevated to 80° C., and the reaction was performed for 12 hours. After finishing the reaction, the reaction product was cooled to room temperature and worked-up using $H_2O$ to separate an organic layer. $MgSO_4$ was added to the organic layer for removing remaining $H_2O$, and the organic layer was filtered using a celite filter and evaporated to obtain a final product (A-4).

The synthetic reaction carried out in Synthetic Example 23 is as follows.

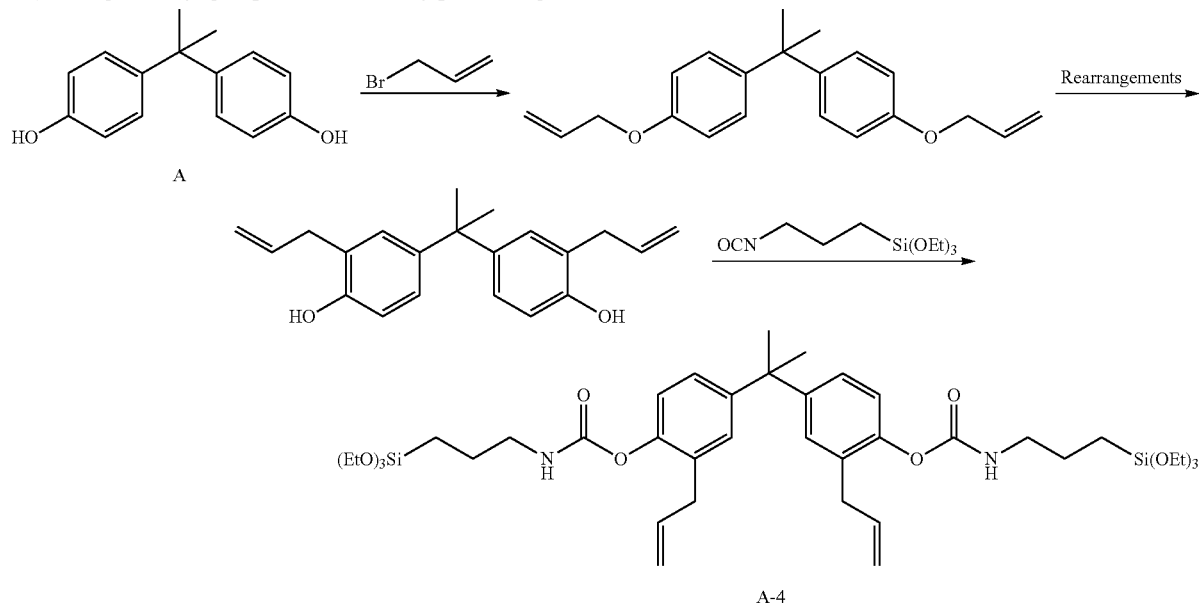

Synthetic Examples 24 to 26

Alkoxysilyl Compounds Having Two Allyl Groups (Carbamate, B-4 to D-4) (Method 6)

Alkoxysilyl compounds of Formulae B-4 to D-4, having two allyl groups were synthesized by performing the first step to the third step according to the same method as Synthetic Example 23 except for the amounts used of the reactants. The amounts used in each synthetic step are shown in Table 6 below.

TABLE 6

| Synthetic example | Starting material | Diisopropylethylamine | Methylene chloride | Triethoxysilyl propyl isocyanate | Final product |
| --- | --- | --- | --- | --- | --- |
| 24 | 3,3'-diallylbiphenyl-4,4'-diol | 11.6 g | 300 ml | 18.6 g | B-4 |
| 25 | 1,8-diallylnaphthalene-2,7-diol | 12.9 g | 300 ml | 20.6 g | C-4 |
| 26 | 4,4'-(9H-fluorene-9,9-diyl)bis(2-allylphenol) | 7.2 g | 300 ml | 11.5 g | D-4 |

The synthetic reaction carried out in Synthetic Example 24 is as follows.
The synthetic reaction carried out in Synthetic Example 25 is as follows.
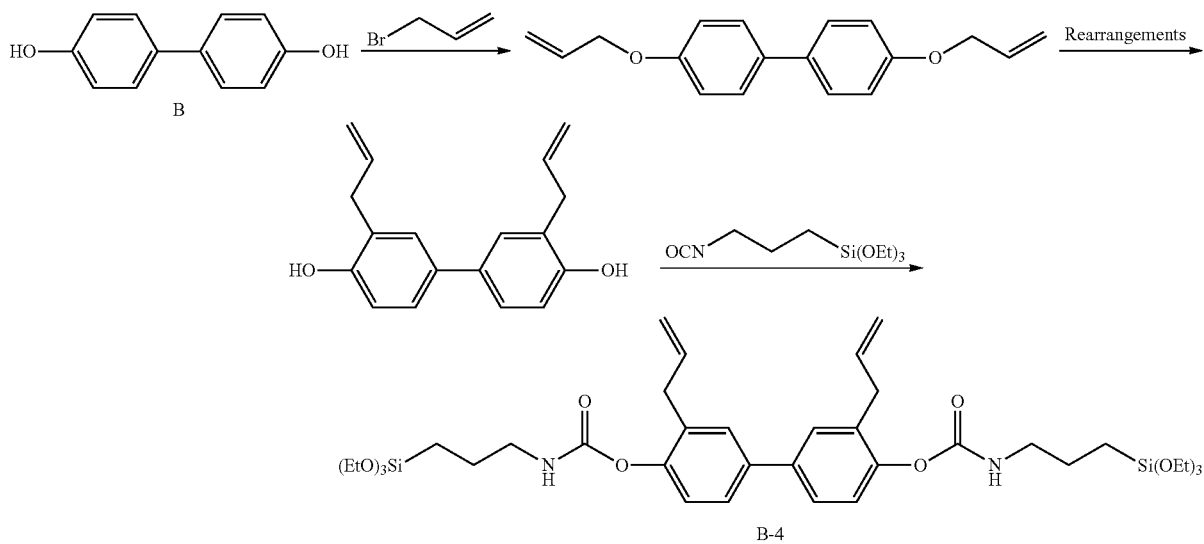
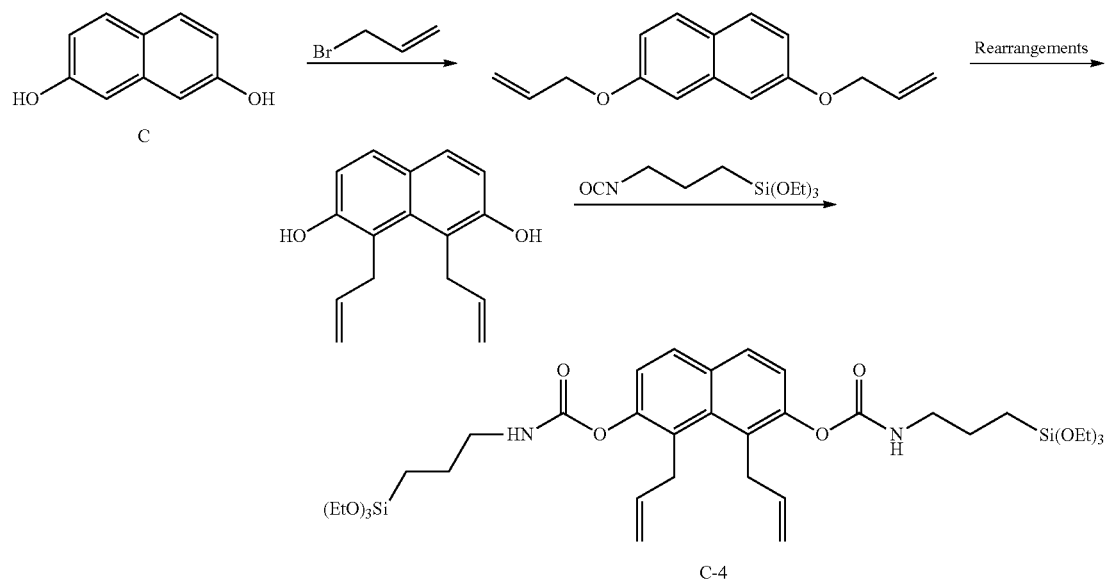
The synthetic reaction carried out in Synthetic Example 26 is as follows.
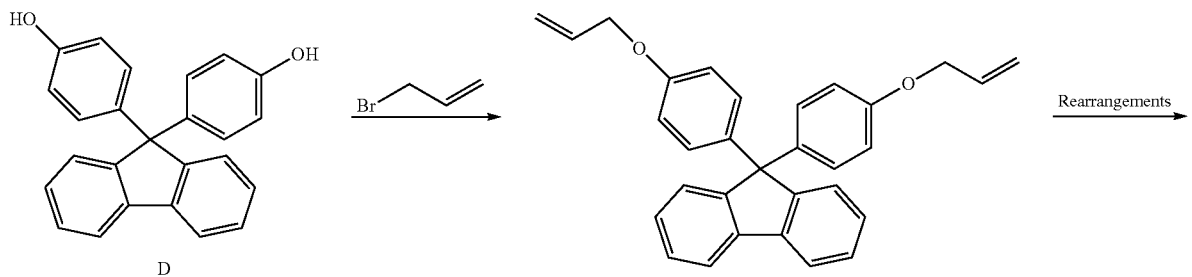

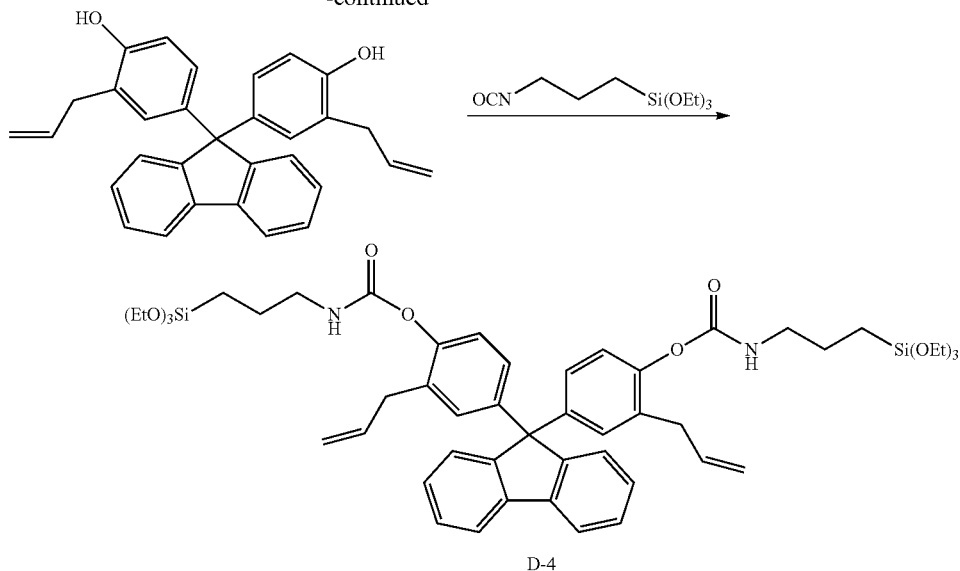

D-4

Synthetic Example 27

Bisphenol A-Based Alkoxysilyl Compound Having Two Kinds of Alkoxysilyl Groups (A-5) (Method 7)

To a flask, 10 g of 4,4'-(propane-2,2-diyl)bis(2-allyl-4,1-phenylene)bis(3-(triethoxysilyl)propylcarbamate, which was the compound A-4 synthesized in Synthetic Example 23, 0.06 g of $PtO_2$, 4.5 g of triethoxysilane, and 100 ml of toluene were added and stirred at room temperature for 5 minutes. Then, the temperature was elevated to 80° C., and heating and stirring were continued for 12 hours. Then, the reaction product was cooled to room temperature and filtered using a celite filter to remove inorganic materials. Toluene was removed by evaporation and drying, and the product thus obtained was completely dried using a vacuum pump to obtain a final product (A-5).

The synthetic reaction carried out in Synthetic Example 27 is as follows.

Synthetic Examples 28 to 30

Alkoxysilyl Compounds Having Two Kinds of Alkoxysilyl Groups (B-5 to D-5) (Method 7)

Alkoxysilyl compounds of Formulae B-5 to D-5, having two kinds of alkoxysilyl groups were synthesized by performing the same method as Synthetic Example 27 except for the amounts used of the reactants. The amounts used in each synthetic step are shown in Table 7 below.

TABLE 7

| Synthetic example | Starting material | $PtO_2$ | $HSi(OEt)_3$ | Toluene | Final product |
|---|---|---|---|---|---|
| 28 | B-4 | 0.06 g | 4.7 g | 100 ml | B-5 |
| 29 | C-4 | 0.06 g | 4.9 g | 100 ml | C-5 |
| 30 | D-4 | 0.05 g | 3.9 g | 100 ml | D-5 |

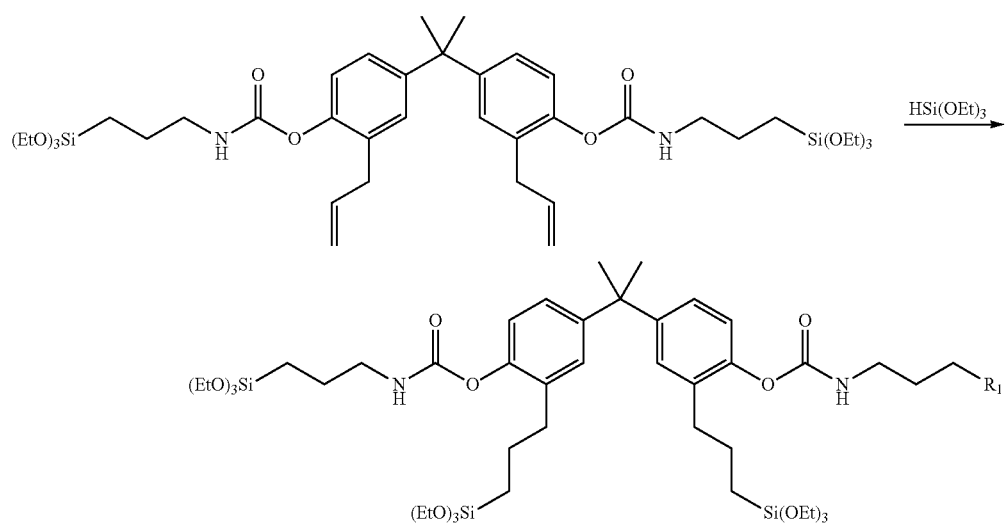

The synthetic reaction carried out in Synthetic Example 28 is as follows.
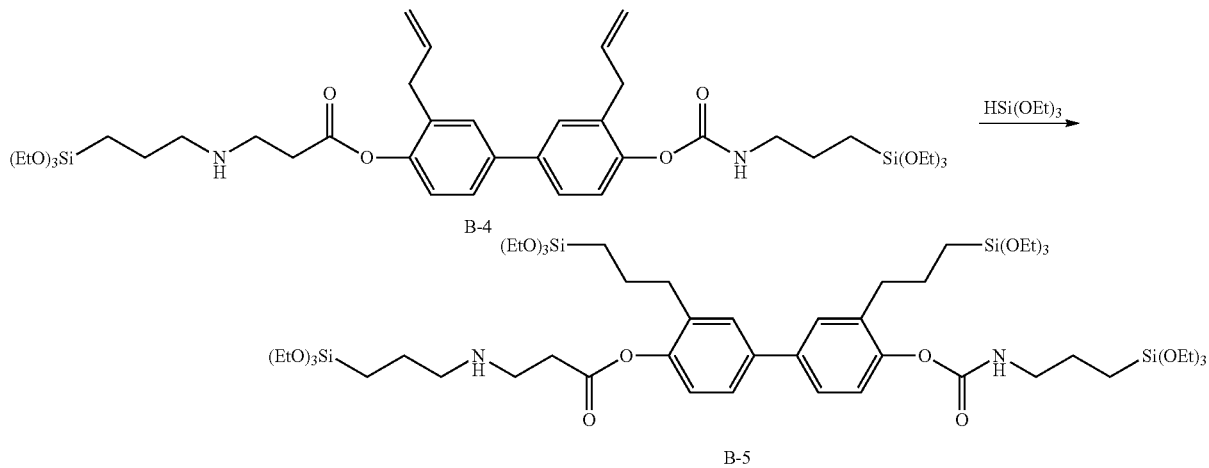
The synthetic reaction carried out in Synthetic Example 29 is as follows.
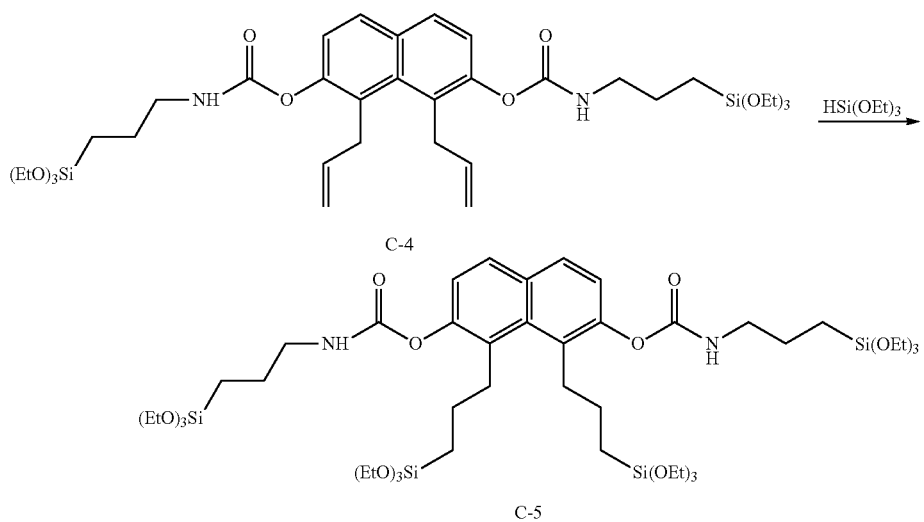
The synthetic reaction carried out in Synthetic Example 30 is as follows.
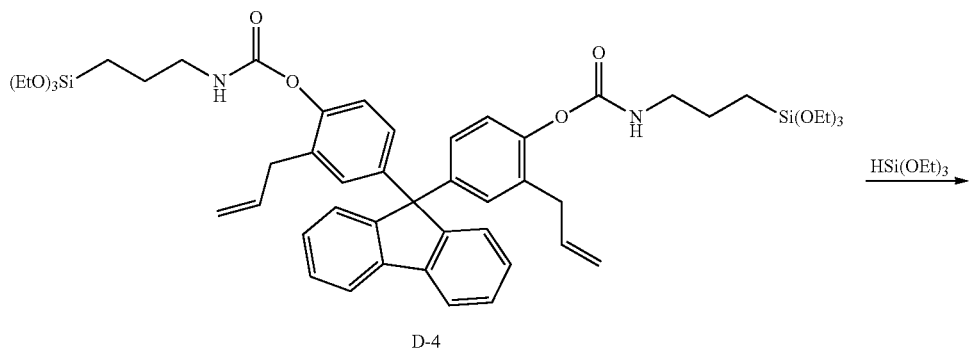

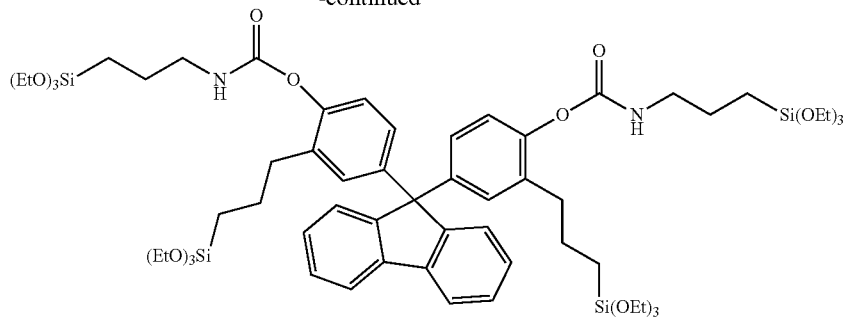

D-5

Synthetic Example 31

Alkoxysilyl Compound Having Two Kinds of Alkoxysilyl Groups (A-6) (Method 8)

(1) First Step

To a flask, 8.57 g of diisopropylethylamine (DIPEA), 16.40 g of triethoxysilyl propyl isocyanate, and 60 ml of methylene chloride were stirred at room temperature. Then, a solution of 25 g of bisphenol A (A) dissolved in 60 ml of methylene chloride was slowly added thereto at 60° C. for 6 hours. Then, the stirring was continued further for 9 hours. After finishing the reaction, the solution thus obtained was cooled to room temperature and worked-up with $H_2O$. An organic layer was separated, and remaining $H_2O$ was removed using $MgSO_4$. The product thus obtained was filtered and dried by evaporation to obtain an intermediate.

(2) Second Step

To a two-necked flask, 25 g of the intermediate of the first step, 9.69 g of allyl bromide and 50 ml of tetrahydrofuran (THF) were added and stirred at room temperature. Then, a NaOH solution prepared by dissoving 3.20 g of NaOH in 50 ml of $H_2O$ was slowly added thereto at room temperature for 1 hour, and the stirring was continued for 4 hours further. Then, THF was removed using an evaporator, and the thus obtained product was worked-up using 200 ml of ethyl acetate and $H_2O$ to remove inorganic materials. To an organic layer, $MgSO_4$ was added to remove remaining $H_2O$, and filtering using a celite filter and drying by evaporation were performed to obtain an intermediate.

(3) Third Step

To a flask, 25 g of the intermediate of the second step, 0.18 g of $PtO_2$, 11.7 g of triethoxysilane, and 150 ml of toluene were added and stirred at room temperature for 5 minutes. Then, the temperature was elevated to 80° C., and heating and stirring were continued for 12 hours. Then, the reaction product was cooled to room temperature and filtered using a celite filter to remove inorganic materials. Toluene was removed by evaporation and drying, and the product thus obtained was completely dried using a vacuum pump to obtain a final product (A-6).

The synthetic reaction carried out in Synthetic Example 31 is as follows.

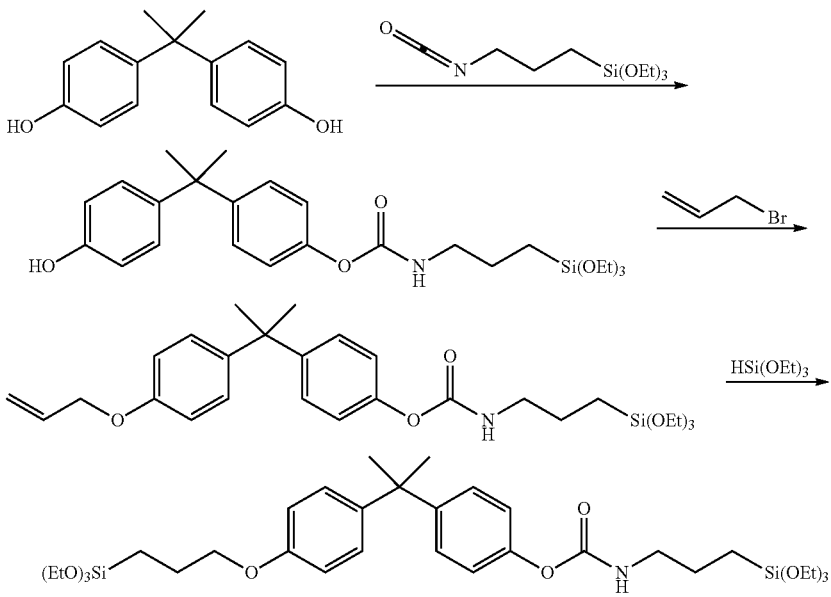

Synthetic Examples 32 to 34

Alkoxysilyl Compounds Having Two Kinds of Alkoxysilyl Groups (B-6 to D-6) (Method 8)

Alkoxysilyl compounds of Formulae B-6 to D-6, having two kinds of alkoxysilyl groups were synthesized by performing the same method as Synthetic Example 31 except for the amounts used of the reactants. The amounts used in each synthetic step are shown in the following table.

TABLE 8

| Synthetic example | Starting material | | Diisopropylethylamine | Triethoxysilyl propyl isocyanate | Methylene chloride |
|---|---|---|---|---|---|
| 32 | (1,1'-biphenyl)-4,4'-diol | 25 g | 17.37 g | 33.23 g | 269 ml |
| 33 | Naphthanlene-2,7-diol | 25 g | 20.17 g | 38.61 g | 312 ml |
| 34 | 4,4'-(9H-fluorene-9,9-diyl)diphenol | 25 g | 9.22 g | 17.65 g | 143 ml |

(2) Second Step

TABLE 9

| Synthetic example | Starting material | | Allyl bromide | NaOH | H$_2$O | THF |
|---|---|---|---|---|---|---|
| 32 | Product of the first step | 25 g | 13.95 g | 4.61 g | 72 ml | 72 ml |
| 33 | Product of the first step | 25 g | 14.84 g | 4.91 g | 153 ml | 153 ml |
| 34 | Product of the first step | 25 g | 10.12 g | 3.35 g | 105 ml | 105 ml |

(3) Third Step

TABLE 10

| Synthetic example | Starting material | | PtO$_2$ | Triethoxysilane | Toluene | Final product |
|---|---|---|---|---|---|---|
| 32 | Product of the second step | 25 g | 0.12 g | 9.34 g | 244 ml | B-6 |
| 33 | Product of the second step | 25 g | 0.13 g | 9.89 g | 256 ml | C-6 |
| 34 | Product of the second step | 25 g | 0.09 g | 6.94 g | 181 ml | D-6 |

The synthetic reaction carried out in Synthetic Example 32 is as follows.

The synthetic reaction carried out in Synthetic Example 33 is as follows.

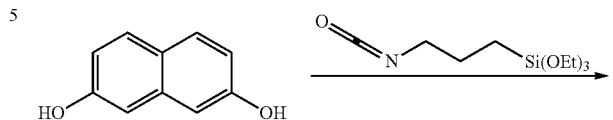

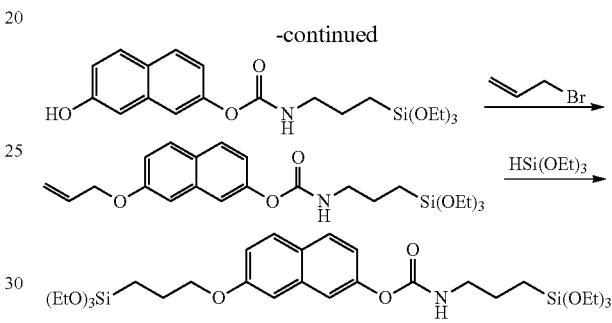

The synthetic reaction carried out in Synthetic Example 34 is as follows.

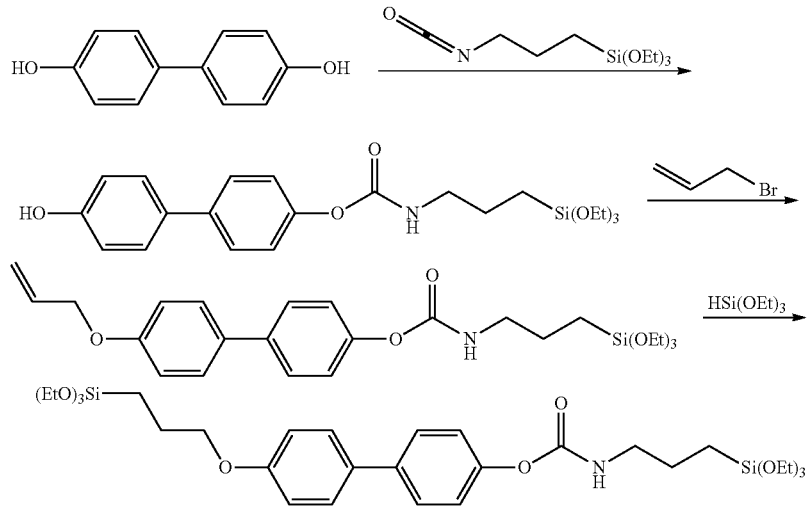

product thus obtained was worked-up using 200 ml of ethyl acetate with $H_2O$ to remove inorganic materials. $MgSO_4$ was added to an organic layer to remove remaining $H_2O$, and filtering using a celite filter and drying by evaporation were performed to obtain an intermediate.

(2) Second Step

To a flask, 25 g of the intermediate of the first step, 0.14 g of $PtO_2$, 10.59 g of triethoxysilane, and 277 ml of toluene were added and stirred at room temperature for 5 minutes. Then, the temperature was elevated to 80° C., and heating and stirring were performed for 12 hours. Then, the reaction product was cooled to room temperature and filtered using a celite filter to remove inorganic materials. Toluene was removed by evaporation, and the product thus obtained was completely dried using a vacuum pump to obtain an intermediate.

(3) Third Step

To a flask, 5.55 g of diisopropylethylamine (DIPEA), 10.63 g of triethoxysilyl propyl isocyanate, and 86 ml of methylene chloride were added and stirred at room temperature. Then, a solution of 25 g of the intermediate of the second step in 64 ml of methylene chloride was slowly added at 60° C. for 6 hours, and the stirring was further continued for 9 hours. After finishing the reaction, the solution was cooled to room temperature and worked-up using $H_2O$, and an organic layer was separated. $MgSO_4$ was added to the organic layer to remove remaining $H_2O$, and filtering and drying by evaporation were performed to obtain a final product (A-7).

The synthetic reaction carried out in Synthetic Example 35 is as follows.

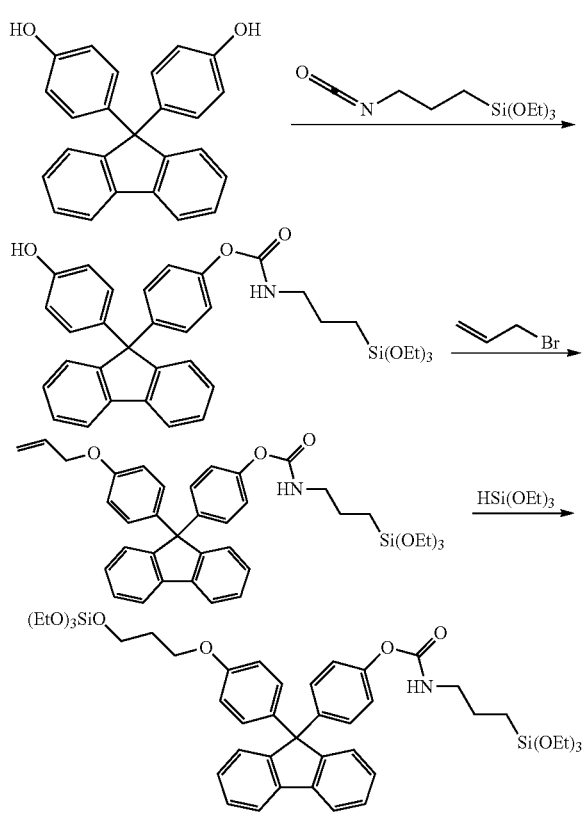

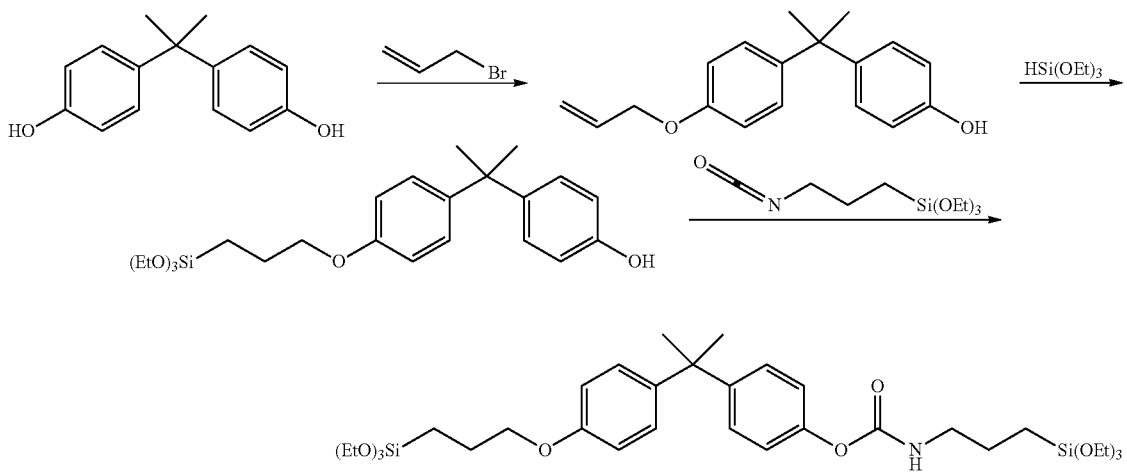

Synthetic Example 35

Alkoxysilyl Compound Having Two Kinds of Alkoxysilyl Groups (A-7) (Method 9)

(1) First Step

To a two-necked flask, 25 g of bisphenol A (A), 8.02 g of allyl bromide, and 83 ml of tetrahydrofuran (THF) were added and stirred at room temperature. Then, a NaOH solution prepared by dissoving 2.65 g of NaOH in 830 ml of $H_2O$ was slowly added thereto at room temperature for 3 hours. Then, the stirring was continued further for 4 hours. After that, THF was removed using an evaporator and the Synthetic Examples 36 to 38

Alkoxysilyl Compounds Having Two Kinds of Alkoxysilyl Groups (B-7 to D-7) (Method 9)

Alkoxysilyl compounds of Formulae B-7 to D-7, having two kinds of alkoxysilyl groups were synthesized by performing the same method as Synthetic Example 35 except for the amounts used of the reactants. The amounts used in each synthetic step are shown in the following table.

(1) First Step

TABLE 11

| Synthetic example | Starting material | Allyl bromide | NaOH | H$_2$O | THF |
|---|---|---|---|---|---|
| 36 | (1,1'-biphenyl)-4,4'-diol | 25 g | 16.25 g | 5.37 g | 168 ml | 168 ml |
| 37 | Naphthanlene-2,7-diol | 25 g | 18.88 g | 6.24 g | 195 ml | 195 ml |
| 38 | 4,4'-(9H-fluorene-9,9-diyl)diphenol | 25 g | 8.63 g | 2.85 g | 89 ml | 89 ml |

(2) Second Step

TABLE 12

| Synthetic example | Starting material | | PtO$_2$ | Triethoxysilane | Toluene |
|---|---|---|---|---|---|
| 36 | Product of the first step | 25 g | 0.25 g | 19.55 g | 511 ml |
| 37 | Product of the first step | 25 g | 0.28 g | 21.99 g | 575 ml |
| 38 | Product of the first step | 25 g | 0.14 g | 11.30 g | 295 ml |

(3) Third Step

TABLE 13

| Synthetic example | Starting material | | Diisopropylethylamine | Triethoxysilyl propyl isocyanate | Methylene chloride | Final product |
|---|---|---|---|---|---|---|
| 36 | Product of the second step | 25 g | 8.27 g | 15.83 g | 128 ml | B-7 |
| 37 | Product of the second step | 25 g | 8.85 g | 16.94 g | 137 ml | C-7 |
| 38 | Product of the second step | 25 g | 5.82 g | 11.14 g | 90 ml | D-7 |

The synthetic reaction carried out in Synthetic Example 36 is as follows.

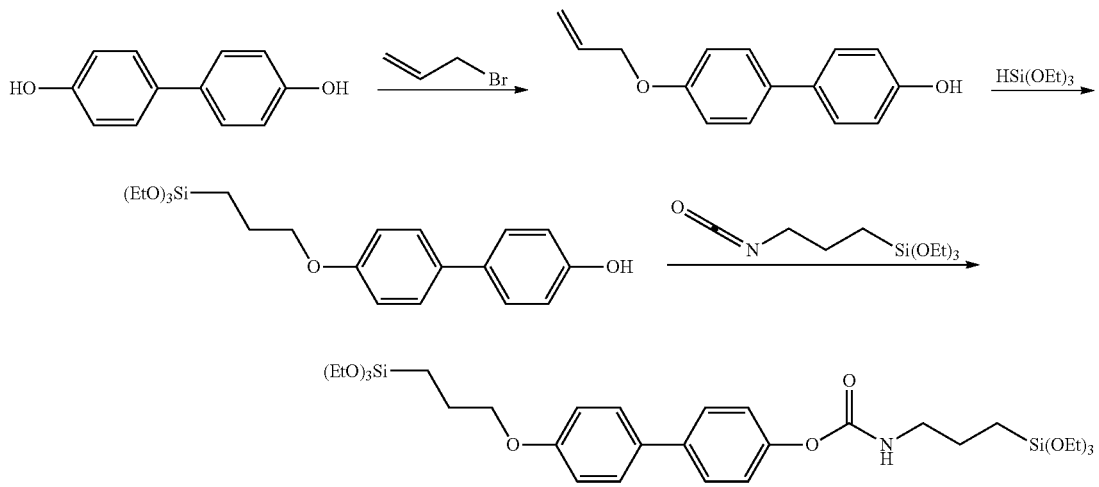

The synthetic reaction carried out in Synthetic Example 37 is as follows.

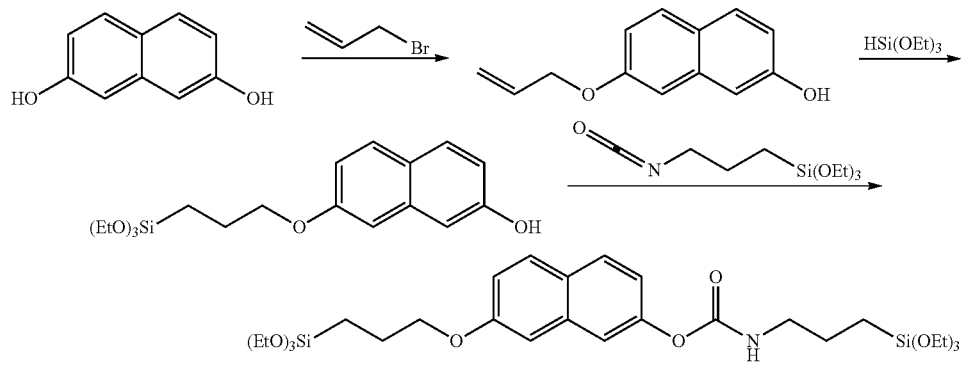

The synthetic reaction carried out in Synthetic Example 38 is as follows.

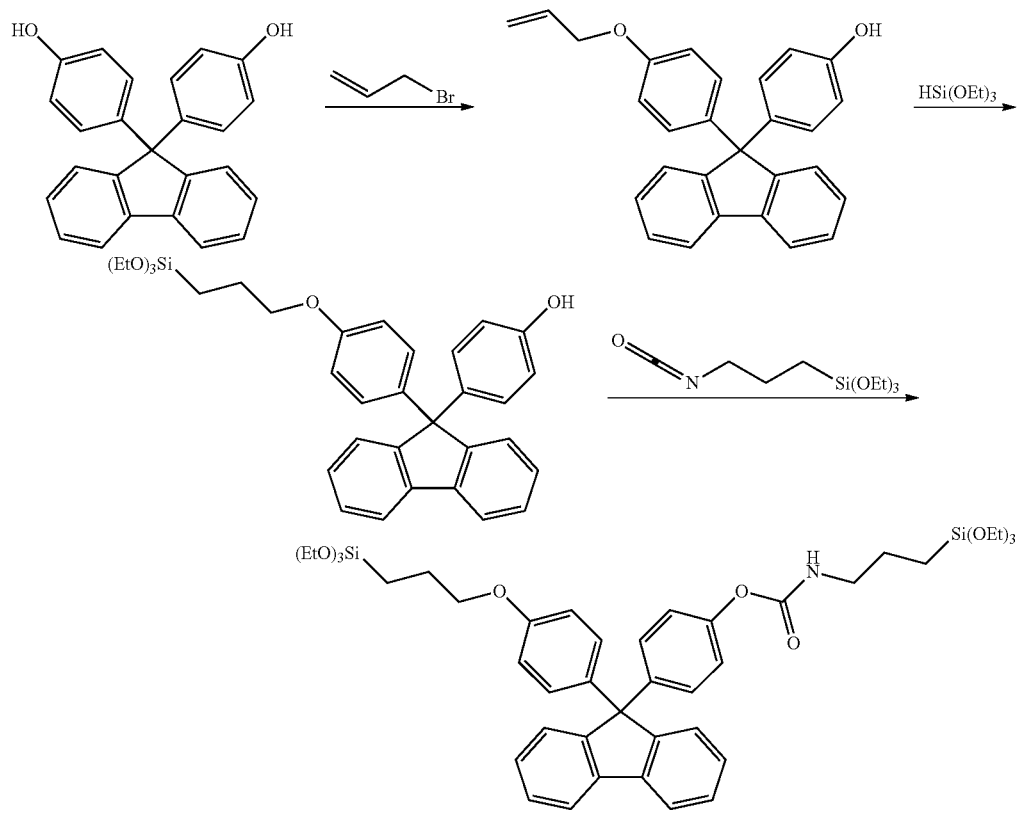

Synthetic Example 39

Alkoxysilyl Compound Having Four Alkoxysilyl Groups (A-8) (Method 10)

(1) First Step

To a two-necked flask, 25 g of bisphenol A (A), 16.25 g of allyl bromide, and 83 ml of tetrahydrofuran (THF) were added and stirred at room temperature. Then, a NaOH solution prepared by dissoving 5.37 g of NaOH in 83 ml of $H_2O$ was slowly added thereto at room temperature for 3 hours. Then, the stirring was continued further for 4 hours. After that, THF was removed using an evaporator and the product thus obtained was worked-up using 200 ml of ethyl acetate with $H_2O$ to remove inorganic materials. $MgSO_4$ was added to an organic layer to remove remaining $H_2O$, and filtering using a celite filter and drying by evaporation were performed to obtain an intermediate.

(2) Second Step

To a flask, 25 g of the intermediate of the first step, i.e., 4,4'-(propane-2,2-diyl)bis(allyloxy)benzene was added and reacted at 180° C. for 8 hours to obtain rearranged (Claisen rearrangement) 4,4'-(propane-2,2-diyl)bis(2-allylphenol.

(3) Third Step

To a two-necked flask, 25 g of the intermediate of the second step, i.e., 4,4'-(propane-2,2-diyl)bis(2-allylphenol, 13.18 g of allyl bromide, and 68 ml of tetrahydrofuran (THF) were added and stirred at room temperature. Then, a NaOH solution prepared by dissoving 4.36 g of NaOH in 68 ml of $H_2O$ was slowly added thereto at room temperature for 3 hours. Then, the stirring was continued further for 4 hours. After that, THF was removed using an evaporator and the product thus obtained was worked-up using 200 ml of ethyl acetate with $H_2O$ to remove inorganic materials. $MgSO_4$ was added to an organic layer to remove remaining $H_2O$, and filtering using a celite filter and drying by evaporation were performed to obtain an intermediate.

(4) Fourth Step

To a flask, 25 g of the intermediate of the third step, i.e., 4,4'-(propane-2,2-diyl)bis(2-allyl-1-(allyloxy)benzene, was added and reacted at 180° C. for 8 hours to obtain rearranged (Claisen rearrangement) 4,4'-(propane-2,2-diyl)bis(2,6-diallylphenol.

(5) Fifth Step

To a flask, 25 g of the intermediate of the fourth step, 0.10 g of $PtO_2$, 30.35 g of triethoxysilane, and 214 ml of toluene were added and stirred at room temperature for 5 minutes. Then, the temperature was elevated to 80° C. After that, the reaction product was cooled to room temperature and filtered using a celite filter to remove inorganic materials. Toluene was removed by evaporation and drying, and the product thus obtained was completely dried using a vacuum pump to obtain a final product (A-8).

The synthetic reaction carried out in Synthetic Example 39 is as follows.

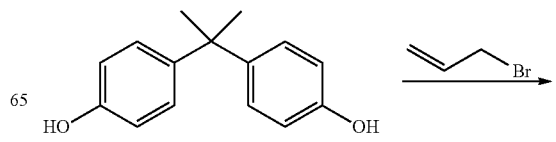

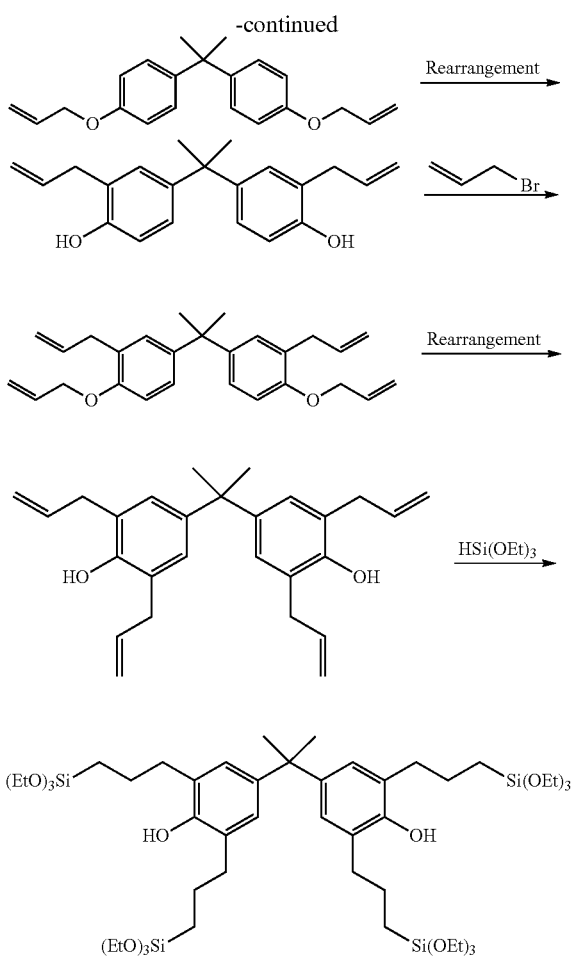

Synthetic Examples 40 to 42

Compounds Having Four Alkoxysilyl Groups (B-8 to D-8) (Method 10)

Alkoxysilyl compounds of Formulae B-8 to D-8, having four alkoxysilyl groups were synthesized by performing the same method as Synthetic Example 39 except for the amounts used of the reactants. The amounts used in each synthetic step are shown in the following table.

(1) First Step

TABLE 14

| Synthetic example | Starting material | Allyl bromide | NaOH | H$_2$O | THF |
|---|---|---|---|---|---|
| 40 | (1,1'-biphenyl)-4,4'-diol | 25 g | 32.51 g | 10.75 g | 168 ml | 168 ml |
| 41 | Naphthanlene-2,7-diol | 25 g | 37.77 g | 12.49 g | 195 ml | 195 ml |
| 42 | 4,4'-(9H-fluorene-9,9-diyl)diphenol | 25 g | 17.26 g | 5.71 g | 89 ml | 89 ml |

(2) Second Step

In the second step for synthesizing Compounds B-8 to D-8, the reaction was performed using only the product of the first step.

(3) Third Step

TABLE 15

| Synthetic example | Starting material | Allyl bromide | NaOH | H$_2$O | THF |
|---|---|---|---|---|---|
| 40 | Product of the second step | 25 g | 22.57 g | 7.46 g | 117 ml | 117 ml |
| 41 | Product of the second step | 25 g | 24.98 g | 8.26 g | 129 ml | 129 ml |
| 42 | Product of the second step | 25 g | 13.99 g | 4.63 g | 72 ml | 72 ml |

(4) Fourth Step

In the second step for synthesizing Compounds B-8 to D-8, the reaction was performed using only the product of the third step.

(5) Fifth Step

TABLE 16

| Synthetic example | Starting material | | PtO$_2$ | Triethoxysilane | Toluene | Final product |
|---|---|---|---|---|---|---|
| 40 | Product of the fourth step | 25 g | 0.16 g | 46.93 g | 331 ml | B-8 |
| 41 | Product of the fourth step | 25 g | 0.15 g | 44.99 g | 317 ml | C-8 |
| 42 | Product of the fourth step | 25 g | 0.11 g | 31.93 g | 225 ml | D-8 |

The synthetic reaction carried out in Synthetic Example 40 is as follows.

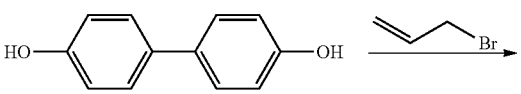

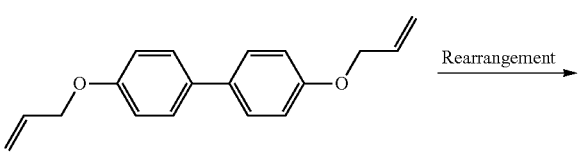

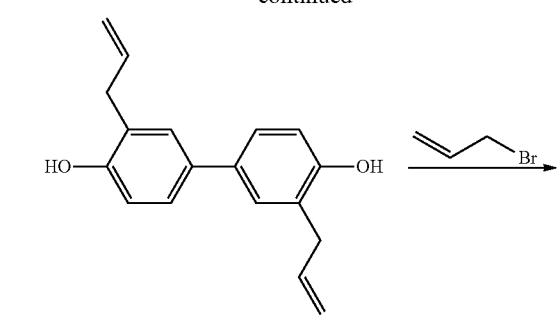
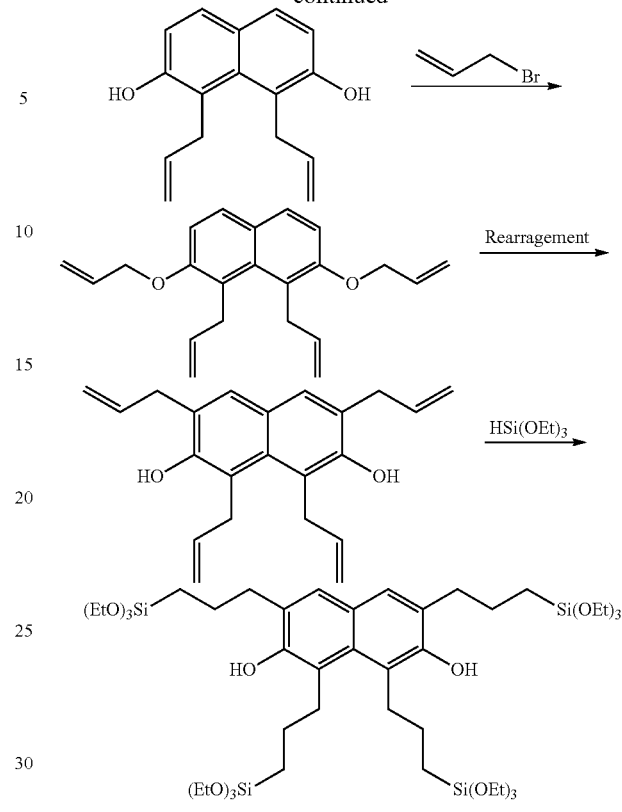
The synthetic reaction carried out in Synthetic Example 42 is as follows.
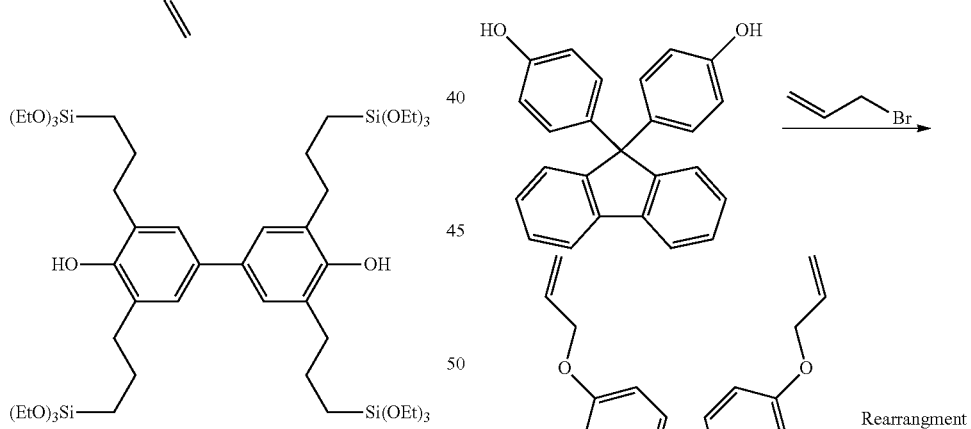
The synthetic reaction carried out in Synthetic Example 41 is as follows.
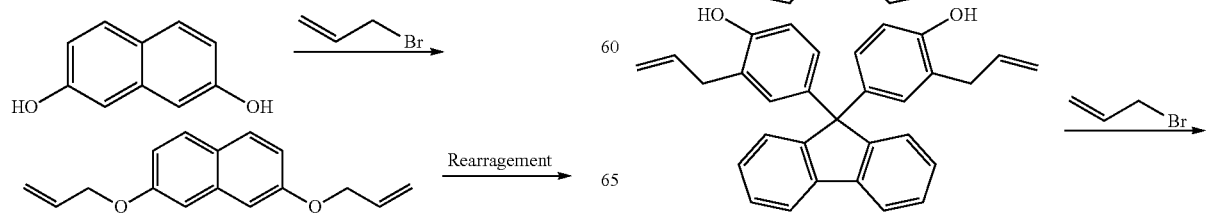

-continued

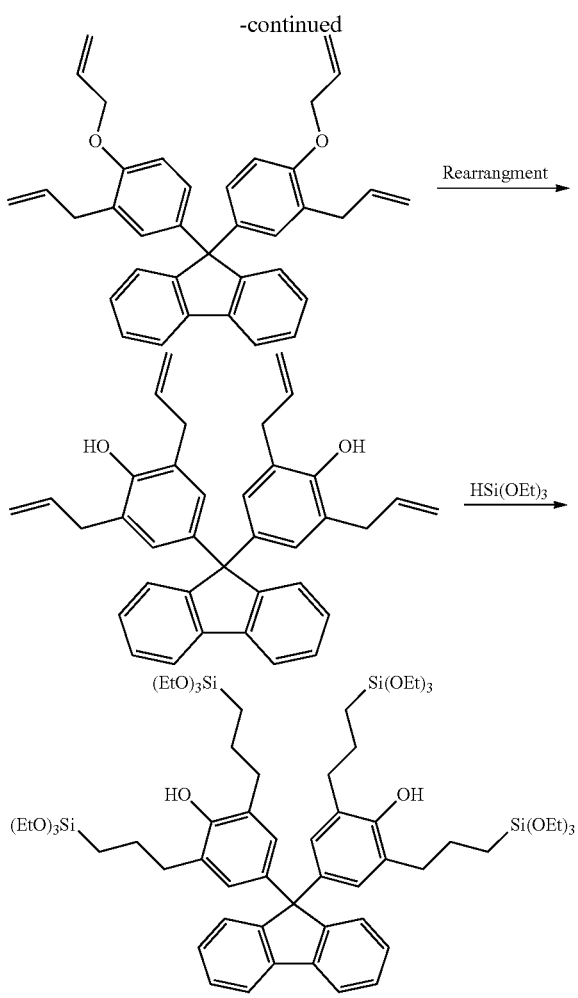

Synthetic Example 43

Compound Having Six Alkoxysilyl Groups (A-9) (Method 11)

(1) First Step

To a two-necked flask, 25 g of the intermediate after the reaction of the fourth step in Synthetic Example 39, 11.18 g of allyl bromide, and 58 ml of tetrahydrofuran (THF) were added and stirred at room temperature. Then, a NaOH solution prepared by dissoving 3.70 g of NaOH in 58 ml of $H_2O$ was slowly added thereto at room temperature for 3 hours. Then, the stirring was continued further for 4 hours. After that, THF was removed using an evaporator and the product thus obtained was worked-up using 200 ml of ethyl acetate with $H_2O$ to remove inorganic materials. $MgSO_4$ was added to an organic layer to remove remaining $H_2O$, and filtering using a celite filter and drying by evaporation were performed to obtain an intermediate.

(2) Second Step

To a flask, 25 g of the intermediate of the first step, 0.09 g of $PtO_2$, 39.54 g of triethoxysilane, and 186 ml of toluene were added and stirred at room temperature for 5 minutes. Then, the reaction temperature was elevated to 80° C. and heating and stirring were performed for 12 hours. Then, the product was cooled to room temperature and filtered using a celite filter to remove inorganic materials. Toluene was removed by evaporation and drying, and the product thus obtained was completely dried using a vacuum pump to obtain a final product (A-9).

The synthetic reaction carried out in Synthetic Example 43 is as follows.

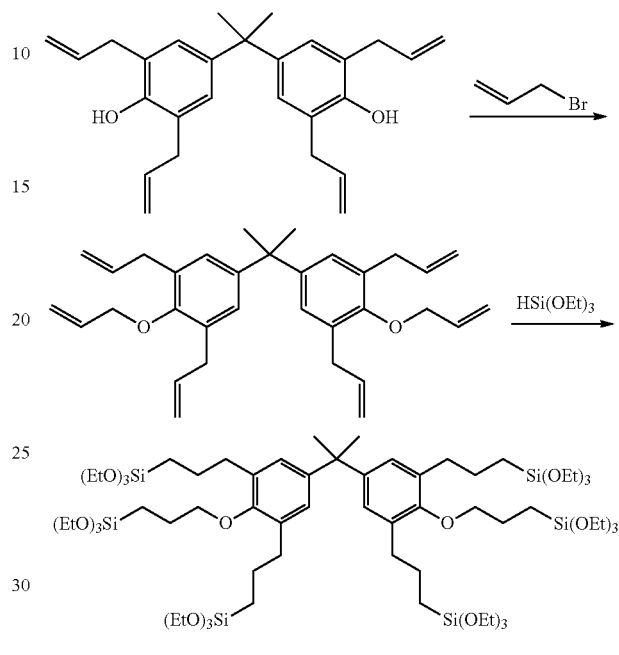

Synthetic Examples 44 to 46

Compounds Having Six Alkoxysilyl Groups (B-9 to D-9) (Method 11)

Alkoxysilyl compounds of Formulae B-9 to D-9, having six alkoxysilyl groups were synthesized by performing the same method as Synthetic Example 43 except for the amounts used of the reactants. The amounts used in each synthetic step are shown in the following table.

(1) First Step

TABLE 17

| Synthetic example | Starting material | Allyl bromide | NaOH | $H_2O$ | THF |
|---|---|---|---|---|---|
| 44 | Product of the fourth step in Synthetic example 40 | 25 g | 17.28 g | 5.71 g | 89 ml | 89 ml |
| 45 | Product of the fourth step in Synthetic example 40 | 25 g | 16.56 g | 5.48 g | 86 ml | 86 ml |
| 46 | Product of the fourth step in Synthetic example 40 | 25 g | 11.76 g | 3.89 g | 61 ml | 61 ml |

(2) Second Step

TABLE 18

| Synthetic example | Starting material | | PtO$_2$ | Triethoxysilane | Toluene | Final product |
|---|---|---|---|---|---|---|
| 44 | Product of the first step | 25 g | 0.13 g | 57.03 g | 268 ml | B-9 |
| 45 | Product of the first step | 25 g | 0.13 g | 55.11 g | 259 ml | C-9 |
| 46 | Product of the first step | 25 g | 0.09 g | 41.32 g | 194 ml | D-9 |

The synthetic reaction carried out in Synthetic Example 44 is as follows.

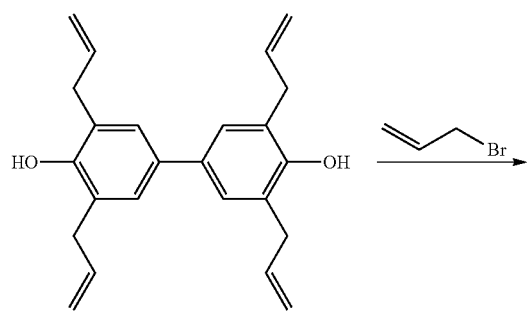

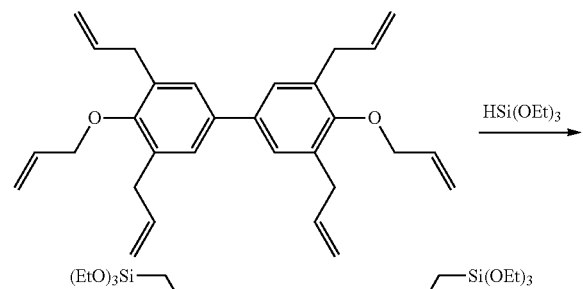

The synthetic reaction carried out in Synthetic Example 45 is as follows.

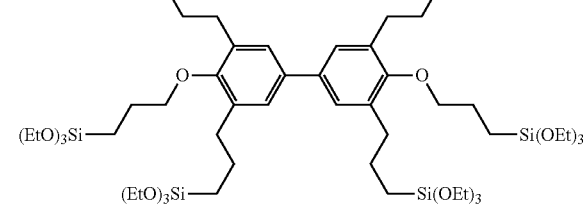

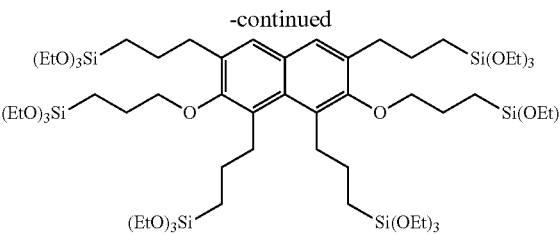

-continued

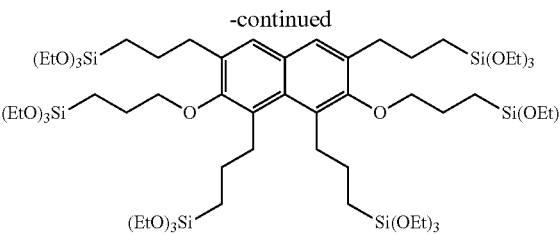

The synthetic reaction carried out in Synthetic Example 46 is as follows.

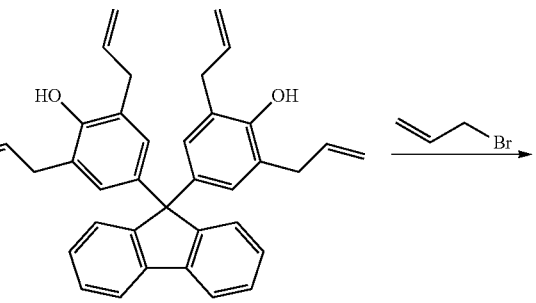

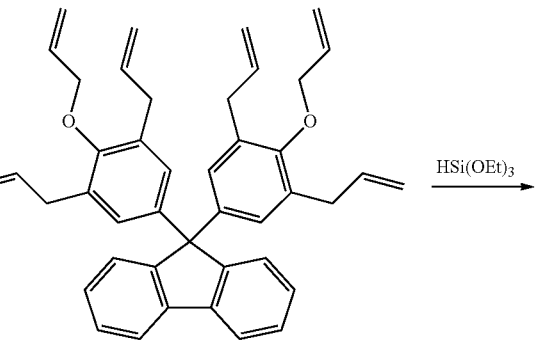

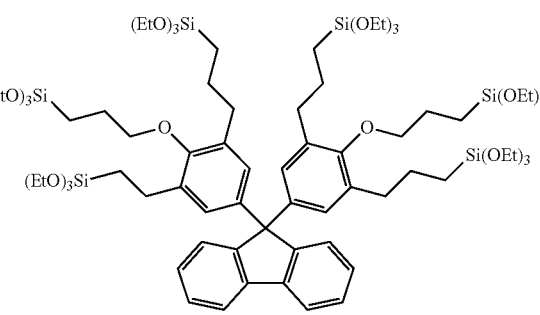

Synthetic Example 47

Compound Having Four Allyl Groups and Two Alkoxysilyl Groups (Carbamate, A-10) (Method 12)

To a flask, 11.94 g of diisopropylethylamine (DIPEA), 22.85 g of triethoxysilyl propyl isocyanate, and 46 ml of methylene chloride were added and stirred at room temperature. Then, a solution of 25 g of the intermediate after the fourth step of Synthetic Example 39 dissolved in 46 ml of methylene chloride was slowly added thereto at 60° C. for 6 hours. Then, the stirring was continued further for 9 hours. After finishing the reaction, the product thus obtained was cooled to room temperature and was worked-up using $H_2O$. An organic layer was separated and $MgSO_4$ was added to remove remaining $H_2O$, and filtering and drying by evaporation were performed to obtain an intermediate.

The synthetic reaction carried out in Synthetic Example 47 is as follows.

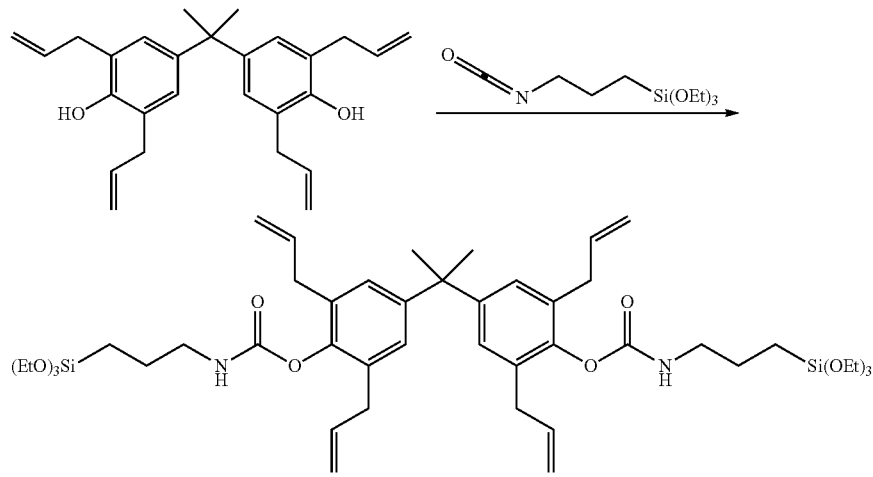

Synthetic Example 48 to 50

Compounds Having Four Allyl Groups and Two Alkoxysilyl Groups (Carbamate, B-10 to D-10) (Method 12)

Alkoxysilyl compounds of Formulae B-10 to D-10, having four allyl groups and two alkoxysilyl groups were synthesized by performing the same method as Synthetic Example 47 except for the amounts used of the reactants. The amounts used in each synthetic step are shown in the following table.

TABLE 19

| Synthetic example | Starting material | | Diisopropylethylamine | Triethoxysilyl propyl isocyanate | Methylene chloride | Final product |
|---|---|---|---|---|---|---|
| 48 | Product of the fourth step in Synthetic example 40 | 25 g | 18.46 g | 35.33 g | 143 ml | B-10 |
| 49 | Product of the fourth step in Synthetic example 40 | 25 g | 17.70 g | 33.87 g | 137 ml | C-10 |
| 50 | Product of the fourth step in Synthetic example 40 | 25 g | 12.56 g | 24.04 g | 98 ml | D-10 |

The synthetic reaction carried out in Synthetic Example 48 is as follows.

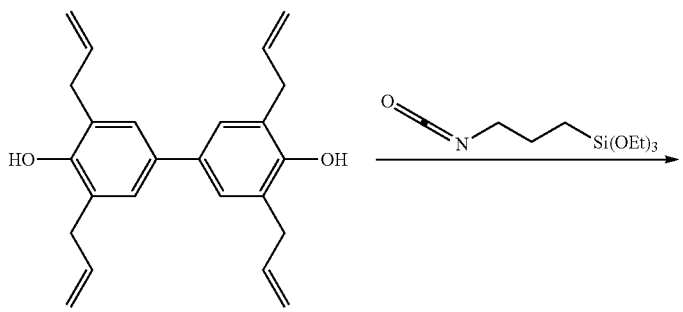

-continued
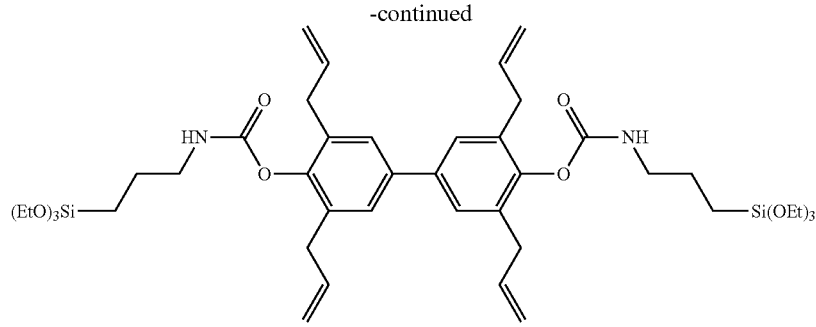
The synthetic reaction carried out in Synthetic Example 49 is as follows.
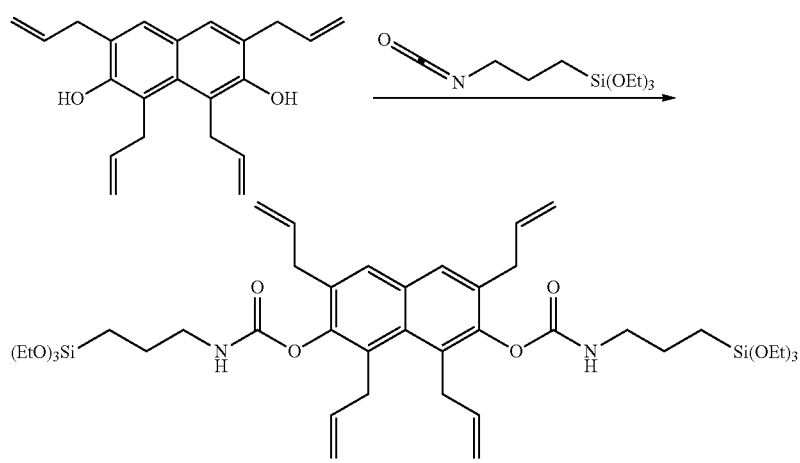
The synthetic reaction carried out in Synthetic Example 50 is as follows.
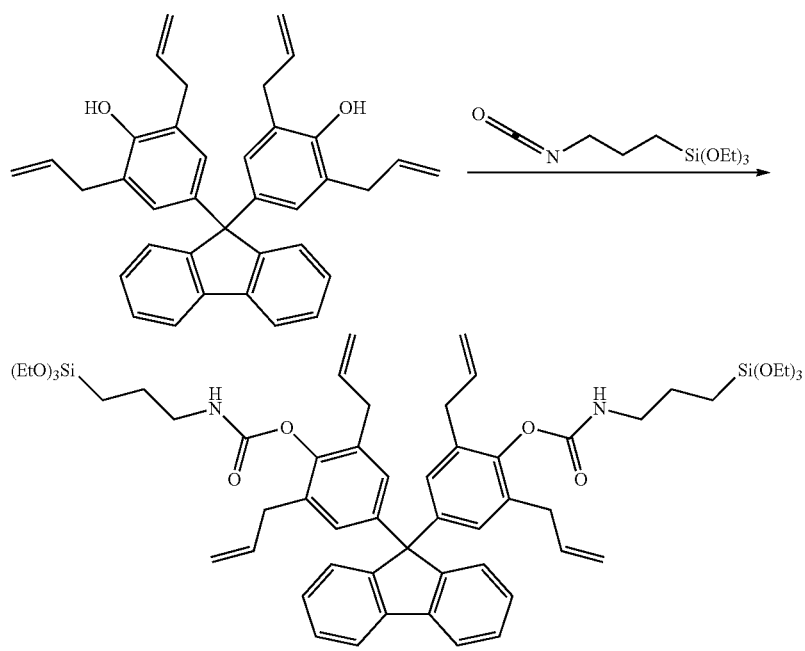

Synthetic Example 51

Compound Having Two Kinds of Alkoxysilyl Groups (A-11) (Method 13)

(1) First Step

To a flask, 25 g of the intermediate after the reaction of the fourth step of Synthetic Example 39, 0.10 g of $PtO_2$, 30.36 g of triethoxysilane, and 214 ml of toluene were added and stirred at room temperature for 5 minutes. Then, the reaction temperature was elevated to 80° C. and heating and stirring were performed for 12 hours. Then, the product thus obtained was cooled to room temperature and filtered using a celite filter to remove inorganic materials. Toluene was removed by evaporation and drying, and the product thus obtained was completely dried using a vacuum pump to obtain an intermediate.

(2) Second Step

To a flask, 5.39 g of diisopropylethylamine (DIPEA), 10.32 g of triethoxysilyl propyl isocyanate, and 20 ml of methylene chloride were added and stirred at room temperature. Then, a solution of 25 g of the intermediate of the first step dissolved in 20 ml of methylene chloride was slowly added thereto at 60° C. for 6 hours. Then, the stirring was continued further for 9 hours. After finishing the reaction, the product thus obtained was cooled to room temperature and worked-up using $H_2O$. An organic layer was separated and $MgSO_4$ was added to remove remaining $H_2O$, and filtering and drying by evaporation were performed to obtain an intermediate.

The synthetic reaction carried out in Synthetic Example 51 is as follows.

Synthetic Examples 52 to 54

Compounds Having Two Kinds of Alkoxysilyl Groups (B-11 to D-11) (Method 13)

Alkoxysilyl compounds of Formulae B-11 to D-11, having two kinds of alkoxysilyl groups were synthesized by performing the same method as Synthetic Example 51 except for the amounts used of the reactants. The amounts used in each synthetic step are shown in the following table.

(1) First Step

TABLE 20

| Synthetic example | Starting material | PtO$_2$ | Triethoxysilane | Toluene |
|---|---|---|---|---|
| 52 | Product of the fourth step in Synthetic example 40 | 25 g | 0.16 g | 46.93 g | 331 ml |
| 53 | Product of the fourth step in Synthetic example 40 | 25 g | 0.15 g | 44.99 g | 317 ml |
| 54 | Product of the fourth step in Synthetic example 40 | 25 g | 0.11 g | 31.93 g | 224 ml |

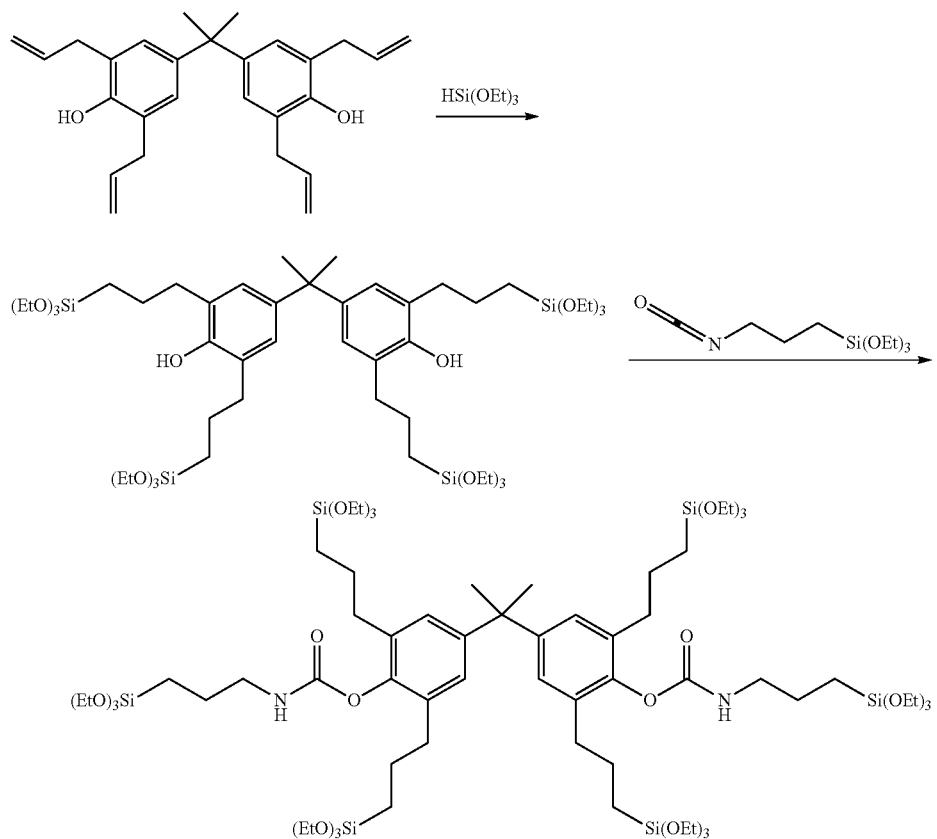

(2) Second Step

TABLE 21

| Synthetic example | Starting material | | Diisopropylethylamine | Trimethoxysilyl propyl isocyanate | Methylene chloride | Final product |
|---|---|---|---|---|---|---|
| 52 | Product of the first step | 25 g | 6.42 g | 12.28 g | 50 ml | B-11 |
| 53 | Product of the first step | 25 g | 6.32 g | 12.10 g | 49 ml | C-11 |
| 54 | Product of the first step | 25 g | 5.52 g | 10.56 g | 43 ml | D-11 |

The synthetic reaction carried out in Synthetic Example 52 is as follows.

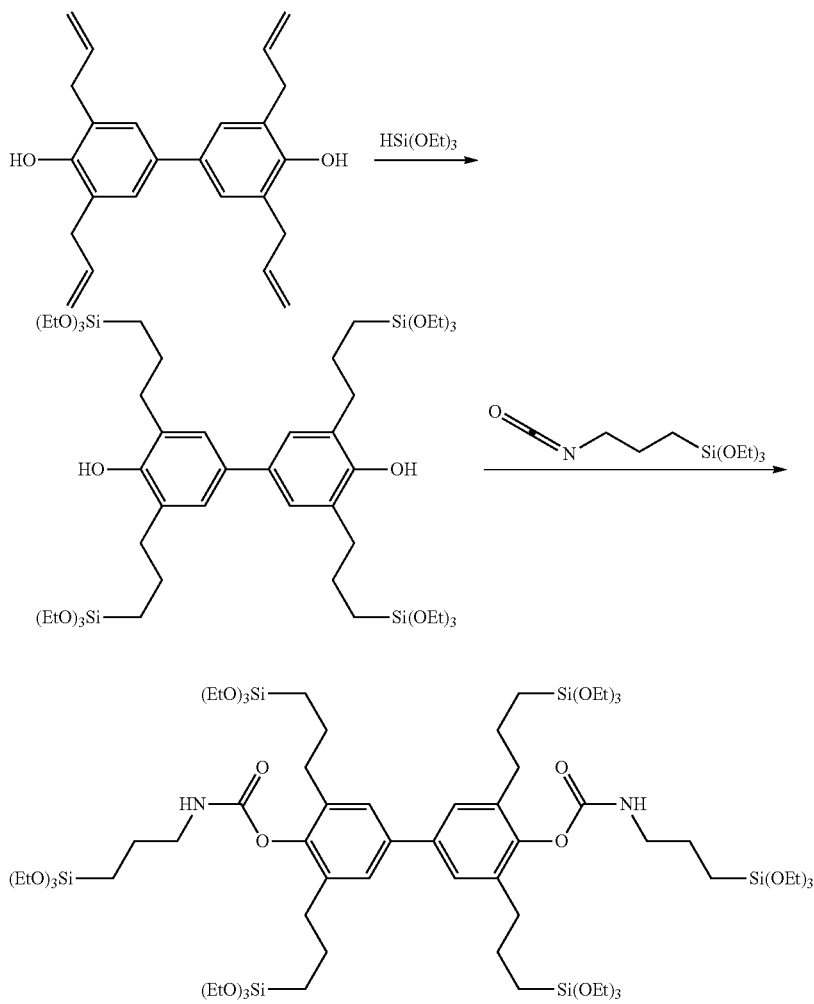

The synthetic reaction carried out in Synthetic Example 53 is as follows.

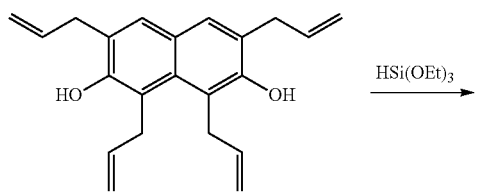

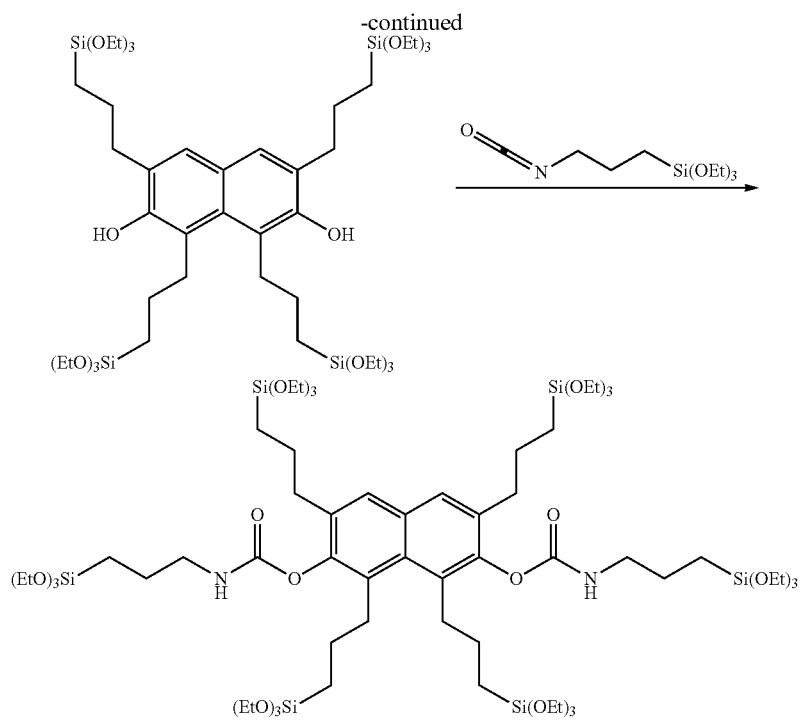
The synthetic reaction carried out in Synthetic Example 54 is as follows.
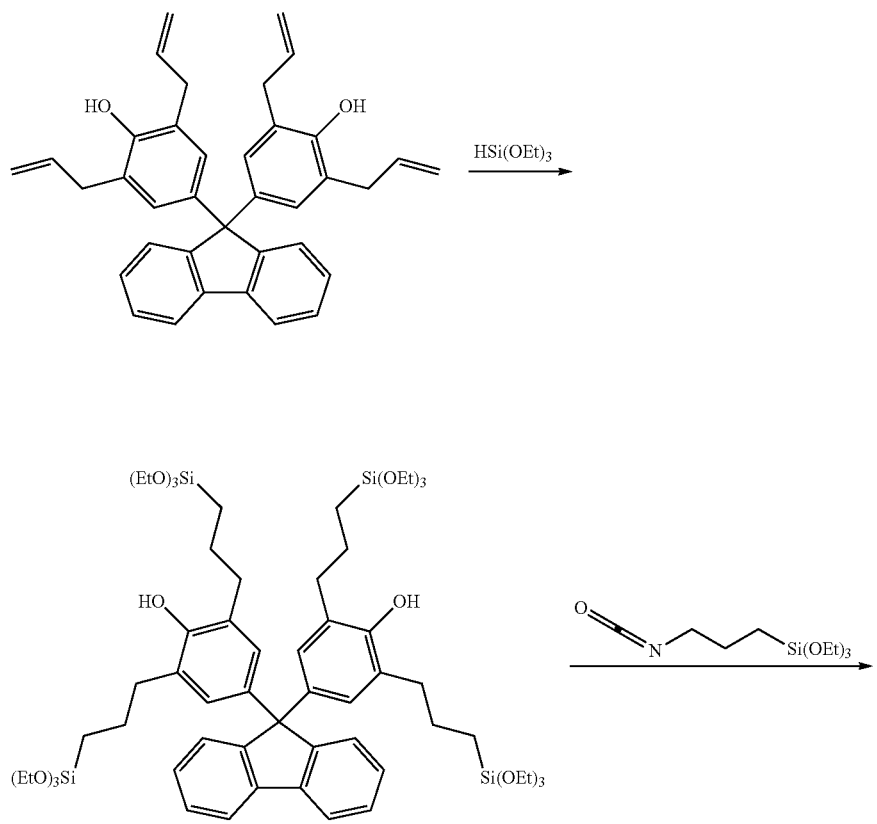

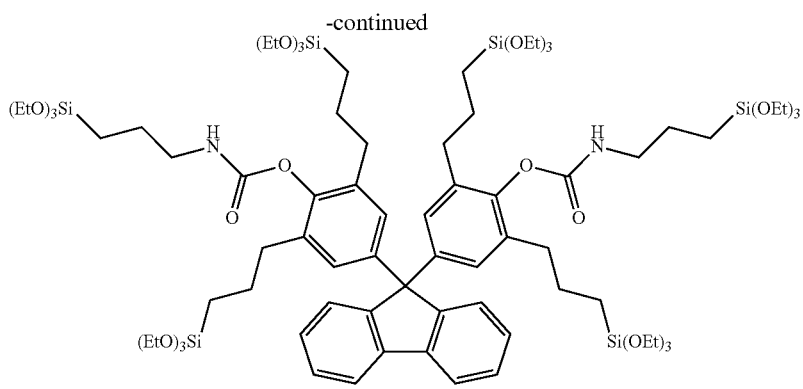

Synthetic Example 55

Synthesis of Silyl Compound Having a Bisphenol A-Based Core

To a 500 ml flask, 22.61 g of a starting material, 29.75 ml of triethoxysilane, 337 mg of platinum oxide, and 60 ml of tetrahydrofuran were added and mixed, followed by stirring at 60° C. for 3 hours in an argon charged state. After the reaction, the crude product thus obtained was filtered using a celite filter, and solvents were removed using an evaporator to obtain a bisphenol A compound including an alkoxysilyl group as a final product. The reaction scheme and the NMR data of the final product thus obtained are as follows.

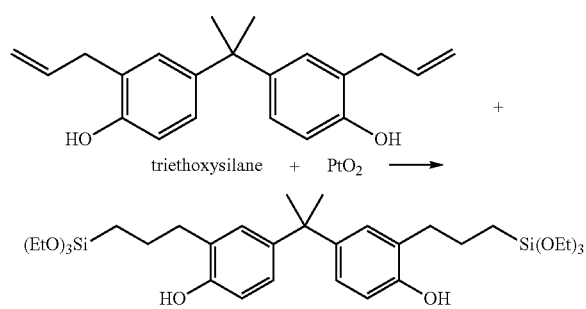

$^1$H NMR (400 MHz, DMSO): δ=0.53 (t, J=8.0 Hz, 4H), 1.11 (t, J=4.0 Hz, 18H), 1.51-1.57 (m, 10H), 2.44-2.48 (m, 4H), 3.70 (dd, J=8.0 Hz, 12H), 6.62-6.68 (m, 2H), 6.78-6.85 (m, 4H), 8.94 (br, 2H).

Synthetic Example 56

Synthesis of Silyl Compound Having a Biphenyl-Based Core

To a 500 ml flask, 22.67 g of a starting material, 34.54 ml of triethoxysilane, 389 mg of platinum oxide, and 60 ml of tetrahydrofuran were added and mixed, followed by stirring at 60° C. for 3 hours in an argon charged state. After the reaction, the crude product thus obtained was filtered using a celite filter, and solvents were removed using an evaporator to obtain a biphenyl compound including an alkoxysilyl group as a final product. The reaction scheme and the NMR data of the final product thus obtained are as follows.

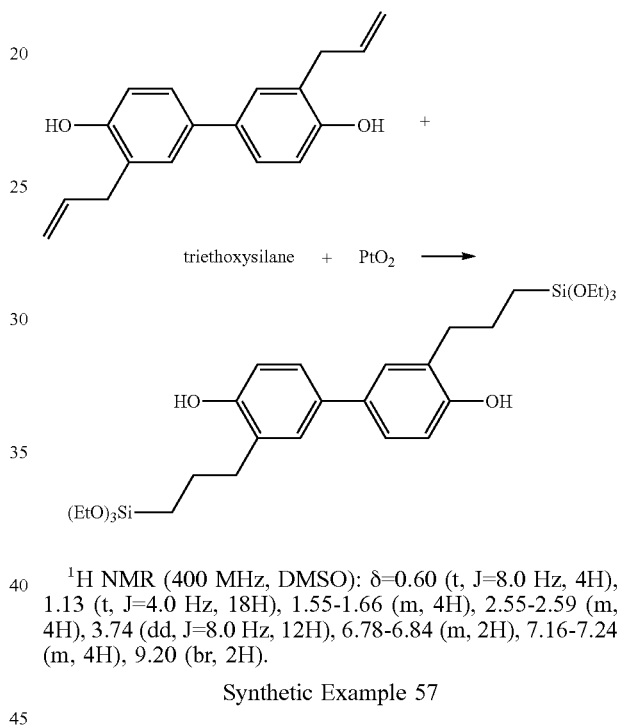

$^1$H NMR (400 MHz, DMSO): δ=0.60 (t, J=8.0 Hz, 4H), 1.13 (t, J=4.0 Hz, 18H), 1.55-1.66 (m, 4H), 2.55-2.59 (m, 4H), 3.74 (dd, J=8.0 Hz, 12H), 6.78-6.84 (m, 2H), 7.16-7.24 (m, 4H), 9.20 (br, 2H).

Synthetic Example 57

Synthesis of Silyl Compound Having a Naphthalene-Based Core

To a 500 ml flask, 15.78 g of a starting material, 26.65 ml of triethoxysilane, 301 mg of platinum oxide, and 60 ml of tetrahydrofuran were added and mixed, followed by stirring at 60° C. for 3 hours in an argon charged state. After the reaction, the crude product thus obtained was filtered using a celite filter, and solvents were removed using an evaporator to obtain a biphenyl compound including an alkoxysilyl group as a final product. The reaction scheme and the NMR data of the final product thus obtained are as follows.

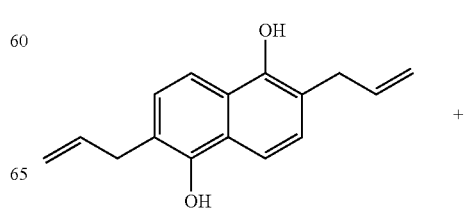

-continued

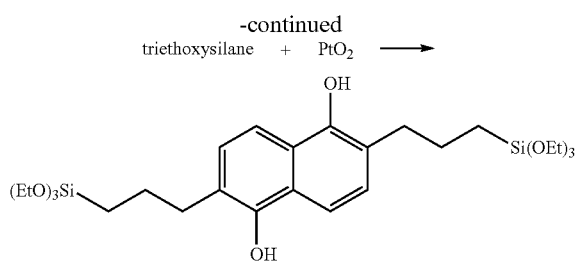

¹H NMR (400 MHz, DMSO): δ=0.53 (t, J=8.0 Hz, 4H), 1.11 (t, J=4.0 Hz, 18H), 1.51-1.57 (m, 4H), 2.44-2.48 (m, 4H), 3.70 (dd, J=8.0 Hz, 12H), 7.08-7.11 (m, 2H), 7.59-7.64 (m, 2H), 8.79 (br, 2H).

Synthetic Example 58

Synthesis of Silyl Compound Having a Triphenylmethane-Based Core

To a flask, 25 g of 4,4',4"-trihydroxytriphenylmethane (E), and 500 ml of tetrahydrofuran (THF) were added and stirred at room temperature. Then, 42.3 g of triethoxysilyl propyl isocyanate was added at room temperature for 30 minutes, and reacted at room temperature for 20 hours. After finishing the reaction, solvents were removed using an evaporator, and the product thus obtained was completely dried using a vacuum oven to obtain a final product. The reaction scheme and the NMR data of the final product thus obtained are as follows.

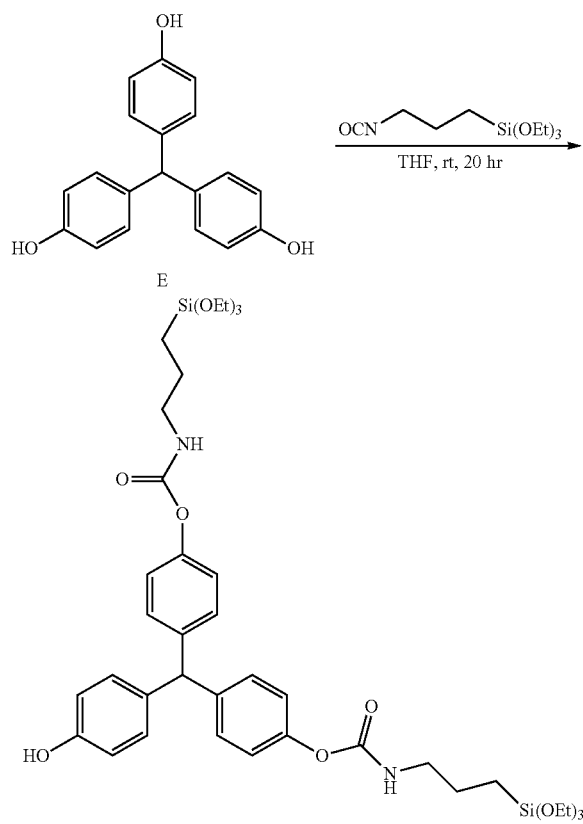

¹H NMR (400 MHz, DMSO): δ=9.48 (br.s, 1H), 7.89-7.86 (m, 2H), 7.05-6.97 (m, 4H), 6.84-6.80 (m, 4H), 6.75-6.69 (m, 4H), 5.65 (s, 0.25H), 5.51 (s, 0.47H), 5.34 (s, 0.17H), 5.18 (s, 0.11H), 3.83 (q, 12H, J=6.8 Hz), 3.26 (q, 4H, J=6.8 Hz), 1.74-1.66 (m, 4H), 1.24 (t, 18H, J=7.2 Hz), 0.70-0.66 (m, 4H).

Synthetic Example 59

Synthesis of Silyl Compound Having a Tetraphenylethane-Based Core

To a flask, 25 g of 4,4',4",4'''-tetrahydroxytetraphenylethane (F), and 500 ml of tetrahydrofuran (THF) were added and stirred at room temperature. Then, 31.0 g of triethoxysilyl propyl isocyanate was added at room temperature for 30 minutes, and reacted at room temperature for 20 hours. After finishing the reaction, solvents were removed using an evaporator, and the product thus obtained was completely dried using a vacuum oven to obtain a final product. The reaction scheme and the NMR data of the final product thus obtained are as follows.

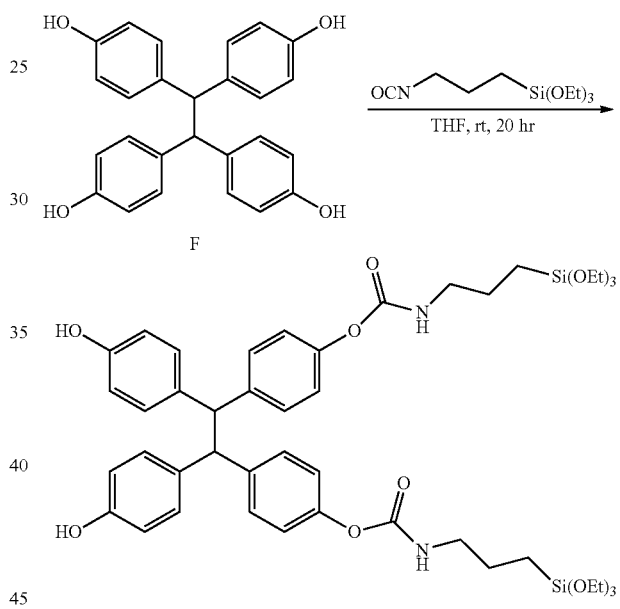

¹H NMR (400 MHz, DMSO): δ=9.50 (s, 2H), 7.90-7.87 (m, 2H), 7.31-7.11 (m, 12H), 6.75-6.66 (m, 4H), 4.57-4.55 (m, 2H), 3.83 (q, 12H, J=6.8 Hz), 3.36-3.32 (m, 4H), 1.74-1.66 (m, 4H), 1.24 (t, 18H, J=7.2 Hz), 0.70-0.66 (m, 4H).

Synthetic Example 60

Synthesis of Silyl Compound Having a Bisnaphthalene-Based Core

To a flask, 25 g of 1,1'-methylenedinaphthalen-2,7-diol (G), and 500 ml of tetrahydrofuran (THF) were added and stirred at room temperature. Then, 37.2 g of triethoxysilyl propyl isocyanate was added at room temperature for 30 minutes, and reacted at room temperature for 20 hours. After finishing the reaction, solvents were removed using an evaporator, and the product thus obtained was completely dried using a vacuum oven to obtain a final product. The reaction scheme and the NMR data of the final product thus obtained are as follows.

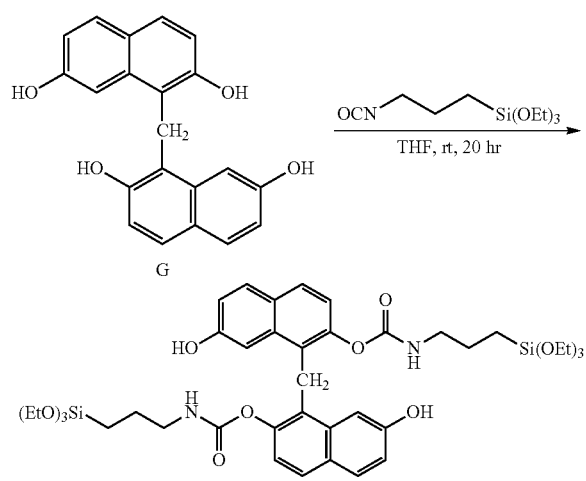

$^1$H NMR (400 MHz, DMSO): δ=9.51 (s, 2H), 7.91-7.87 (m, 2H), 7.48-7.41-7.33 (m, 6H), 6.96-6.84 (m, 4H), 4.50 (s, 2H), 3.84 (q, 12H, J=6.8 Hz), 3.36-3.30 (m, 4H), 1.75-1.67 (m, 4H), 1.23 (t, 18H, J=7.2 Hz), 0.71-0.66 (m, 4H).

Evaluation of Physical Properties

1. Preparation of Glass Fiber Composite

The composition of the following Table 22 was dissolved in methyl ethyl ketone with the solid content of 40 wt % to 50 wt %, and mixed to attain a homogeneous solution. To the mixture thus obtained, a glass fiber (T-glass 2116 of Nittobo Co.) was immersed to prepare a glass fiber composite. Then, the composite was put in a vacuum oven heated to 100° C. to remove solvents and cured in a hot press to obtain each glass fiber composite film (4 mm×16 mm×0.1 mm) according to Examples 1 to 37 and Comparative Example 1. During composite film preparation, the resin content of the composite film was controlled by the applied pressure of a press and the viscosity of a resin, and the resins content in the composite films are shown in Table 22 below. In this case, polyvinyl acetal of Table 22 was mixed together when dissolving the composition in methyl ethyl ketone, and was used as an additive to prevent the crack of a cured product.

2. Preparation of Epoxy Filler Composite (Cured Product)

The composition in the following Table 23 were dissolved in methyl ethyl ketone with the solid content of 40 wt % to prepare a mixture solution. In this case, a silica slurry dispersed in a 2-methoxyethanol solvent was used. The mixture was blended in a rate of 1,500 rpm for 1 hour, and a curing agent was added, followed by further mixing for 50 minutes. Finally, a curing catalyst was added and further mixed for 10 minutes to obtain an epoxy mixture. Then, the mixture was inserted into a vacuum oven preheated to 100° C. to remove solvents, and was cured in a preheated hot press to prepare an epoxy filler (inorganic particles) composite (5 mm×5 mm×3 mm) according to any one of Examples 38 to 50.

3. Evaluation of Heat Resistance Properties

The dimensional changes of the composites obtained in the examples and the comparative examples were evaluated with the variation of the temperature by using a Thermomechanical analyzer and are illustrated in the following Table 22 and Table 23. The specimen of the glass fiber composite film of an alkoxysilyl compound was prepared with a dimension of 4×16×0.1 (mm$^3$), and the specimen of the epoxy filler composite was prepared with a dimension of 5×5×3 (mm$^3$). In the following Table 22 and Table 23, Tg-less means that glass transition temperature disappears. The dimensional changes of Example 34 and Comparative Example 1 with the temperature are illustrated in FIG. 1, and the dimensional changes of Example 1 and Comparative Example 1 with the temperature are illustrated in FIG. 2.

TABLE 22

Glass fiber composite

| | Compound (synthetic example no.) | Example 1 | Example 2 | Example 3 | Example 4 | Example 5 | Example 6 | Example 7 | Example 8 |
|---|---|---|---|---|---|---|---|---|---|
| composition (g) | Silyl compound and epoxy | Synthetic Example 1 | 5.00 | 5.00 | 5.00 | 5.00 | | | | |
| | | Synthetic Example 2 | | | | | 5.00 | 5.00 | 5.00 | |
| | | Synthetic Example 3 | | | | | | | | 5.00 |
| | | Synthetic Example 10 | | | | | | | | |
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |
| | | Synthetic Example 16 | | | | | | | | |
| | | Synthetic Example 19 | | | | | | | | |
| | | Synthetic Example 55 | | | | | | | | |
| | | Synthetic Example 56 | | | | | | | | |
| | | Synthetic Example 57 | | | | | | | | |
| | | DGEBA[1] | | 2.96 | 5.91 | | | 6.34 | | |
| | | EXA4700[2] | | | | 8.48 | | | 9.08 | |
| | | YX4000H[3] | | | | | | | | |
| | | polydis[4] | | | | | | | | |
| | | HF-1M[5] | | | | 8.74 | | | | |
| | | TPP[6] | | | | | | | | |
| | | 2E4MZ[7] | 0.10 | 0.16 | 0.22 | 0.27 | 0.10 | 0.23 | 0.28 | 0.10 |
| | | Polyvinyl acetal | 0.56 | 0.88 | 1.21 | 1.50 | 0.56 | 1.26 | 1.56 | 0.56 |
| | | Silica | 10.51 | 16.71 | 22.92 | 44.55 | 10.51 | 23.83 | 29.57 | 10.51 |
| | | Resin content (wt %) | 50% | 53% | 50% | 53% | 50% | 50% | 51% | 51% |
| Heat resistance | | CTE (ppm/° C.)  \|\|α$_1$ (T < Tg) | 4.9 | 4.4 | 4.9 | 4.9 | 4.7 | 5.0 | 5.1 | 4.0 |
| | | Tg (° C.) | 150 | 110 | 110 | 220 | Tg-less | 120 | Tg-less | Tg-less |

TABLE 22-continued

Glass fiber composite

| | | Compound (synthetic example no.) | Example 9 | Example 10 | Example 11 | Example 12 | Example 13 | Example 14 | Example 15 | Example 16 |
|---|---|---|---|---|---|---|---|---|---|---|
| composition (g) | Silyl compound and epoxy | Synthetic Example 1 | | | | | | | | |
| | | Synthetic Example 2 | | | | | | | | |
| | | Synthetic Example 3 | 5.00 | 5.00 | | | | | | |
| | | Synthetic Example 10 | | | 5.00 | 5.00 | 5.00 | | | |
| | | Synthetic Example 11 | | | | | | 5.00 | 5.00 | 5.00 |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |
| | | Synthetic Example 16 | | | | | | | | |
| | | Synthetic Example 17 | | | | | | | | |
| | | Synthetic Example 18 | | | | | | | | |
| | | Synthetic Example 19 | | | | | | | | |
| | | Synthetic Example 55 | | | | | | | | |
| | | Synthetic Example 56 | | | | | | | | |
| | | Synthetic Example 57 | | | | | | | | |
| | | DGEBA[1] | 6.63 | | | 5.21 | | | 5.54 | |
| | | EXA4700[2] | | 9.49 | | | 7.47 | | | 7.93 |
| | | YX4000H[3] | | | | | | | | |
| | | polydis[4] | | | | | | | | |
| | | HF-1M[5] | | | | | | | | |
| | | TPP[6] | | | | | | | | |
| | | 2E4MZ[7] | 0.23 | 0.29 | 0.10 | 0.20 | 0.25 | 0.10 | 0.21 | 0.26 |
| | | Polyvinyl acetal | 1.29 | 1.61 | 0.56 | 1.13 | 1.39 | 0.56 | 1.17 | 1.44 |
| | | Silica | 24.42 | 30.44 | 10.51 | 21.43 | 16.20 | 10.51 | 22.14 | 27.17 |
| | | Resin content (wt %) | 47% | 48% | 50% | 51% | 48% | 52 | 50% | 50% |
| Heat resistance | CTE (ppm/° C.) | $\alpha_1$ (T < Tg) | 4.4 | 4.6 | 4.8 | 4.9 | 5.2 | 4.4 | 4.5 | 4.8 |
| | | Tg (° C.) | 130 | Tg-less | Tg-less | 150 | 120 | Tg-less | 125 | Tg-less |

| | | Compound (synthetic example no.) | Example 17 | Example 18 | Example 19 | Example 20 | Example 21 | Example 22 | Example 23 | Example 24 |
|---|---|---|---|---|---|---|---|---|---|---|
| composition (g) | Silyl compound and epoxy | Synthetic Example 1 | | | | | | | | |
| | | Synthetic Example 2 | | | | | | | | |
| | | Synthetic Example 3 | | | | | | | | |
| | | Synthetic Example 10 | | | | | | | | |
| | | Synthetic Example 11 | | | | | | | | |
| | | Synthetic Example 12 | 5.00 | 5.00 | 5.00 | | | | | |
| | | Synthetic Example 13 | | | | 5.00 | | | | |
| | | Synthetic Example 14 | | | | | 5.00 | | | |
| | | Synthetic Example 15 | | | | | | 5.00 | | |
| | | Synthetic Example 16 | | | | | | | 5.00 | |
| | | Synthetic Example 17 | | | | | | | | 5.00 |
| | | Synthetic Example 18 | | | | | | | | |
| | | Synthetic Example 19 | | | | | | | | |
| | | Synthetic Example 55 | | | | | | | | |
| | | Synthetic Example 56 | | | | | | | | |
| | | Synthetic Example 57 | | | | | | | | |
| | | DGEBA[1] | | 5.76 | | | | | | |
| | | EXA4700[2] | | | 8.25 | 4.46 | 5.47 | 5.43 | 5.70 | 6.35 |
| | | YX4000H[3] | | | | | | | | |
| | | polydis[4] | | | | | | | | |
| | | HF-1M[5] | | | | | | | | |
| | | TPP[6] | | | | | | | | |
| | | 2E4MZ[7] | 0.10 | 0.22 | 0.27 | 0.19 | 0.21 | 0.21 | 0.21 | 0.23 |
| | | Polyvinyl acetal | 0.56 | 1.20 | 1.47 | 1.05 | 1.16 | 1.16 | 1.19 | 1.26 |
| | | Silica | 10.51 | 22.61 | 27.84 | 19.87 | 21.99 | 21.91 | 22.47 | 23.85 |
| | | Resin content (wt %) | 48% | 50% | 51% | 50% | 49% | 49% | 50% | 51% |
| Heat resistance | CTE (ppm/° C.) | $\alpha_1$ (T < Tg) | 4.2 | 4.3 | 4.6 | 5.0 | 4.8 | 5.2 | 5.1 | 5.3 |
| | | Tg (° C.) | Tg-less | 130 | Tg-less | Tg-less | Tg-less | Tg-less | Tg-less | Tg-less |

| | | Compound (synthetic example no.) | Example 25 | Example 26 | Example 27 | Example 28 | Example 29 | Example 30 | Example 31 | Example 32 |
|---|---|---|---|---|---|---|---|---|---|---|
| composition (g) | Silyl compound and epoxy | Synthetic Example 1 | | | | | | | | |
| | | Synthetic Example 2 | | | | | | | | |
| | | Synthetic Example 3 | | | | | | | | |
| | | Synthetic Example 10 | | | | | | | | |
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |
| | | Synthetic Example 16 | | | | | | | | |

TABLE 22-continued

Glass fiber composite

| | | | | | | | | | |
|---|---|---|---|---|---|---|---|---|---|
| | Synthetic Example 17 | | | | | | | | |
| | Synthetic Example 18 | 5.00 | | | | | | | |
| | Synthetic Example 19 | | 5.00 | 5.00 | | | | | |
| | Synthetic Example 55 | | | | 5.00 | 5.00 | 5.00 | | |
| | Synthetic Example 56 | | | | | | | 5.00 | 5.00 |
| | Synthetic Example 57 | | | | | | | | |
| | DGEBA[1] | | | | | 5.91 | | | 6.34 |
| | EXA4700[2] | 6.64 | | 10.33 | | | 8.48 | | |
| | YX4000H[3] | | | | | | | | |
| | polydis[4] | | | | | | | | |
| | HF-1M[5] | | | | | | | | |
| | TPP[6] | | | | | | | | |
| | 2E4MZ[7] | 0.23 | 0.10 | 0.31 | 0.10 | 0.22 | 0.27 | 0.10 | 0.23 |
| | Polyvinyl acetal | 1.29 | 0.56 | 1.70 | 0.56 | 1.21 | 1.50 | 0.56 | 1.26 |
| | Silica | 24.44 | 10.51 | 32.21 | 10.51 | 22.92 | 28.32 | 10.51 | 23.83 |
| | Resin content (wt %) | 50% | 48% | 50% | 52% | 50% | 50% | 51% | 47% |
| Heat resistance | CTE (ppm/° C.)　α₁ (T < Tg) | 5.3 | 4.4 | 5.0 | 2.8 | 3.0 | 3.3 | 2.0 | 2.7 |
| | Tg (° C.) | Tg-less | Tg-less | Tg-less | Tg-less | Tg-less | Tg-less | Tg-less | 160 |

| | | Compound (synthetic example no.) | Example 33 | Example 34 | Example 35 | Example 36 | Example 37 | Comparative Example 1 |
|---|---|---|---|---|---|---|---|---|
| composition (g) | Silyl compound and epoxy | Synthetic Example 1 | | | | | | |
| | | Synthetic Example 2 | | | | | | |
| | | Synthetic Example 3 | | | | | | |
| | | Synthetic Example 10 | | | | | | |
| | | Synthetic Example 11 | | | | | | |
| | | Synthetic Example 12 | | | | | | |
| | | Synthetic Example 13 | | | | | | |
| | | Synthetic Example 14 | | | | | | |
| | | Synthetic Example 15 | | | | | | |
| | | Synthetic Example 16 | | | | | | |
| | | Synthetic Example 17 | | | | | | |
| | | Synthetic Example 18 | | | | | | |
| | | Synthetic Example 19 | | | | | | |
| | | Synthetic Example 55 | | | | | | |
| | | Synthetic Example 56 | 5.00 | 5.00 | | | | |
| | | Synthetic Example 57 | | | 5.00 | 5.00 | 5.00 | |
| | | DGEBA[1] | 6.34 | | | 6.63 | | 5.00 |
| | | EXA4700[2] | | 9.08 | | | 9.49 | |
| | | YX4000H[3] | | | | | | |
| | | polydis[4] | | | | | | |
| | | HF-1M[5] | | 9.36 | | | | 2.84 |
| | | TPP[6] | | | | | | 0.04 |
| | | 2E4MZ[7] | 0.23 | 0.28 | 0.10 | 0.23 | 0.29 | |
| | | Polyvinyl acetal | 1.26 | 1.56 | 0.56 | 1.29 | 1.61 | 0.56 |
| | | Silica | 23.83 | 46.95 | 10.51 | 24.42 | 30.44 | 15.67 |
| | | Resin content (wt %) | 48% | 47% | 50% | 51% | 50% | 46% |
| Heat resistance | CTE (ppm/° C.) | α₁ (T < Tg) | 3.4 | 3.6 | 2.4 | 2.8 | 3.0 | 6.2 |
| | | Tg (° C.) | 170 | Tg-less | Tg-less | Tg-less | Tg-less | 175 |

TABLE 23

Filler composite

| | | Compound (synthetic example no.) | Example 38 | Example 39 | Example 40 | Example 41 | Example 42 | Example 43 | Example 44 | Example 45 |
|---|---|---|---|---|---|---|---|---|---|---|
| composition (g) | Silyl compound and epoxy | Synthetic Example 1 | 3.00 | 3.00 | | | | | | |
| | | Synthetic Example 2 | | | 3.00 | 3.00 | | | | |
| | | Synthetic Example 3 | | | | | 3.00 | 3.00 | | |
| | | Synthetic Example 10 | | | | | | | | |
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |

TABLE 23-continued

Filler composite

| | | | | | | | | | |
|---|---|---|---|---|---|---|---|---|---|
| | Synthetic Example 15 | | | | | | | | |
| | Synthetic Example 16 | | | | | | | | |
| | Synthetic Example 17 | | | | | | | | |
| | Synthetic Example 18 | | | | | | | | |
| | Synthetic Example 19 | | | | | | | | |
| | Synthetic Example 55 | | | | | | | 3.00 | 3.00 |
| | Synthetic Example 56 | | | | | | | | |
| | Synthetic Example 57 | | | | | | | | |
| | DGEBA[1] | | | | | | | | |
| | EXA4700[2] | | 5.09 | | 5.45 | | 5.70 | | |
| | YX4000H[3] | 3.64 | | 3.89 | | 4.07 | | | 3.64 |
| | polydis[4] | 0.77 | 1.08 | 0.83 | 1.16 | 0.87 | 1.21 | 0.64 | 0.77 |
| | HF-1M[5] | | | | | | | | |
| | Tpp[6] | | | | | | | | |
| | 2E4MZ[7] | 0.15 | 0.18 | 0.15 | 0.19 | 0.20 | 0.20 | 0.07 | 0.15 |
| | Polyvinyl acetal | 1.55 | 2.17 | 1.66 | 2.32 | 1.74 | 2.43 | 1.28 | 1.55 |
| | Silica | 73.70 | 93.21 | 77.11 | 98.06 | 79.61 | 101.5 | 40.37 | 73.71 |
| | Filler content (wt %) | 89 | 89 | 89 | 89 | 89 | 89 | 89 | 89 |
| Heat resistance | CTE ∥α₁ (ppm/° C.) (T < Tg) | 6.6 | 6.1 | 6.3 | 6.2 | 6.3 | 6.1 | 5.2 | 5.9 |
| | Tg (° C.) | Tg-less | Tg-less | Tg-less | Tg-less | Tg-less | Tg-less | Tg-less | Tg-less |

| | | | Compound (synthetic example no.) | Example 46 | Example 47 | Example 47 | Example 48 | Example 49 | Example 50 | Comparative Example 2 |
|---|---|---|---|---|---|---|---|---|---|---|
| composition (g) | Silyl compound and epoxy | | Synthetic Example 1 | | | | | | | |
| | | | Synthetic Example 2 | | | | | | | |
| | | | Synthetic Example 3 | | | | | | | |
| | | | Synthetic Example 10 | | | | | | | |
| | | | Synthetic Example 11 | | | | | | | |
| | | | Synthetic Example 12 | | | | | | | |
| | | | Synthetic Example 13 | | | | | | | |
| | | | Synthetic Example 14 | | | | | | | |
| | | | Synthetic Example 15 | | | | | | | |
| | | | Synthetic Example 16 | | | | | | | |
| | | | Synthetic Example 17 | | | | | | | |
| | | | Synthetic Example 18 | | | | | | | |
| | | | Synthetic Example 19 | | | | | | | |
| | | | Synthetic Example 55 | 3.00 | | | | | | |
| | | | Synthetic Example 56 | | 3.00 | 3.00 | 3.00 | | | |
| | | | Synthetic Example 57 | | | | | 3.00 | 3.00 | |
| | | | DGEBA[1] | | | | | | | 5.00 |
| | | | EXA4700[2] | 5.09 | | | 5.45 | | 5.70 | |
| | | | YX4000H[3] | | | 3.89 | | 4.07 | | |
| | | | polydis[4] | 1.08 | 0.64 | 0.83 | 1.16 | 0.87 | 1.21 | |
| | | | HF-1M[5] | 3.65 | | | 3.91 | | | 2.84 |
| | | | TPP[6] | | | | 0.03 | | | 0.05 |
| | | | 2E4MZ[7] | 0.05 | 0.07 | 0.15 | | 0.16 | 0.20 | |

TABLE 23-continued

| | | | | Filler composite | | | | | |
|---|---|---|---|---|---|---|---|---|---|
| | | Polyvinyl acetal | 2.17 | 1.28 | 1.66 | 2.32 | 1.74 | 2.43 | |
| | | Silica | 121.7 | 40.37 | 77.11 | 128.4 | 79.61 | 101.5 | 63.84 |
| | | Filler content (wt %) | 89 | 89 | 89 | 89 | 89 | 89 | 89 |
| Heat resistance | CTE (ppm/° C.) | $\alpha_1$ (T < Tg) | 5.2 | 5.1 | 5.7 | 5.1 | 5.8 | 5.7 | 8.9 |
| | | Tg (° C.) | Tg-less | Tg-less | Tg-less | Tg-less | Tg-less | Tg-less | 110 |

Note: the compounds used in the above Table 22 and Table 23 are as follows:

(1) DGEBA: diglycidyl ether of bisphenol A (Aldrich Co., Mw=377)

(2) EXA4700: dinaphthalene-based epoxy (EEW=162)

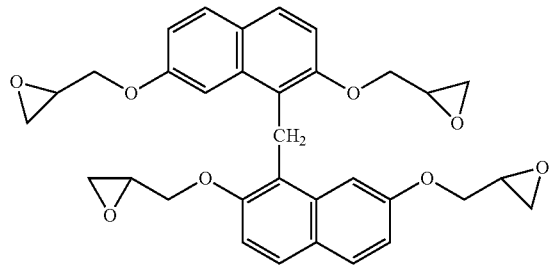 [SMILES: c1cc2ccc(OCC3CO3)c(Cc3c(OCC4CO4)ccc4ccc(OCC5CO5)cc34)c2cc1OCC1CO1]

(3) YX4000H: biphenyl-based epoxy

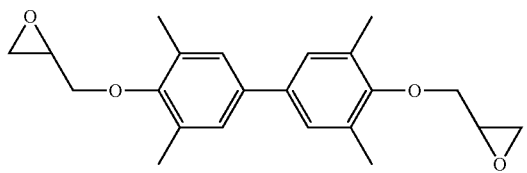 [SMILES: Cc1cc(-c2cc(C)c(OCC3CO3)c(C)c2)cc(C)c1OCC1CO1]

(4) Polydis: rubber modified epoxy (Strruktol Co.)

(5) HF-1M: phenol novolac-based curing agent (Meiwa Plastic Industries, HEW=107)

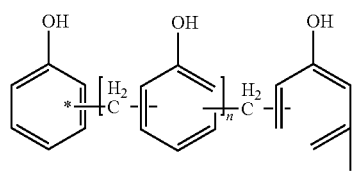

(6) TPP: triphenylphosphine (Aldrich Co.)

(7) 2E4MZ: 2-ethyl-4-methyl imidazole (Aldrich Co.)

As shown in Table 22, the glass fiber composites of Examples 1 to 37 including the alkoxysilyl compound of the present invention were found to have a lower CTE when compared to the glass fiber composite of Comparative Example 1, which did not include the alkoxysilyl compound of the present invention. Particularly, the glass fiber composite of the alkoxysilyl compound prepared according to Example 34, had a narrow dimensional change in accordance with temperature as shown in FIG. 1, and had a greatly decreased CTE when compared to the CTE of the glass fiber composite of Comparative Example 1. In addition, differently from Comparative Example 1 which showed glass transition temperature, Example 34 showed Tg-less transition properties where glass transition temperature was not shown, and the thermal properties of Example 34 were much better than those of the comparative example.

For some compositions in Table 22, glass transition temperature was observed. However, as shown in FIG. 2, the difference of the physical properties of the glass fiber composite of Comparative Example 1 before and after the glass transition temperature was apparently observed. For Example 1 in which glass transition temperature was not observed, the difference of the physical properties before and after the glass transition temperature was not very significant.

As shown in Table 23 and FIG. 3, the filler composites of Example 38 to Example 40 including the alkoxysilyl compounds of the present invention were found to have a lower CTE and Tg-less transition properties when compared to the filler composite of Comparative Example 2 which did not include the alkoxysilyl compound of the present invention.

Strips of the composites according to Example 1 and Comparative Example 1 in the above Table 22 were ignited, and photographic images of the burned strips are illustrated in FIG. 4. As shown in FIG. 4, the strip of the alkoxysilyl composite according to the present invention was extinguished naturally within 1 to 2 seconds. However, the strip of the composite not including an alkoxysilyl group according to Comparative Example 1 was burned out and completely combusted. Thus, it was known that the cured product including the alkoxysilyl compound according to the present invention had good flame retardant properties.

While the present invention has been shown and described in connection with the exemplary embodiments and attached drawings, it will be apparent to those skilled in the art that modifications and variations can be made without departing from the spirit and scope of the invention as defined by the appended claims.

The invention claimed is:

1. A composition of an alkoxysilyl compound having two or more alkoxysilyl groups selected from the group consisting of the following Formulae AI to II:

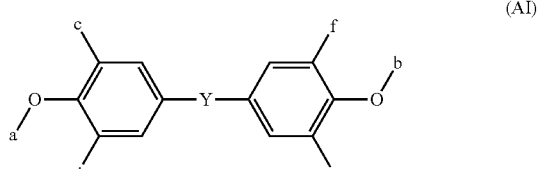

(AI)

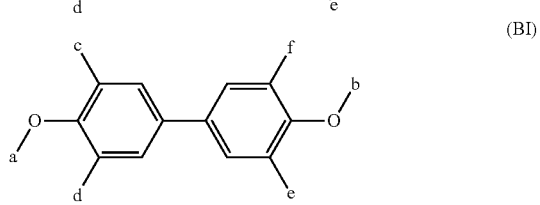

(BI)

-continued

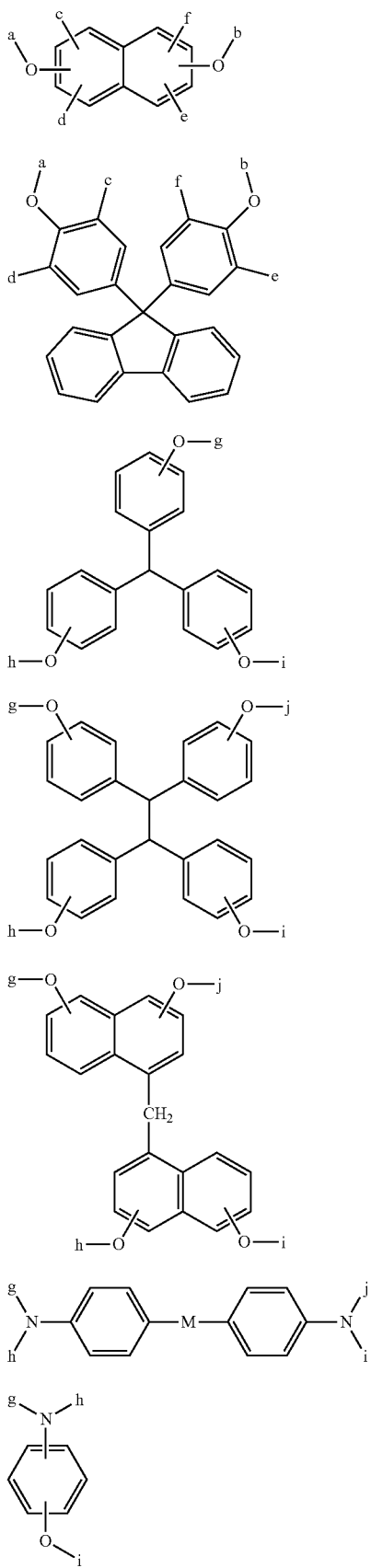

(CI)

(DI)

(EI)

(FI)

(GI)

(HI)

(II)

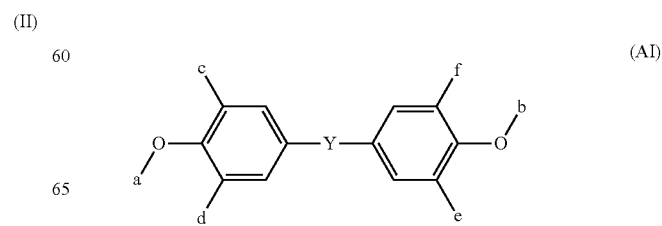

in Formulae AI to DI, substituents a and b are each independently selected from the group consisting of the following Formulae S1 and S2, hydrogen, and a $C_{1-10}$ alkenyl group, substituents c to f are each independently selected from the group consisting of the following Formula S1, hydrogen, a $C_{1-10}$ alkyl group, a $C_{1-10}$ alkenyl group, and a $C_{6-30}$ aryl group, and at least two substituents among a to f are selected from the group consisting of the following Formulae S1 and S2;

in Formula AI, Y is —$CH_2$—, —$C(CH_3)_2$—, —$C(CF_3)_2$—, —S— or —$SO_2$—;

in Formulae EI and II, at least two substituents of g to i are selected from the group consisting of the following Formulae S1 and S2, and the remainder thereof is hydrogen, a $C_{1-10}$ alkyl group, a $C_{1-10}$ alkenyl group, or a $C_{6-30}$ aryl group;

in Formulae FI to HI, at least two substituents of g to j are selected from the group consisting of the following Formulae S1 and S2, and the remainder thereof are hydrogen, a C1-10 alkyl group, a C1-10 alkenyl group, or a C6-30 aryl group;

in Formula HI, M is —$CH_2$—, —$C(CH_3)_2$—, —$C(CF_3)_2$—, —S— or —$SO_2$—; and a meta position of oxygen in the above Formula II is substituted with a linear or branched $C_{1-10}$ alkyl group, $$—(CH_2)_z—SiR_1R_2R_3 \quad \text{[Formula S1]}$$

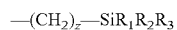

$$—CONH(CH_2)_z—SiR_1R_2R_3 \quad \text{[Formula S2]}$$

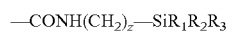

in Formulae S1 and S2, at least one of $R_1$ to $R_3$ is a linear or branched $C_{1-10}$ alkoxy group, the other thereof is a linear or branched $C_{1-10}$ alkyl group, and z is an integer of 3 to 10;

at least one filler selected from the group consisting of inorganic particles and fibers; and an epoxy resin;

wherein a molar ratio of an alkoxy group of the alkoxysilyl compound to an epoxy group of the epoxy compound is 0.90-10:1.

2. The composition of an alkoxysilyl compound of claim 1, wherein an amount of the inorganic particles is from 5 wt % to 95 wt % based on a total solids content of the composition of an alkoxysilyl compound.

3. The composition of an alkoxysilyl compound of claim 1, wherein the epoxy compound is at least one selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

4. The composition of an alkoxysilyl compound of claim 1, wherein the alkoxysilyl compound is selected from the group consisting of the following Formulae AI to CI:

(AI)

-continued

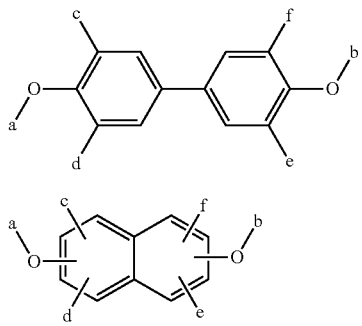
(BI)

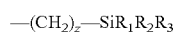
(CI)

where Y is —CH$_2$— or —C(CH$_3$)$_2$—,
c to f are hydrogen, and
a and b are each independently selected from the group consisting of the following Formulae S1 and S2:

—(CH$_2$)$_z$—SiR$_1$R$_2$R$_3$     [Formula S1]

—CONH(CH$_2$)$_z$—SiR$_1$R$_2$R$_3$     [Formula S2]

in Formulae S1 and S2, R$_1$ to R$_3$ are a C$_{1-2}$ alkoxy group, and z is an integer of 3 to 10.

5. The composition of an alkoxysilyl compound of claim 1, wherein the alkoxysilyl compound is selected from the group consisting of the following Formulae AI to CI:

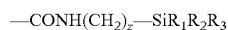
(AI)

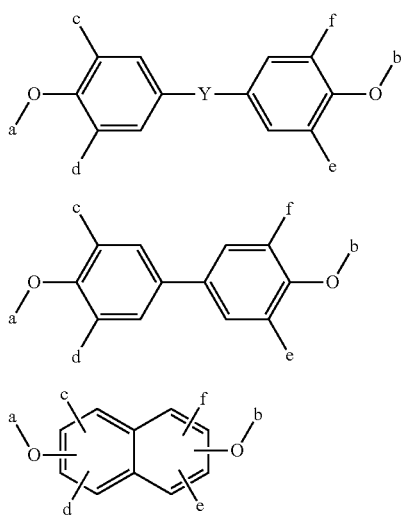
(BI)

(CI)

where Y is —CH$_2$— or —C(CH$_3$)$_2$—,
a and b are hydrogen, and
at least two of c to f are the following Formula S1, and a remainder thereof is selected from the group consisting of hydrogen and a C$_{1-10}$ alkenyl group:

—(CH$_2$)$_z$—SiR$_1$R$_2$R$_3$     [Formula S1]

in Formula S1, R$_1$ to R$_3$ are a C$_{1-2}$ alkoxy group, and z is an integer of 3 to 10.

6. The composition of an alkoxysilyl compound of claim 1, wherein the alkoxysilyl compound is selected from the group consisting of the following Formulae EI to GI:

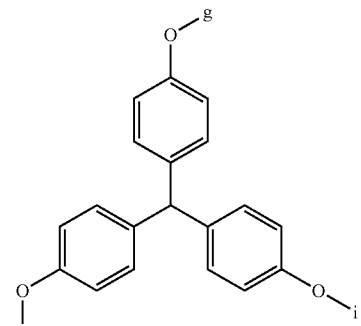
(EI)

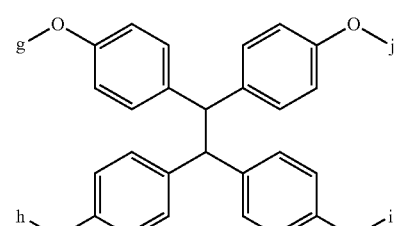
(FI)

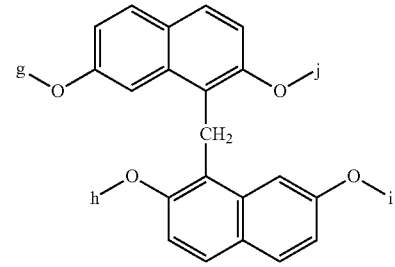
(GI)

where in Formula EI, one of g to i is hydrogen, and at least two of g to j are selected from the group consisting of the following Formula S1 and Formula S2, and
in Formulae FI and GI, at least one of g to j is hydrogen, at least two of g to j are selected from the group consisting of the following Formula S1 and Formula S2, and a remainder thereof is selected from the group consisting of H and a C1-10 alkenyl group:

—(CH$_2$)$_z$—SiR$_1$R$_2$R$_3$     [Formula S1]

in Formula S1, R$_1$ to R$_3$ are a linear or branched C$_{1-4}$alkoxy group, and z is an integer of 3 to 10, —CONH(CH$_2$)$_z$—SiR$_1$R$_2$R$_3$     [Formula S2]

in Formula S2, at least one of R$_1$ to R$_3$ is a linear or branched C$_{1-10}$ alkoxy group, the other thereof is a linear or branched C$_{1-10}$ alkyl group, and z is an integer of 3 to 10.

7. The composition of an alkoxysilyl compound of claim 1, wherein a molar ratio of an alkoxy group of the alkoxysilyl compound to an epoxy group of the epoxy compound is 0.90-1:1.

8. The composition of an alkoxysilyl compound of claim 1, further comprising a curing agent.

9. A cured product of the composition of an alkoxysilyl compound according to claim 1.

10. The cured product of claim 9, wherein the cured product has a coefficient of thermal expansion of 100 ppm/° C. or less.

11. The cured product of claim 10, wherein the cured product has a glass transition temperature of greater than 80° C., or does not show the glass transition temperature.

* * * * *